United States Patent [19]
Sanders et al.

[11] Patent Number: 6,140,078
[45] Date of Patent: Oct. 31, 2000

[54] SALT-INDUCIBLE PROMOTER DERIVABLE FROM A LACTIC ACID BACTERIUM, AND ITS USE IN A LACTIC ACID BACTERIUM FOR PRODUCTION OF A DESIRED PROTEIN

[75] Inventors: Jan W. Sanders; Jan Kok, both of Groningen; Gerard Venema, Haren; Adrianus M Ledeboer, Rotterdam, all of Netherlands

[73] Assignee: Unilever Patent Holdings, Vlaardingen, Netherlands

[21] Appl. No.: 09/068,195

[22] PCT Filed: Aug. 20, 1997

[86] PCT No.: PCT/EP97/04755

§ 371 Date: Jul. 29, 1998

§ 102(e) Date: Jul. 29, 1998

[87] PCT Pub. No.: WO98/10080

PCT Pub. Date: Mar. 12, 1998

[30] Foreign Application Priority Data

Sep. 5, 1996 [EP] European Pat. Off. ............... 96202444
Mar. 13, 1997 [EP] European Pat. Off. ............... 97200744

[51] Int. Cl.$^7$ ..................................................... C12P 21/06
[52] U.S. Cl. ................... 435/69.1; 435/243; 435/252.3; 435/320.1; 435/69.2; 536/23.1; 536/24.1; 536/24.5
[58] Field of Search .................. 536/24.1, 23.1, 536/24.5; 435/320.1, 69.1, 69.2, 71.1, 71.2, 243, 252.3

[56] References Cited

FOREIGN PATENT DOCUMENTS

WO 95/31562 11/1995 WIPO .
WO 95/31563 11/1995 WIPO .

*Primary Examiner*—Remy Yucel
*Attorney, Agent, or Firm*—Pillsbury Madison & Sutro LLP

[57] ABSTRACT

The invention provides a salt-inducible promoter present in SEQ ID NO: 10 and derivable from a lactic acid bacterium in isolation from the coding sequence normally controlled by said promoter in a wild-type lactic acid bacterium, with modifications and important parts thereof. Also provided are a recombinant vector and a transformed lactic acid bacterium comprising such promoter, and the production of a desired protein by such transformed bacterium, whereby the gene encoding said desired protein or a precursor thereof is expressed under control of such promoter. The desired protein can be secreted by the bacterium due to the presence of a signal sequence. The action of the salt-inducible promoter is enhanced at a pH of about 4–4.5 and/or by the presence of glutamic acid. Such process can be used in a fermentation process, in which the desired protein is a lytic protein causing lysis of the cells and release of the cell content. Or the desired protein can be an enzyme involved in flavour formation, e.g. in producing dressings, spreads, sausages and sour dough, or a protein functioning in a cheese production process, such as chymosin or a precursor thereof, or an enzyme involved in cheese flavour formation.

18 Claims, 59 Drawing Sheets

FIG. 6A

```
     PstI  'rnhB
  1  CTGCAGTAAT TTTGCCAAAG AATTGTAAAA TTCGTGGTTT GAATGATAGT AAAAAAGTGC
  1        AlaVal IleLeuProLys AsnCysLys IleArgGly LeuAsnAspSer LysLysVal 61  CAAAATCAAA GCATCATGCT ATTCTATCTG AAATTCAAGA AAAAGGCTTA GCGATTGGAG
 20        ProLysSer LysHisHisAla IleLeuSer GluIleGln GluLysAlaLeu AlaIleGly 121  TTGGAATTGT TGATGCCGAA AAAAATTGATG AAGTAAATAT TTATGAGGCG ACAAAAATTG
 40        ValGlyIle ValAspAlaGlu LysIleAsp GluValAsn IleTyrGluAla ThrLysIle 181  CAATGATTCA GGCAGTATCA AAATTATCTC TTAAACCTGA ACATCTCTTA ATAGATGCGA
 60        AlaMetIle GlnAlaValSer LysLeuSer LeuLysPro GluHisLeuLeu IleAspAla NotI
241  TGGTTTTAGA TTTGCCCATT GCTCAGACGA AAATCATTCA TGGAGATGCT CGTTCAGCTT
 80        MetValLeu AspLeuProIle AlaGlnThr LysIleIle HisGlyAspAla ArgSerAla 301  CAATTGCGGC CGCATCAATT GTAGCTAAAG TGACTCGTGA TGAAATGATG AAGGATTTCG
100        SerIleAla AlaAlaSerIle ValAlaLys ValThrArg AspGluMetMet LysAspPhe 361  CTTTAGAATT TCCAGAATAT GATTTTGAAC ATAATGCAGG CTATGGAACA GCAAACATC
120        AlaLeuGlu PheProGluTyr AspPheGlu HisAsnAla GlyTyrGlyThr AlaLysHis
```

FIG. 6B

```
                               EcoRI
421  TTGCAGCTCT GACAAAATAT GGTATCACAA GAATTCATCG GAAATCCTAT GAACCAATTA
140  LeuAlaAla LeuThrLysTyr GlyIleThr ArgIleHis ArgLysSerTyr GluProIle

481  AATCGATGGT CAATTTCAAA TAGTAGATTA TGTAAGTAAA AAAAGGAAAA CGTGAACGAT
160  LysSerMet ValAsnPheLys ***                          ----- - >

541  ATTTGGTCAC GTTTTTTTGC TGACAAGTCT GTCAGTAATT ATTTTCAAAG GTTTCAAAAA
     < -  - - - - -

601  TATAGTCTAG TAATTTGCTA GACTAATCTT CTGTTTTTTA ATAATAAACT AATTTTTTGT

661  TAATCTAAAT GACAAAATTA ATAAGCAGAG TTTTTTATAA AATTAGCTAC TTATAAAAAA

721  TTTGAAATTG GTATAGTTAA ATCTGTTATA ATTTCCAATA TTTTTTAATA ATAATTATTT
                                                              HindIII
781  TAACAAAATA CTTATATCAA AACTCTTTCA AGTATATATAA TGAGCGTTGT ATAAGCTTTT

841  ATGTCTTTCT ATATCAACTT TTAATAGAAA TATAAAGTAA TATAAATGTT TTTATAATAA
```

FIG. 6C

```
                                                          -35
901   ATTATGTGAG ATATATTTTT TTGTCCGTAC TGGTATAGAT TTGACGATTA AGTCTTAAAT
          -10
961   AAGTTATAAT CTCAATTGCG TAATTTCTTA AATACAGAAA TAACAACTAC ATTGGTAGAC

1021  TGATTAAAAA GTGTACTTGA TGAACTGTTA TAAACCTTAA AAAAATAAAA ATAATAGTTT
                         start rggL
                              ↑
1081  GGGggaTgtT AAAGATGTAT AAAAAATATG GAGATTGTTT TAAAAAGTTG CGAAACCAAA
       rbs            1      MetTyr    LysLysTyr  GlyAspCys  PheLysLysLeu  ArgAsnGln
                                                                                XbaI
1141  AGAATTTAGG GTTATCATAC TTTAGTAAAC TTGGAATAGA CCGTTCAAAT ATATCTAGAT
  16  LysAsnLeu  GlyLeuSerTyr PheSerLys LeuGlyIle  AspArgSerAsn IleSerArg 1201  TTGAACATGG AAAATGTATG AGCGTATAGA TTTGATGTTA GAAGAAATGC
  36  PheGluHis  GlyLysCysMet MetSerPhe GluArgIle  AspLeuMetLeu GluGluMet
```

FIG. 6D

```
1261  AAGTTCCGTT ATCTGAGTAC GAATTGATTG TAAATAATTT TATGCCGAAT TTCCAAGAAT
  56  GlnValPro LeuSerGluTyr GluLeuIle ValAsnAsn PheMetProAsn PheGlnGlu

1321  TTTTTATATT AGAATTGGAA AAAGCTGAAT TTAGCCAAAA TCGAGATAAA ATAAAAGAGT
  76  PhePheIle LeuGluLeuGlu LysAlaGlu PheSerGln AsnArgAspLys IleLysGlu
                                                                    HindIII
1381  TGTATTCTGA GGTCAAAGAA ACGGGGAATC ATTACTGAC GGTTACCGTG AAAACGAAGC
  96  LeuTyrSer GluValLysGlu ThrGlyAsn HisLeuLeu ThrValThrVal LysThrLys
                                                        HindIII
1441  TTGGGAATAT AAGTCAGACA GAAGTTAAAG AAATTGAAGC TTATCTTTGC AATATTGAAG
 116  LeuGlyAsn IleSerGlnThr GluValLys GluIleGlu AlaTyrLeuCys AsnIleGlu 1501  AGTGGGGATA TTTTGAACTT ACTTTATTTT ATTTGTATC TGATTATCTC AATGTCAATC
 136  GluTrpGly TyrPheGluLeu ThrLeuPhe TyrPheVal SerAspTyrLeu AsnValAsn 1561  AATTAGAATT GCTGCTTTTT AATTTTGATA AAAGATGTGA AAATTACTGT AGAGTCTTAA
 156  GlnLeuGlu LeuLeuLeuPhe AsnPheAsp LysArgCys GluAsnTyrCys ArgValLeu
```

FIG. 6E

```
1621  AATATAGAAG GAGACTATTG CAAATAGCCT ATAAAAGTGT TGCGATATAC GCGGCTAAAG
 176  LysTyrArg ArgArgLeuLeu GlnIleAla TyrLysSer ValAlaIleTyr AlaAlaLys

1681  GAGAAAGAAA AAAAGCCGAA AATATTTTAG AAATGACTAA AAAATATCGA ACTGTGGGAG
 196  GlyGluArg LysLysAlaGlu AsnIleLeu GluMetThr LysLysTyrArg ThrValGly

1741  TCGATTTATA TTCAGAAGTA TTAAGACATC TTGCTAGAGC TATCATTATT TTTAATTTTG
 216  ValAspLeu TyrSerGluVal LeuArgHis LeuAlaArg AlaIleIleIle PheAsnPhe

1801  AAAATGCAGA GATTGGGGAA GAAAAAATAA ATTATGCTCT TGAGATTTTG GAAGAATTTG
 236  GluAsnAla GluIleGlyGlu GluLysIle AsnTyrAla LeuGluIleLeu GluGluPhe

1861  GAGGAAAGAA GATAAAAGAA TTCTATCAGA ATAAAAATGGA AAAGTATTTG AAAAGGTCAA
 256  GlyGlyLys LysIleLysGlu PheTyrGln AsnLysMet GluLysTyrLeu LysArgSer
                                  EcoRI

1921  TTTAGTCTCT TTTGAGCTGT TGCTTTTAAAG CAACAGCTCA AAAGAGATTT TCTTTATTCT
 276  Ile***------------------>  <---------------

XbaI       -10
1981  AGAGCATATA CTAGAGGGTG AAGATAGGTT GTCTGAAGCA TTATAACTTG TCTTTTAAAA
                                            ↑
```

FIG. 6F

```
                              Start orfX
2041  AATTCAATCA TAAATATAag gaggtATGAT GAATCAAAAA AAATTATCAT TATTCGGTTT
   1                          rbs      Met AsnGlnLys LysLeuSer LeuPheGlyPhe 2101  TTTCGCATTA ACCGCTTCAA TGGTTTTGAC TGTCTATGAG TATCCGACTT TTGCCACGTC
  12  PheAlaLeu ThrAlaSer MetValLeu ThrValTrpGlu TyrProThrP heAlaThrSer 2161  AAAATTACAT TTGGTGTTCT TTTTACTTCT CGGAGGACTA CTATGGTTTT TGCCTGTAGC
  32  LysLeuHis LeuValPhe PheLeuLeu LeuGlyGlyLeu LeuTrpPhe LeuProValAla 2221  GCTCTGCGCA GCAGAAATGG CGACGGTTGA AGGCTGGAAA AATFFTGGAA TCTTTAGTTG
  52  LeuCysAla AlaGluMet AlaThrVal GluGlyTrpLys AsnGlyGly IlePheSerTrp ApaI
2341  AATTACAGTA GGTTTTGTCA CTATGATCTA TTTCATTTTA GGGGCCCTCT CTTATGTGTT
  92  IleThrVal GlyPheVal ThrMetIle TyrPheIleLeu GlyAlaLeu SerTyrValLeu
```

FIG. 6G

```
              Sau3A
2401  AAATTTCAG GCGCTCAATA CAGATCCATT GATAAAATTT ATTGGTTTAC TAATCATTTT
112         AsnPheGln AlaLeuAsn ThrAspPro LeuIleLysPhe IleGlyLeu LeuIleIlePhe

2461  TTGGGATTG ACTTTTCTC AATTAGGTGG GACGCAACGG ACTGCCAAAT TAGTAAAAGC
132         TrpGlyLeu ThrPheSer GlnLeuGly GlyThrGlnArg ThrAlaLys LeuValLysAla

2521  TGGCTTTGTA GTTGGAATAG TGATTCCATC GGTTATCTTG TTTGGATTAG CAGGCGGCATA
152         GlyPheVal ValGlyIle ValIlePro SerValIleLeu PheGlyLeu AlaAlaAlaTyr

2581  CTTTATCGGA GGCAATCCTA TAGAAATACC AATTAACAGC CATGCTTTTG TACCAGATTT
172         PheIleGly GlyAsnPro IleGluIle ProIleAsnSer HisAlaPhe ValProAspPhe

2641  TTCACAGGTA TCAACTTTAG TAGTTTTTGT TCTTTTTATT CTGGCTTATA TGGGGGTAGA
192         SerGlnVal SerThrLeu ValValPhe ValSerPheIle LeuAlaTyr MetGlyValGlu
```

FIG. 6H

```
2701  AGCCTCAGCT TCACATATTA ATGAACTTGA AAATCCAAAA CGAAATTATC CCTTAGCAAT
 212  AlaSerAla  SerHisIle  AsnGluLeu  GluAsnProLys ArgAsnTyr  ProLeuAlaMet

2761  GATTTATTA  GTAATTTTGG CTATTCTTT  AGATGCCATA GGTGGATTTT CTGTAGCAGC
 232  IleLeuLeu  ValIleLeu  AlaIleLeuSer LeuAspAlaIle GlyGlyPhe  SerValAlaAla

2821  AGTTATTCCT CAAAAAGAGT TATCATTAAG TGCAGGGGTA ATCCAAACTT TTCAAACGTT
 252  ValIlePro  GlnLysGlu  LeuSerLeu  SerAlaGlyVal IleGlnThr  PheGlnThrLeu

2881  AATCTTACAT TTTAATCATC ATTTGGGATG GTTAGTTAAA GTGATTGCAC TAATGATTGC
 272  IleLeuHis  PheAsnHis  HisLeuGlyTrpLeuValLys ValIleAla  LeuMetIleAla

XbaI
2941  CTTTGGGGTT ATGGGAGAAG TGAGTTCATG GGTTGTTGGT CCTTCTAGA
 292  PheGlyVal  MetGlyGlu  ValSerSer  TrpValValGly ProSerArg
```

FIG. 7A

```
RGGL    MY--KKYGDCFKKLRNQKNLGLSYFSKLGIDRSNISRFEHGKCMMSFERI              48
RGG1    MLIVKSSGKILKIIRESKNMSLKEVAAGDISVAQLSRYERGISSLTVDSF              50
ORF3    M-PYKRYGEIFKKLREQKNFSLSHFSEIGISKASLSRFELGQTMISFERL              49
         *  *  . *.. **. * .   **..  .  . ***.   ** .

RGGL    DLMLEEMQVPLSEYELIVNNFMPNFQEFFILELEKAEFSQNRDKIKELYS              98
RGG1    YSCLRNMSVSLAEFQYVYHNYREADDVVLSQKLSEAQRENNIVKLESILA             100
ORF3    DSALQEMNVTLAEYEHFINNFSMDYKEEFLEDIILADIADDVDKLHKL--              97
         *  . *    ***..*..*. .    .**    .  **. . **

RGGL    ------EVKETGNHLL-TVTVKTKLGN------ISQTEVKEIEAYLCNI              134
RGG1    GSEAMAQEFPEKKNYKLNTIVIRATLTSCNPDYQVSKGDIEFLTDYLFSV             150
                 *  *         * *  **              *  **
```

FIG. 7B

```
RGGL  EEWGYFELTLFYFVSDYLNVNQLELLFNFDKRCENYCRVLKYRRRLLQI           184
RGG1  EEWGRYELWLFTNSVNLLTLETFASEMINRTQFYNNLPENRRRIIKM             200
      ****.** .**   *           *    **     **..  .

RGGL  AYKSVAIYAAKGERKKAENILEMTKKYRTVGVDLYSEVLRHLARAIIIFN           234
RGG1  LLNVVSACIENNHLQVAMKFLNYIDNTKIPETDLYDRVLIKYHKALYSYK           250
       *.   *                     *       ***  **  * *.  .

RGGL  FENAEIGE--EKINYALEILEEFG-GKKIKEFYQNKMEKYLKR-SI               276
RGG1  VGNPHARHDIEQCLSTFEYLDSFGVARKLKEQFERIQLTVVADLQIE              297
       *              **    **.** *  ***       .
```

FIG. 8A

```
L. lactis      ------------------------------------AVILPKNCKIRGLNDSKKV    19
V. cholerae    ---------------------------------------PNRPIMGLNDSKKL    14
E. coli        MIEFVYPHT-QLVAGVDEVGRGPLVGAVVTAAVILDPARPIAGLNDSKKL         49
H. influenzae  M--FEYPQGYKLIAGVDEVGRGPLVGAVVTAAVILDPHNPIEGLADSKKL         48
                                     ****      *    ****** *****.

L. lactis      PKSKHHAILSEIQEKALAIGVGIVDAEKIDEVNIYEATKIAMIQAVSKLS         69
V. cholerae    SEKRRLALFPEIQVKALAWAVGRCSPQEIDELNIFQATMVAMQRAVAGLR         64
E. coli        SEKRRLALYEEIKEKALSWSLGRAEPHEIDELNILHATMLAMQRAVAGLH         99
H. influenzae  SEKKRLALAEEIKEKARAWALGRAEADEIDEINILQASLLAMTRAVKSLK         98
                ::  ** :  *:       :  .   :::*  ::**::  **..
```

FIG. 8B

```
L. lactis      LKPEHLLIDAMVL--DLPIAQTKIIHGDARSASIAAASIVAKVTRDEMMK  117
V. cholerae    IQPDLVLIDGNKIPK-LPMEAQAVVKGDLRVAQISAASIIAKVIRDQEME  113
E. coli        IAPEYVLIDGNRCPK-LPMPAMAVVKGDSRVPEISAASILAKVTRDAEMA  148
H. influenzae  IQPHFVLIDGNKIPKDLAIPAQAVVKGDSLVAEISAASILAKVARDQEME  148
                . *  .*..*    .       .:**.  *   * .**.**** .**  *.

L. lactis      DFALEFPEYDFEHNAGYGTAKHLAALTKYGITRIHRKSYEPIKSMVNFK-  166
V. cholerae    ALDKQYPQFGFANHKGYPTAAHFAAIEQHGVIEQHRKSFGPVKRALGE--  162
E. coli        ALDIVFPQYGFAQHKGYPTAFHLEKLAEHGATEHHRRSFGPVKRALGTCV  198
H. influenzae  ELDKQYPEYAFAQHKGYPTKLHLEKLAELGALPQHRRSFAPVKKALEQF-  197
                . :  *..  *  .**.*   *  :  .  .  ::* .*: *:

L. lactis      ----------------  166
V. cholerae    ----------------  162
E. coli        LILVSRLSKPESEDV   213
H. influenzae  ----------------  197
```

L. lactis
V. cholerae
E. coli
H. influenzae

FIG. 13A

```
     XbaI      -10      ↓ Transcription start
     TCTAGAGCAT ATACTAGAGG GTGAAGATAG GTTGTCTGAA GCATTATAAC TTGTCTTTTA
1
                         RBS            ScaI       EcoRV/ScaI
     AAAAATTCAA TCATAAATAT AAGGAGGTAT GatgAAAGTAC TGGAT|ACTTA TCAATGATGA
61                                ORFX' : MetLysTry TrpIle Leu IleAsnAspGlu ACCTTGGTTT GTCGGAAAAG ATGTAGCAAT TGCTATTGGT TACAAGAATT TCAGGGATGC
121  ProTrpPhe ValGlyLys AspValAlaIle AlaIleGly TyrLysAsn PheArgAspAla TTTGAAATCT CATGTAAAAG ACAAATATAA GAGGGAGTCG GACAGCAGTG ATTGGTTCAA
181  LeuLysSer HisValLys AspLysTyrLys ArgGluSer AspSerSer AspTrpPheAsn
                                                          RBS
     CGACAATATA TTATTGGAAA CGAACTGCAT AAAAAATAAA AAATAGGAGA AAGAACatgA
241  AspAsnIle LeuLeuGlu ThrAsnCysIle LysAsnLys Lys***           lytP: Met AAACATTTTT TAAAGATATG GCAGAACGTG CCATTAAAAC ATTTGCACAA GCAATGATTG
301  LysThrPhePhe LysAspMet AlaGluArg AlaIleLysThr PheAlaGln AlaMetIle
```

FIG. 13B

```
XbaI      -10         ↓ Transcription start
 1  TCTAGAGCAT ATACTAGAGG GTGAAGATAG GTTGTCTGAA GCATTATAAC TTGTCTTTTA RBS             ScaI
61  AAAGATTCAA TCATAAATAT AAGGAGGTAT GatgAAGTAC TTATTATATT TTGTAATCTT
                          ORFX': MetLysTyr LeuLeuTyr PheValIlePhe
                                 MetLys Ser TyrTyrIle Leu***

RBS
121 TAGAAAGGTA ATTATTTatg CCAGTATCAC GTGTTAAAGT TAAAAATAGA CATTTAAAAA
         ArgLysVal IleIleTyr AlaSerIleThr Cys***
         acmA: Met ProValSer ArgValLys ValLysAsnArg HisLeuLys
```

FIG. 23A

```
L.lactis    M-------NQKKLSLFGFFALTASMVLTVYEYPTFATSKLHLVFFLLGG      43
             *       *.*.****.***..* *** ********* ********
Shigella    MATSVQTGKAKQLTLLGFFAITASMVMAVYEYPTFATSGFSLVFFLLGG      50

L.lactis    LLWFLPVALCAAEMATVEGWKNGGIFSWVSQTLGERFGFAAIFFQWFQIT      93
            .*** ****.*********..* *.***.*.****  ***** *.*
Shigella    ILWFIPVGLCAAEMATVDGWEEGGVFAWVSNTLGPRWGFAAISFGYLQIA    100

L.lactis    VGFVTMIYFILGALSYVLNFQALNTDPLIKFIGLLIIFWGLTFSQLGGTQ    143
             **.*. ** ******* . ***   *** ****** *** ****. **
Shigella    IGFIPMLYFVLGALSYILKWPALNEDPITKTIAALIILWALALTQFGGTK    150
```

FIG. 23B

```
L.lactis    RTAKLVKAGFVVGIVIPSVILFGLAAYFIGGNPIEIPINSHAFVPDFSQ      193
            **..*  **:*.:* .*  ** * .* . * *   * *****
Shigella    YTARIAKVGFFAGILLPAFILIALAAIYLHSGAPVAIEMDSKTFFPDFSK      200

L.lactis    VATLVVFVSFILAYMGVEASASHINELENPKRNYPLAMILLVILAISLDA      243
            * ****** .* * ******  **:*  ** . :*** **:*:* *
Shigella    VGTLVVFVAFIGSYMGVEASATHVNEMSNPGRDYPLAMLLLMVAAICLSS      250

L.lactis    IGGFSVAAVIPQKELSLSAGVIQTFQTLILHFNHHLGWLVKVIALMIAFG      293
            .** *.**:**. ** ****:*:*: .:**:*:  .*:  ***::*  *
Shigella    VGGLSIAMVIPGNEINLSAGVMQTFTVLMSHVAPEIEWTVRVISALLLLG      300

L.lactis    VMGEVSSWVVGPSRGMFAAAQRGLLPKFLRKTNTHEVPVPLVMIQGIIVT      343
            *:.* *:***:***** .*: * **** :**:* **.:.*: :*
Shigella    VLAEIASWIVGPSRGMYVTAQKNLLPAAFAKMNKNGVPVTLVISQLVITS      350
```

FIG. 23C

```
L.lactis    LWGAVLTFGGGGNNLSFLVAISLTVVIYLVGYLLFFIVYFVLIYKKQNLK     393
            . **  ***** **** * .. ******  **   **  * **
Shigella    IALILTNTGGGNNMSFLIALALTVVIYLCAYFMLFIGYIVLKHPDLK       400

L.lactis    RTYNVPGKIIGKTIIAGIGFLLSIFALFISFVPPASIAKNETHTYQMILL    443
            **.*.**   * .. ** .* ***.**   ****.** *      . .*
Shigella    RTFNIPGGKGVKLVVAIVGLLTSIMAFIVSFLPPDNIQGDSTDMYVELLV   450

L.lactis    ISFVVTAILPFIIYELHDKKGHD----TIEEPTHFKAGDVNPAIYPAARG   489
            .**.*   *** ***.*. .**     *  * *             * **
Shigella    VSFLVVLALPFILYAVHDRKGKANTGVTLEPINSQNAPKGHFFLHPPARS   500

L.lactis    EHHIIKEEEHILKH   503
            *  *  .       
Shigella    PHYIVMNDK---KH   511
```

FIG. 24A

```
L. lactis GadB    MLYGKENRD---EAE-FLEPIFGSESEQVDLPKYKLAQQSIEPRVAYQLV    46
                  *.*       *** * *         **     *  **.. *
Synechocystis     MVHKKIDLNQLSEAESLLTPTYAARGLANSVSKYEMPETEMLPAIAYNLI    50

L. lactis         QDEMLDEGNARLNLATFCQTYMEPEAVKLMSQTLEKNAIDKSEYPRTTEI    96
                  *.  .**.****** * ***** **. *  *  *** ***  *.**
Synechocystis     HDELGLDGNSRLNLATFVTTWMEPEARQLMADTFDKNMIDKDEYPQTAEI    100

L. lactis         ENRCVNMIADLWNASEKGKIYGTSTIGSSEACMLGGMAMKFSWRKRAEKL    146
                  * ****.. ****     * ************.  ************
Synechocystis     ELRCVNILSRLWNAPASAEATGCSTIGSSEAAMLGGMAMKWKWRQR--RQ    148

L. lactis         GLDINAKKPNLVISSGYQVCWEKFCVYWDIEMREVPMDREHMSINLEKVM    196
                  ****           *********    *.* *    *
Synechocystis     AAGKPGDRPNLVMGINVQVCWEKFCRYWEVEPRFVPMEGDRYHISPEEAV    198

L. lactis         DYVDEYTIGVVGIMGITYTGRYDDIKALDNLIEEYNKQTDYKVYIHVDAA    246
                  .** *****.**.*.*.   *    *    *  *  *  *.***
Synechocystis     KLIDENTIGVIGILGSTFDGSYEPIEALNDALETLNQRTGWQVPLHIDAA    248
```

FIG. 24B

```
L. lactis      SGGLYAPFVEPELEWDFRLKNVISINTSGHKYGLVYPGVGWVLWRDKKYL  296
               ***  ***.*.* ****** * **************************..****
Synechocystis  SGGFIAPFLDPDLRWDFRLPWVKSINTSGHKYGLVYPGVGWIIWRDKEEL  298

L. lactis      PEELIFKVSYLGGELPTMAINFSHSASQLIGQYYNFVRYGFDGYKAIHER  346
               ******   **.***  *.***     *..  ******.*. .**. *
Synechocystis  PEELIFHCNYLGGDLPNFALNFSRPGNQVVAQYYNFLRLGKEGYRKIQQT  348

L. lactis      THKVAMYLAEEIEKTGMFEIMNDGAQLPIVCYKLKEN--SNRGWNLYDLA  394
               *.**. *  ** ..   *  *  .  *.     .*. *** .*
Synechocystis  CRDTALYLSGKIAQLGPFELLTDGGDIPVFAWRLKDEVLANTCYTLYDMA  398

L. lactis      DRLLMKGWQVPAYPLPKNLENEIIQRXXXXRADFGMNMAFNYVQDMQEAID  444
               *.* . ** ***** ***    ..**     *       ** **
Synechocystis  DKLRERGWLVPAYRMPKNREDLVVQRIVVKEGFSRDMADLLLADMERAIA  448

L. lactis      ALNKAHILFHQEPENKTYGFTH  466
               *  .   *    *..* *
Synechocystis  YFASQP---DHKPKQEGSHFSH  467
```

FIG. 27
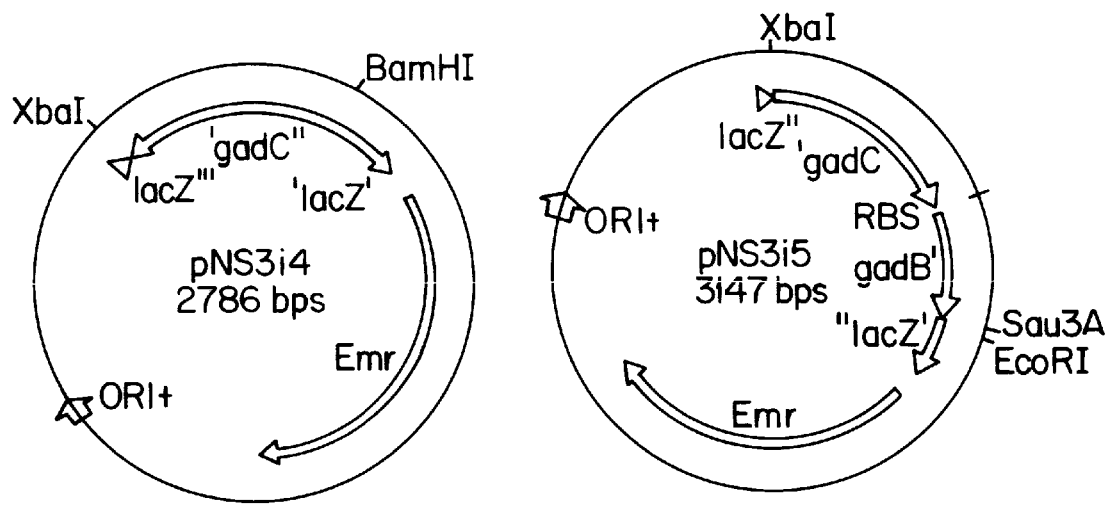
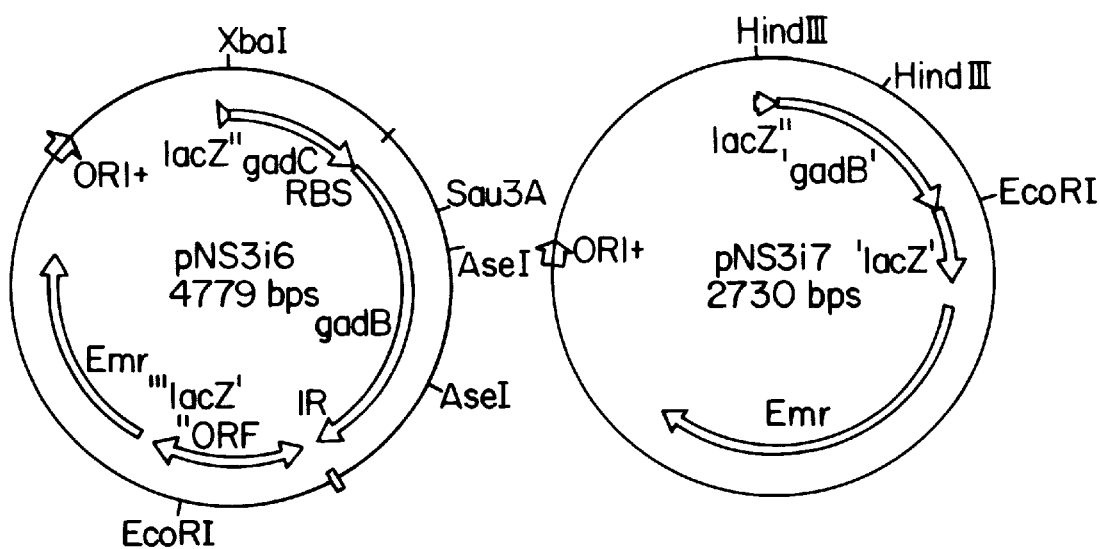

FIG. 29A

```
     PstI    'rnhB
     CT GCA GTA ATT TTG CCA AAG AAT TGT AAA ATT CGT GGT TTG AAT GAT    47
        Ala Val Ile Leu Pro Lys Asn Cys Lys Ile Arg Gly Leu Asn Asp    15

AGT AAA AAA GTG CCA AAA TCA AAG CAT CAT GCT ATT CTA TCT GAA ATT    95
     Ser Lys Lys Val Pro Lys Ser Lys His His Ala Ile Leu Ser Glu Ile    31

CAA GAA AAA GCG CTA GCG ATT GGA GTT GGA ATT GTT GAT GCC GAA AAA   143
     Gln Glu Lys Ala Leu Ala Ile Gly Val Gly Ile Val Asp Ala Glu Lys    47

ATT GAT GAA GTA AAT ATT TAT GAG GCG ACA AAA ATT GCA ATG ATT CAG   191
     Ile Asp Glu Val Asn Ile Tyr Glu Ala Thr Lys Ile Ala Met Ile Gln    63

GCA GTA TCA AAA TTA TCT CTT AAA CCT GAA CAT CTC TTA ATA GAT GCG   239
     Ala Val Ser Lys Leu Ser Leu Lys Pro Glu His Leu Leu Ile Asp Ala    79

ATG GTT TTA GAT TTG CCC ATT GCT CAG ACG AAA ATC ATT CAT GGA GAT   287
     Met Val Leu Asp Leu Pro Ile Ala Gln Thr Lys Ile Ile His Gly Asp    95
```

FIG. 29B

```
                NotI
GCT CGT TCA GCT TCA ATT GCG GCC GCA TCA ATT GTA GCT AAA GTG ACT     335
Ala Arg Ser Ala Ser Ile Ala Ala Ala Ser Ile Val Ala Lys Val Thr     111

CGT GAT GAA ATG ATG AAG GAT TTC GCT TTA GAA TTT CCA GAA TAT GAT     383
Arp Asp Glu Met Met Lys Asp Phe Ala Leu Glu Phe Pro Glu Tyr Asp     127

TTT GAA CAT AAT GCA GGC TAT GGA ACA GCA AAA CAT CTT GCA GCT CTG     431
Phe Glu His Asn Ala Gly Tyr Gly Thr Ala Lys His Leu Ala Ala Leu     143

ACA AAA TAT GGT ATC ACA AGA ATT CAT CGG AAA TCC TAT GAA CCA ATT     479
Thr Lys Tyr Gly Ile Thr Arg Ile His Arg Lys Ser Tyr Glu Pro Ile     159

AAA TCG ATG GTC AAT TTC AAA TAG TAGATTA TGTAAGTAAA AAAAGGAAAA       530
Lys Ser Met Val Asn Phe Lys ***                                     166

CGTGAACGAT ATTGGTCAC GTTTTTTTGC TGACAAGTCT GTCAGTAATT ATTTTCAAAG    590
---------->  <----------
```

FIG. 29C

```
GTTCAAAAAA TATAGTCTAG TAATTTGCTA GACTAATCTT CTGTTTTTTA ATAATAAACT    650
AATTTTTGT  TAATCTAAAT GACAAAATTA ATAAGCAGAG TTTTTATAAA AATTAGCTAC    710
TTATAAAAAA TTTGAAATTG GTATAGTTAA ATCTGTTATA ATTCCAATA  TTTTTTAATA    770
ATAATTATTT TAACAAAATA CTTATATCAA AACTCTTTCA AAGTATATAA TGAGCGTTGT    830
ATAAGCTTTT ATGTCTTTCT ATATCAACTT TTAATAGAAA TATAAAGTAA TATAAATGTT    890
                                                          -35
TTTATAATAA ATTATGTGAG ATATATTTTT TTGTCCGTAC TGGTATAGAT TTGACGATTA    950
           -10                ↓
AGTCTTAAAT AAGTTATAAT CTCAATTGCG TAATTTCTTA AATACAGAAA TAACAACTAC   1010
ATGGTAGAC  TGATTAAAAA GTGTACTTGA TGAACTGTTA TAAACCTTAA AAAAATAAAA   1070
```

FIG. 29D

```
                rbs           start gadR
ATAATAGTTT GGGggaTgtT AAAGATG TAT AAA AAA TAT GGA GAT TGT TTT AAA    1124
                            Met Tyr Lys Lys Tyr Gly Asp Cys Phe Lys   10

AAG TTG CGA AAC CAA AAG AAT TTA GGG TTA TCA TAC TTT AGT AAA CTT      1172
Lys Leu Arg Asn Gln Lys Asn Leu Gly Leu Ser Tyr Phe Ser Lys Leu       26

XbaI
GGA ATA GAC CGT TCA AAT ATA TCT AGA TTT GAA CAT GGA AAA TGT ATG      1220
Gly Ile Asp Arg Ser Asn Ile Ser Arg Phe Glu His Gly Lys Cys Met       42

ATG AGT TTT GAG CGT ATA GAT TTG ATG TTA GAA GAA ATG CAA GTT CCG      1268
Met Ser Phe Glu Arg Ile Asp Leu Met Leu Glu Glu Met Gln Val Pro       58

TTA TCT GAG TAC GAA TTG ATT GTA AAT AAT TTT ATG CCG AAT TTC CAA      1316
Leu Ser Glu Tyr Glu Leu Ile Val Asn Asn Phe Met Pro Asn Phe Gln       74

GAA TTT TTT ATA TTA GAA TTG GAA AAA GCT GAA TTT AGC CAA AAT CGA      1364
Glu Phe Phe Ile Leu Glu Leu Glu Lys Ala Glu Phe Ser Gln Asn Arg       90
```

FIG. 29E

```
GAT AAA ATA AAA GAG TTG TAT TCT GAG GTC AAA GAA ACG GGG AAT CAT    1412
Asp Lys Ile Lys Glu Leu Tyr Ser Glu Val Lys Glu Thr Gly Asn His     106

HindIII
TTA CTG ACG GTT ACC GTG AAA ACG AAG CTT GGG AAT ATA AGT CAG ACA    1460
Leu Leu Thr Val Thr Val Lys Thr Lys Leu Gly Asn Ile Ser Gln Thr     122

HindIII
GAA GTT AAA GAA ATT GAA GCT TAT CTT TGC AAT ATT GAA GAG TGG GGA    1508
Glu Val Lys Glu Ile Glu Ala Tyr Leu Cys Asn Ile Glu Glu Trp Gly     138

TAT TTT GAA CTT ACT TTA TTT TAT TTT GTA TCT GAT TAT CTC AAT GTC    1556
Tyr Phe Glu Leu Thr Leu Phe Tyr Phe Val Ser Asp Tyr Leu Asn Val     154

AAT CAA TTA GAA TTG CTG CTT TTT AAT TTT GAT AAA AGA TGT GAA AAT    1604
Asn Gln Leu Glu Leu Leu Leu Phe Asn Phe Asp Lys Arg Cys Glu Asn     170

TAC TGT AGA GTC TTA AAA TAT AGA AGG AGA CTA TTG CAA ATA GCC TAT    1652
Tyr Cys Arg Val Leu Lys Tyr Arg Arg Arg Leu Leu Gln Ile Ala Tyr     186
```

FIG. 29F

```
TAC TGT AGA GTC TTA AAA TAT AGA AGG AGA CTA TTG CAA ATA GCC TAT    1652
Tyr Cys Arg Val Leu Lys Tyr Arg Arg Arg Leu Leu Gln Ile Ala Tyr     186

AAA AGT GTT GCG ATA TAC GCG GCT AAA GGA GAA AGA AAA GCC GAA         1700
Lys Ser Val Ala Ile Tyr Ala Ala Lys Gly Glu Arg Lys Ala Glu         202

AAT ATT TTA GAA ATG ACT AAA AAA TAT CGA ACT GTG GGA GTC GAT TTA    1748
Asn Ile Leu Glu Met Thr Lys Lys Tyr Arg Thr Val Gly Val Asp Leu     218

TAT TCA GAA GTA TTA AGA CAT CTT GCT AGA GCT ATC ATT ATT TTT AAT    1796
Tyr Ser Glu Val Leu Arg His Leu Ala Arg Ala Ile Ile Ile Phe Asn     234

TTT GAA AAT GCA GAG ATT GGG GAA GAA AAA ATA AAT TAT GCT CTT GAG    1844
Phe Glu Asn Ala Glu Ile Gly Glu Glu Lys Ile Asn Tyr Ala Leu Glu     250

EcoRI
ATT TTG GAA GAA TTT GGA GGA AAG ATA AAA GAA TTC TAG CAG AAT        1892
Ile Leu Glu Glu Phe Gly Gly Lys Ile Lys Glu Phe Tyr Gln Asn         266

AAA ATG GAA AAG TAT TTG AAA AGG TCA ATT TAG TCTCTTTTGA GCTGTTGCTT  1945
Lys Met Glu Lys Tyr Leu Lys Arg Ser Ile ***                         276
```

FIG. 29G

```
                   XbaI           -10
                                    ↓
TAAAGCAACA GCTCAAAAGA GATTTTCTTT ATTCTAGAGC ATATACTAGA GGGTGAAGAT    2005
><-------- ---------- ---------- ----
                                              rbs
GTCTGAAGCA TTATAACTTG TCTTTTAAAA AGGTTAATTC AATCATAAAT Ataaggaggt    2065

Start gadC
ATG ATG AAT CAA AAA AAA TTA TCA TTA TTC GGT TTT TTC GCA TTA ACC     2113
Met Met Asn Gln Lys Lys Leu Ser Leu Phe Gly Phe Phe Ala Leu Thr       15

GCT TCA ATG GTT TTG ACT GTC TAT GAG TAT CCG ACT TTT GCC ACG TCA     2161
Ala Ser Met Val Leu Thr Val Tyr Glu Tyr Pro Thr Phe Ala Thr Ser       31

AAA TTA CAT TTG GTG TTC TTT TTA CTT CTC GGA GGA CTA CTA TGG TTT     2209
Lys Leu His Leu Val Phe Phe Leu Leu Leu Gly Gly Leu Leu Trp Phe       47

TTG CCT GTA GCG CTC TGC GCA GCA GAA ATG GCG ACG GTT GAA GGC TGG     2257
Leu Pro Val Ala Leu Cys Ala Ala Glu Met Ala Thr Val Glu Gly Trp       63
```

FIG. 29H

```
AAA AAT GGT GGA ATC TTT AGT TGG GTC AGT CAA ACT TTA GGT GAG CGC    2305
Lys Asn Gly Gly Ile Phe Ser Trp Val Ser Gln Thr Leu Gly Glu Arg     79

TTT GGT TTT GCA GCC ATA TTT TTT CAG TGG TTC CAA ATT ACA GTA GGT    2353
Phe Gly Phe Ala Ala Ile Phe Phe Gln Trp Phe Gln Ile Thr Val Gly     95
                                        ApaI
TTT GTC ACT ATG ATC TAT TTC ATT TTA GGG GCC CTC TCT TAT GTG TTA    2401
Phe Val Thr Met Ile Tyr Phe Ile Leu Gly Ala Leu Ser Tyr Val Leu    111
                            Sau3A
AAT TTT CAG GCG CTC AAT ACA GAT CCA TTG ATA AAA TTT ATT GGT TTA    2449
Asn Phe Gln Ala Leu Asn Thr Asp Pro Leu Ile Lys Phe Ile Gly Leu    127

CTA ATC ATT TTT TGG GGA TTG ACT TTT TCT CAA TTA GGT GTA GTT GGA    2497
Leu Ile Ile Phe Trp Gly Leu Thr Phe Ser Gln Leu Gly Val Val Gly    143

CGG ACT GCC AAA TTA GTA AAA GCT GGC TTT GTA GTT GGA ATA GTG ATT    2545
Arg Thr Ala Lys Leu Val Lys Ala Gly Phe Val Val Gly Ile Val Ile    159

CCA TCG GTT ATC TTG TTT GGA TTA GCA GCG GCA TAC TTT ATC GGA GGC    2593
Pro Ser Val Ile Leu Phe Gly Leu Ala Ala Ala Tyr Phe Ile Gly Gly    175
```

FIG. 29I

```
AAT CCT ATA GAA ATA CCA ATT AAC AGC CAT GCT TTT GTA CCA GAT TTT    2641
Asn Pro Ile Glu Ile Pro Ile Asn Ser His Ala Phe Val Pro Asp Phe     191

TCA CAG GTA TCA ACT TTA GTA GTT TTT GTT TCT TTT ATT CTG GCT TAT    2689
Ser Gln Val Ser Thr Leu Val Val Phe Val Ser Phe Ile Leu Ala Tyr     207

ATG GGG GTA GAA GCC TCA GCT TCA CAT ATT AAT GAA CTT GAA AAT CCA    2737
Met Gly Val Glu Ala Ser Ala Ser His Ile Asn Glu Leu Glu Asn Pro     223

AAA CGA AAT TAT CCC TTA GCA ATG ATT TTA GTA ATT TTG GCT ATT        2785
Lys Arg Asn Tyr Pro Leu Ala Met Ile Leu Leu Val Ile Leu Ala Ile     239

TCT TTA GAT GCC ATA GGT GGA TTT TCT GTA GCA GCA GTT ATT CCT CAA    2833
Ser Leu Asp Ala Ile Gly Gly Phe Ser Val Ala Ala Val Ile Pro Gln     255

AAA GAG TTA TCA TTA AGT GCA GGG GTA ATC CAA ACT TTT CAA ACG TTA    2881
Lys Glu Leu Ser Leu Ser Ala Gly Val Ile Gln Thr Phe Gln Thr Leu     271

ATC TTA CAT TTT AAT CAT CAT TTG GGA TGG TTA GTT AAA GTG ATT GCA    2929
Ile Leu His Phe Asn His His Leu Gly Trp Leu Val Lys Val Ile Ala     287

CTA ATG ATT GCC TTT GGG GTT ATG GGA GAA GTG AGT TCA TGG GTT GTT    2977
Leu Met Ile Ala Phe Gly Val Met Gly Glu Val Ser Ser Trp Val Val     303
```

FIG. 29J

```
                XbaI
GGT CCT TCT AGA GGG ATG TTT GCA GCA CAA AGA GGT TTA TTA CCA    3025
Gly Pro Ser Arg Gly Met Phe Ala Ala Gln Arg Gly Leu Leu Pro     319

AAA TTT TTA CGT AAA ACG AAT ACA CAT GAA GTC CCT GTT CCT TTA GTT 3073
Lys Phe Leu Arg Lys Thr Asn Thr His Glu Val Pro Val Pro Leu Val  335

ATG ATT CAA GGA ATC ATT GTT ACA CTT TGG GGC GCT GTA TTA ACT TTT 3121
Met Ile Gln Gly Ile Ile Val Thr Leu Trp Gly Ala Val Leu Thr Phe  351

GGA GGA GGA AAT AAT TTA TCT TTC TTA GTT GCC ATT TCA CTG ACT    3169
Gly Gly Gly Asn Asn Leu Ser Phe Leu Val Ala Ile Ser Leu Thr     367

GTA GTG ATT TAT TTG GTG GGT TAC CTC TTG TTC TTT ATT GTT TAC TTT 3217
Val Val Ile Tyr Leu Val Gly Tyr Leu Leu Phe Phe Ile Val Tyr Phe  383

GTT TTA ATC TAT AAA CAA AAT TTA AAG CGT ACT TAT AAT GTT CCA    3265
Val Leu Ile Tyr Lys Gln Asn Leu Lys Arg Thr Tyr Asn Val Pro     399
```

FIG. 29K

```
GGT AAA ATA ATA GGA AAA ACA ATC ATT GCA GGA ATT GGA TTC TTA TTA     3313
Gly Lys Ile Ile Gly Lys Thr Ile Ile Ala Gly Ile Gly Phe Leu Leu     415

TCA ATT TTT GCT CTA TTT ATT TCC TTT GTT CCT CCA GCA TCA ATT GCG     3361
Ser Ile Phe Ala Leu Phe Ile Ser Phe Val Pro Pro Ala Ser Ile Ala     431

AAA AAT GAA ACT CAC ACC TAT CAA ATG ATA CTT CTT ATA AGT TTT GTT     3409
Lys Asn Glu Thr His Thr Tyr Gln Met Ile Leu Leu Ile Ser Phe Val     447

GTG ACC GCT ATC TTG CCA TTT ATT TAT GAA TTG CAT GAT AAA AAG         3457
Val Thr Ala Ile Leu Pro Phe Ile Tyr Glu Leu His Asp Lys Lys         463

GGA CAT GAT ACT ATT GAA GAA CCA ACA CAC TTT AAA GCA GGA GAT GTG     3505
Gly His Asp Thr Ile Glu Glu Pro Thr His Phe Lys Ala Gly Asp Val     479

AAC CCT GCG ATT TAT CCA GCA GCT CGT GGA GAG CAT CAT ATT ATT AAA     3553
Asn Pro Ala Ile Tyr Pro Ala Ala Arg Gly Glu His His Ile Ile Lys     495

AAA GAA GAA CAT ATC TTA AAA CAT TGA AAAATTggag gATGTACAT ATG        3602
Lys Glu Glu His Ile Leu Lys His ***        rbs    start gadB Met     1
```

FIG. 29L

```
TTA TAC GGA AAA GAA AAT CGA GAT GAA GCG GAG TTC TTG GAA CCA ATT      3650
Leu Tyr Gly Lys Glu Asn Arg Asp Glu Ala Glu Phe Leu Glu Pro Ile       17

TTT GGT TCA GAA AGT GAA CAA GTG GAT TTA CCT AAA TAT AAA TTA GCT      3698
Phe Gly Ser Glu Ser Glu Gln Val Asp Leu Pro Lys Tyr Lys Leu Ala       33

CAA CAA TCA ATT GAG CCT CGA GTG GCC TAT CAG TTA GTT CAA GAT GAA      3746
Gln Gln Ser Ile Glu Pro Arg Val Ala Tyr Gln Leu Val Gln Asp Glu       49

ATG CTA GAT GAA GGG AAC GCT CGT TTA AAT TTG GCC ACA TTC TGT CAA      3794
Met Leu Asp Glu Gly Asn Ala Arg Leu Asn Leu Ala Thr Phe Cys Gln       65

ACT TAT ATG GAA CCT GAA GCA GTC AAG CTG ATG AGT CAG ACC TTG GAA      3842
Thr Tyr Met Glu Pro Glu Ala Val Lys Leu Met Ser Gln Thr Leu Glu       81

AAA AAT GCG ATT GAC AAA TCA GAA TAT CCA AGA ACA ACT GAA ATT GAA      3890
Lys Asn Ala Ile Asp Lys Ser Glu Tyr Pro Arg Thr Thr Glu Ile Glu       97

AAC CGT TGC GTC AAC ATG ATC GCT GAC CTT TGG AAT GCG AGT GAA AAA      3938
Asn Arg Cys Val Asn Met Ile Ala Asp Leu Trp Asn Ala Ser Glu Lys      113
```

FIG. 29M

```
GGA AAA ATT TAT GGG ACT TCG ACA ATT GGT TCT TCA GAA GCT TGT ATG     3986
Gly Lys Ile Tyr Gly Thr Ser Thr Ile Gly Ser Ser Glu Ala Cys Met     129

CTT GGG GGA ATG GCT ATG AAG TTT TCT TGG CGT AAG CGA GCA GAA AAA     4034
Leu Gly Gly Met Ala Met Lys Phe Ser Trp Arg Lys Arg Ala Glu Lys     145

TTA GGC CTA GAT ATT AAT GCG AAA AAG CCA AAC TTA GTC ATT TCC TCT     4082
Leu Gly Leu Asp Ile Asn Ala Lys Lys Pro Asn Leu Val Ile Ser Ser     161

GGT TAT CAA GTT TGC GTT GAA AAA TTC TGT GTT TAT TGG GAT ATT GAA     4130
Gly Tyr Gln Val Cys Val Glu Lys Phe Cys Val Tyr Trp Asp Ile Glu     177

ATG AGA GAA GTG CCA ATG GAT AGA GAA CAT ATG TCA ATC AAT TTG GAA     4178
Met Arg Glu Val Pro Met Asp Arg Glu His Met Ser Ile Asn Leu Glu     193

AAA GTG ATG GAT TAT GTT GAT GAA TAT ACG ATT GGA GTA GTT GGA ATT     4226
Lys Val Met Asp Tyr Val Asp Glu Tyr Thr Ile Gly Val Val Gly Ile     209

ATG GGG ATTT ACT TAT ACT GGT CGT TAT GAT GAT ATC AAA GCT TTG GAT    4274
Met Gly Ile Thr Tyr Thr Gly Arg Tyr Asp Asp Ile Lys Ala Leu Asp    225
```

FIG. 29N

```
AAT TTG ATT GAA GAA TAT AAT AAA CAG ACA GAC TAC AAA GTT TAT ATT    4322
Asn Leu Ile Glu Glu Tyr Asn Lys Gln Thr Asp Tyr Lys Val Tyr Ile    241

CAC GTA GAT GCT GCT TCA GGA GGA CTT TAT GCT CCT TTT GTT GAG CCA    4370
His Val Asp Ala Ala Ser Gly Gly Leu Tyr Ala Pro Phe Val Glu Pro    257

GAA CTT GAG TGG GAT TTC CGT TTG AAA AAT GTC ATT TCA ATC AAT ACT    4418
Glu Leu Glu Trp Asp Phe Arg Leu Lys Asn Val Ile Ser Ile Asn Thr    273

TCA GGA CAT AAA TAT GGT TTA GTA TAT CCT GGT GTA GGT TGG GTC TTG    4466
Ser Gly His Lys Tyr Gly Leu Val Tyr Pro Gly Val Gly Trp Val Leu    289

TGG CGT GAC AAA AAA TAT TTA CCT GAA GAG TTA ATT TTT AAA GTA AGT    4514
Trp Arg Asp Lys Lys Tyr Leu Pro Glu Glu Leu Ile Phe Lys Val Ser    305

TAT CTT GGA GGA GAA TTA CCA ACA ATG GCG ATT AAT TTT TCT CAC AGT    4562
Tyr Leu Gly Gly Glu Leu Pro Thr Met Ala Ile Asn Phe Ser His Ser    321

GCT TCT CAA TTA ATC GCT CAA TAC TAT AAT TTT GTA CGT TAT GGA TTT    4610
Ala Ser Gln Leu Ile Ala Gln Tyr Tyr Asn Phe Val Arg Tyr Gly Phe    337
```

FIG. 290

```
GAT GGA TAT AAA GCT ATT CAT GAG AGA ACG CAT AAA GTA GCC ATG TAT   4658
Asp Gly Tyr Lys Ala Ile His Glu Arg Thr His Lys Val Ala Met Tyr    353

TTA GCA GAA GAA ATT GAA ATT GAA AAA ACA GGA ATG TTT GAG ATT ATG AAC GAT   4706
Leu Ala Glu Glu Ile Glu Ile Glu Lys Thr Gly Met Phe Glu Ile Met Asn Asp    369

GGG GCA CAA TTA CCA ATT GTC TGC TAC AAA TTA AAA GAA AAT TCA AAC   4754
Gly Ala Gln Leu Pro Ile Val Cys Tyr Lys Leu Lys Glu Asn Ser Asn    385

CGT GGT TGG AAT CTT TAT GAT TTG GCA GAT CGT TTA TTA ATG AAG GGA   4802
Arg Gly Trp Asn Leu Tyr Asp Leu Ala Asp Arg Leu Leu Met Lys Gly    401

TGG CAA GTG CCT GCT TAT CCA CTT CCT AAA AAT TTG GAA AAT GAA ATC   4850
Trp Gln Val Pro Ala Tyr Pro Leu Pro Lys Asn Leu Glu Asn Glu Ile    417

ATT CAA CGT TTA GTA ATT CGA GCA GAT TTC GGG ATG AAT ATG GCA TTT   4898
Ile Gln Arg Leu Val Ile Arg Ala Asp Phe Gly Met Asn Met Ala Phe    433

AAC TAT GTT CAA GAT ATG CAA GAA GCA ATT GAT GCA CTA AAT AAG GCT   4946
Asn Tyr Val Gln Asp Met Gln Glu Ala Ile Asp Ala Leu Asn Lys Ala    449
```

FIG. 29P

```
CAT ATT CTA TTT CAT CAG GAA CCT GAA AAT AAA ACA TAT GGC TTT ACT      4994
His Ile Leu Phe His Gln Glu Pro Glu Asn Lys Thr Tyr Gly Phe Thr       465
CAC TAA AGATAAAAGC GATATATCTA AGATATATCG CTTTTATTTT GTTTTAGGCT        5050
His ***         <-------------------------------                      466

ATTTACTAAT TAGCTTGTCG CTTA TTA TTT TTC ATA GTA TTT ATC CAA AAT        5101
                          *** Lys Glu Tyr Tyr Lys Asp Leu Ile          -8

TTC CAT TTT TAA AGG AGT AAT TTT AGA TAG GGG GGC AGT TAG ACT TGT       5149
Glu Met Lys Leu Pro Thr Ile Lys Ser Leu Pro Ala Thr Leu Ser Thr       -24

TCT TAG GAA GAG CTT ATC TTC AAT GTT GAT GAT ACC CAG ATA TTT AAC       5197
Arg Leu Phe Leu Lys Asp Glu Ile Asn Ile Ile Gly Leu Tyr Lys Val       -40

TTG AGG GTA GTT AGC ATT GAC TTC TAT AAT TTG GGC TTT TTT CTC ACT       5245
Gln Pro Tyr Asn Ala Asn Val Glu Ile Ile Gln Ala Lys Lys Glu Ser       -56

AAT ATT TTC GTC TGT CAC GGG CAC ATC TAG GTT GAC CGT TCT TTC TTT       5293
Ile Asn Glu Asp Thr Val Pro Val Asp Leu Asn Val Thr Arg Glu Lys       -72
```

FIG. 29Q

```
ATA AGA GTA ATT TTT GAG AGC AAT ATT TCG GTT TGG AAT AAA AGT      5341
Tyr Ser Tyr Asn Lys Leu Ala Ala Ile Asn Arg Asn Pro Ile Phe Thr   -88

AGT CGC ACC GTC GGC TCC GAT AAC AGT AAT GGA ACG AAT TCC TAC GGT  5389
Thr Ala Gly Asp Ala Gly Ile Val Thr Ile Ser Arg Ile Gly Val Thr  -104

TTT CAC TCC CTC AAT ATC AAG ACC GGC AAA GGC AAC CGT ATC CGC      5437
Lys Val Val Gly Glu Ile Asp Leu Gly Ala Phe Ala Val Thr Asp Ala  -120

AAC ATT GAT TTG ATG TTC AAC GAT AAT AAA GAA ACC ATT AAT GAT ATC  5485
Val Asn Ile Gln His Glu Val Ile Ile Phe Phe Gly Asn Ile Ile Asp  -136

AGC GAC TAA ATC TCG TCC AGC GAA ACC AAG AGC GAC TCC AAG GAT ACC  5533
Ala Val Leu Asp Arg Gly Ala Phe Gly Leu Ala Val Gly Leu Ile Gly  -152
                    ʼORF    EcoRI
CGC GCC AGC TAG GAC ATT TGC AAC AGG AATTC                         5565
Ala Gly Ala Leu Val Asn Ala Val Pro Leu                          -162
```

SALT-INDUCIBLE PROMOTER DERIVABLE FROM A LACTIC ACID BACTERIUM, AND ITS USE IN A LACTIC ACID BACTERIUM FOR PRODUCTION OF A DESIRED PROTEIN

This application is the national phase of international application PCT/EP97/04755 filed Aug. 20, 1997 which designated the U.S.

The invention relates to a salt-inducible promoter derivable from a lactic acid bacterium.

BACKGROUND OF THE INVENTION AND PRIOR ART

It is known that salt-inducible promoters exist in plants and cyanobacteria; the latter are rather specialised bacteria which can be used for nitrogen-fixation of soil as natural fertilisation and which taxonomically are quite separate from other bacteria.

Although inducible promoter systems are known in Gram-negative bacteria like *E. coli* and in the Gram-positive bacterium *Bacillus subtilis*, while recently in WO 95/31563 (Quest International B.V. (A. Nauta c.s.); see ref. 36) an inducible promoter system was described for lactic acid bacteria or their phages, no literature was found relating to salt-inducible promoters active in microorganisms apart from the above mentioned rather specialised cyanobacteria. Although the expression "salt-initiated induction system" was present in said WO 95/31563 (Quest International B.V. (A. Nauta c.s.); ref. 36), no specific salt-initiated induction system was disclosed.

The present invention provides for the first time a salt-inducible promoter for lactic acid bacteria and its use in the production of polypeptides by lactic acid bacteria.

SUMMARY OF THE INVENTION

The invention provides a salt-inducible promoter derivable from a lactic acid bacterium, in particular a salt-inducible promoter the nucleotide sequence of which is present in SEQ. ID. NO: 10 and in FIGS. 6A-H. The advantage of a salt-inducible promoter active in lactic acid bacteria is first of all that salt is a natural food ingredient and therefore can be used as a food-grade inducer in food fermentation processes. For instance, during the salting stage of cheese curd various processes can be started when the higher salt concentration is used to trigger the formation of various proteins or peptides. Such processes include induced production and secretion of compounds which can contribute to the properties of the final cheese, e.g. enzymes and/or peptides that contribute to the formation of flavour compounds, and lysis of the lactic acid bacteria whereby peptidolytic enzymes are liberated by which the cheese ripening process is enhanced. Another process in which a salt-inducible promoter can be used advantageously is a process for the production of any protein or secondary metabolite by a food-grade microorganism, especially a lactic acid bacterium, whereby at the end of the culturing at a high cell density the microorganism is induced by a salt to produce the desired protein or secondary metabolite. As will be shown in the Examples, in this specification the term "salt" does only not mean common salt, i.e. sodium chloride, but also includes other halides like alkali metal, earth alkali metal and ammonium halides. In addition to the salt-induction by NaCl, KCl, $NH_4Cl$, $CaCl_2$, $MgCl_2$, NaI, and KI exemplified in Examples 1 and 2 (see also Table 3 below), it is envisaged that also other halides, i.e. bromides and perhaps fluorides, as well as halides with other cations such as substituted ammonium compounds, e.g. tetramethylammonium, or other metallic cations, e.g. $Al^{3+}$, will show the salt-inducing effect.

Still another process which can benefit from the presence of a salt-inducible promoter in a microorganism is the production of secondary metabolites, e.g. flavour or taste ingredients, in situ in a fermented product upon the addition of salt, examples of which include dressings and water-containing spreads, as well as sausages and sour dough. The invention also provides a recombinant vector and a transformed lactic acid bacterium each comprising such a salt-inducible promoter.

Figure 1:
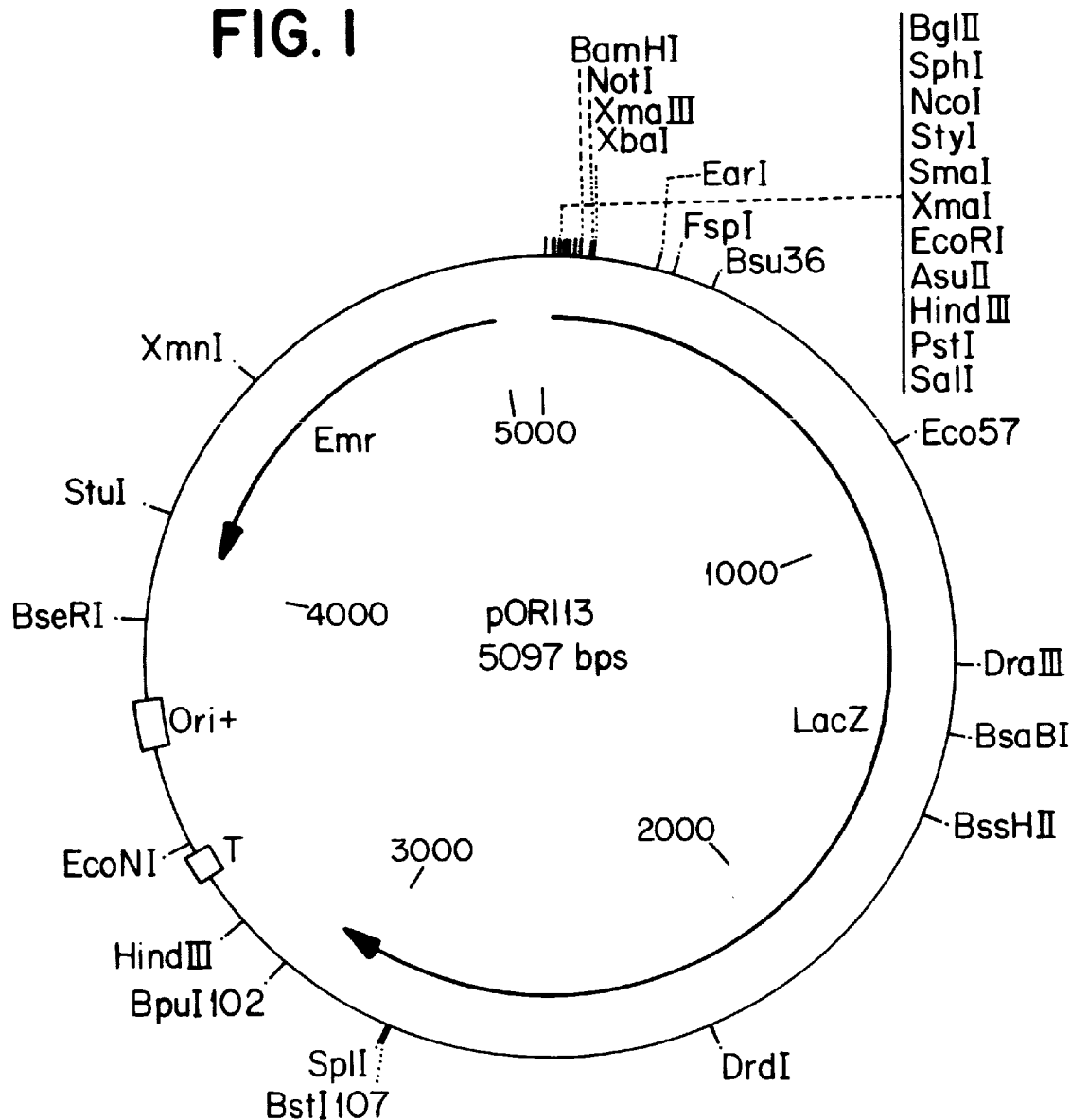
FIG. 1.

Schematic representation of plasmid pORI13. ori+, plus origin of pWV01; Em$^r$, erythromycin resistance gene; T, terminator; lacz, promoterless *E. coli* β-galactosidase gene fused to the ribosome binding site and translational start codon of the lactococcal ORF32 (see Example 1.1 below). Stop codons are indicated by asterisks.

FIG. 2.

Scheme of the construction of plasmid pLS12 starting from plasmids pBSK+, pKL10, and pMG60 (see Example 1.1.4). The immediate result of the ligation of (1) the multiple cloning site of pBSK+ containing the Km$^r$ gene in the BamHI site and (2) BamHI-digested pLS11 is a precursor of pLS12 which is not depicted (see 1.1.4 below). After BamHI-digestion of this precursor and self-ligation pLS12 is formed. This is indicated by the dashed arrows.

FIG. 3.

Scheme of the construction of plasmid pLS13 starting from plasmids pORI28 and pLS12 (see Example 1.1.4).

FIG. 4.

Scheme of the construction of plasmid pORI13 starting from plasmids pLS13, pMG60 and pORI28 (see Example 1.1.5).

FIGS. 5A-B.

Deletion analysis NS3 (see Example 1.3). This shows the schematic drawings of the relevant parts of plasmids pNS3 (10 kb insert), pNS3d (2.4 kb insert), pNS3b (1.0 kb insert), pNS3e (0.5 kb insert), and pNS3f (0.4 kb insert).

FIGS. 6A-H.

Nucleotide sequence (SEQ. ID. NO: 11) of the NS3 locus and deduced amino acid sequences (SEQ. ID. NO: 22–24) of the 3' end of rnhB, of rggL, and of the 5' end of orfX (see Example 1.5). Facing arrows, inverted repeats; rbs, ribosome binding site; −10 and −35 hexanucleotides are in boldface and underlined; vertical arrow, transcription start point. Stop codons are indicated with asterisks. A number of relevant restriction enzyme sites are shown.

FIGS. 7A-B.

Alignment of the deduced translation products of rggL (see SEQ. ID. NO: 11) with rgg from *S. gordonii* (see ref. 27; M. C. Sulavik c.s.; 1992 and SEQ. ID. NO: 12) and part of ORF3, found downstream of the *L. lactis* C2 pip gene (see ref. 30; B. L. Geller c.s; 1993 and SEQ. ID. NO: 13). Asterisks indicate identical amino acids; conservative amino acids are indicated by dots (see Example 1.4).

FIGS. 8A-B.

Alignment of the translation products of the 3' part of rnhb from *L. lactis* (see SEQ. ID. NO: 14) and Vibrio cholerae (U30472) (see SEQ. ID. NO: 15) and the complete rnhB genes from *E. coli* (see ref. 18; M. Itaya; 1990 and SEQ. ID. NO: 16) and *Haemophilus influenzae* (see ref. 33; R. D. Fleischmann c.s.; 1995 and SEQ. ID. NO: 17). The highest homology was found with *E. coli* rnhB (44% identical plus 13.9% similar amino acids). Asterisks, identical amino acids; periods, similar amino acids (see Example 1.4).

FIG. 9.

Genomic organization of the NS3 locus. Prgg: rggrL promoter, IR, inverted repeat, PNaCl: salt-inducible promoter (see Example 1.4).

FIG. 10.

Sequence analysis NS3. The total PstI-XbaI fragment given in FIG. 6 is given here schematically with relevant restriction sites and the main features of the DNA. The indicated fragments were subcloned giving plasmids pNS3I–pNS3VI and pNS3i4 (see also FIG. 27 and Example 1.4.1). Also primers used for sequencing are given.

FIG. 11.

Autoradiogram of a northern blot of total RNA isolated from MG1363 or MGNS3i3 (rggL$^-$) cells grown in the absence or presence of 0.5 M NaCl. The blot was hybridized with radioactively labeled XbaI-Sau3A fragment encoding the 5' end of orfX. The sizes of an RNA marker are given in the left margin (see Example 1.6).

FIG. 12.

β-galactosidase activity of NS3 as a function of the NaCl concentration in the culture medium. Samples were taken 7 hours after addition of NaCl to a 1:100 diluted culture (see Example 2).

FIGS. 13A and 13B.

Figure 4:
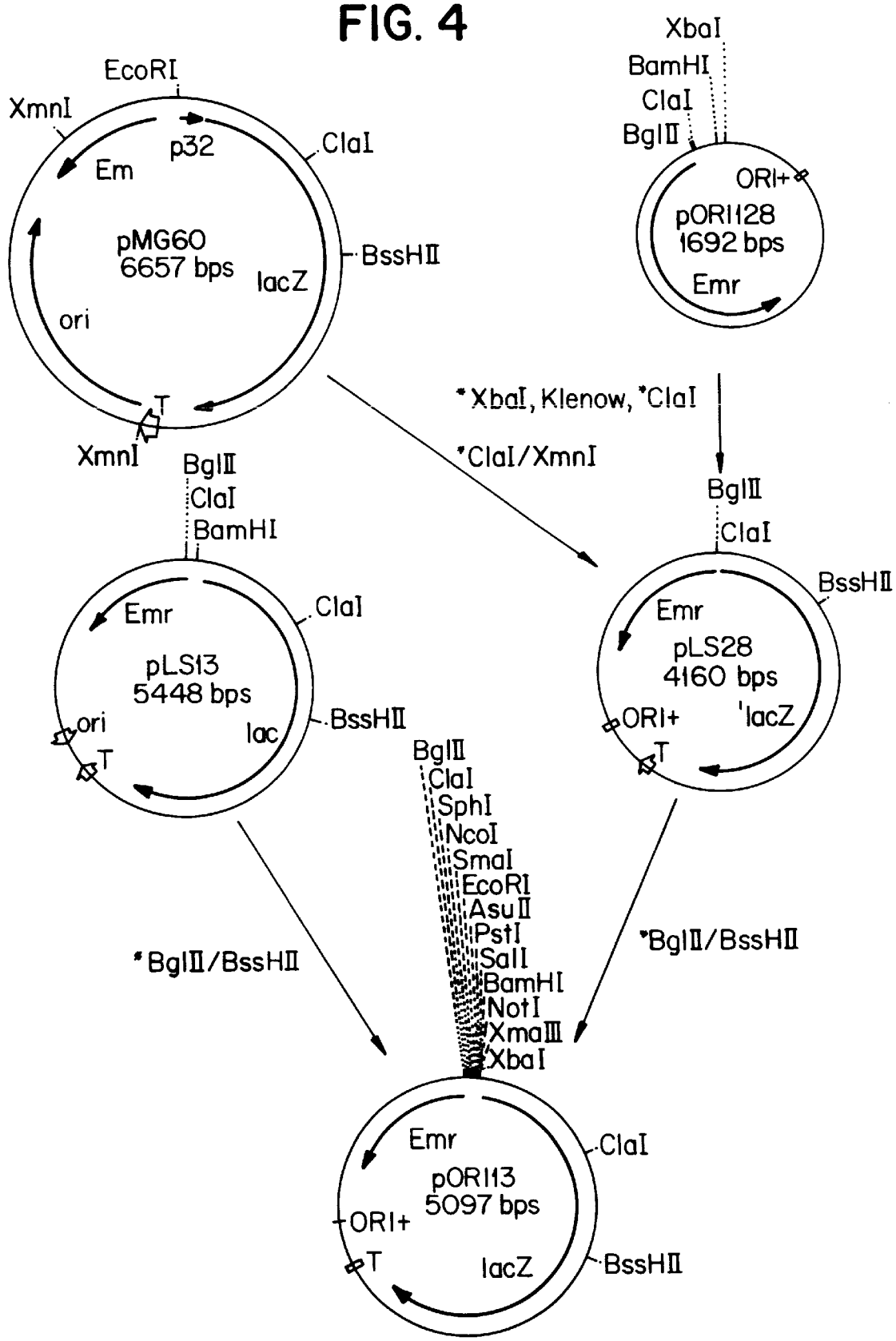

Nucleotide sequences of the fusion points of truncated orfX with either lytPR or acmA in pNS3PR (Part A) or pNS3AL3 (Part B); see also SEQ. ID. NO: 18 and SEQ. ID. NO: 19, and 20 respectively and Examples 3 and 4. The translation of both genes is given below the DNA sequence. Translational stops are indicated with asterisk triplets. The transcription start site is shown by the vertical arrow, while the RBS's are in boldface. The XbaI site corresponds to position 1981 in FIG. 4. The EcoRV and ScaI sites were used to make the fusions.

FIG. 14.

Renaturing SDS-12.5% PAGE showing cell wall hydrolase activity in cell extracts prepared from samples taken 6 hours after addition of NaCl. Lanes: 1 and 2, LL108 (pNS378); 3 and 4, LL108(pNS3PR); 5 and 6, LL108 (pNS3AL3); 1, 3 and 5, no NaCl; 2, 4 and 6, plus NaCl. Molecular masses (in kilodaltons) of marker proteins are indicated on the left (see Examples 3 and 4).

FIG. 15.

Optical density at 600 nm of LL108(pNS378)(squares) and LL108(pNS3PR)(triangles) grown in GM17. NaCl was added to 0.5 M end concentration to part of the culture at A600=0.5 (open symbols); see Examples 3 and 5. N.B. In this specification the indication OD600 (optical density) is used instead of A600 (absorption).

FIG. 16.

Scheme of the construction of plasmid pNS3PR starting from plasmid pIR1PR and a fragment containing the rggL gene and the salt-inducible promoter, which was amplified by PCR using primers NS3-7 and NS3-8 (see Table 2 below) and pNS3 as template (see Example 3.1).

FIG. 17.

Optical density at 600 nm of LL108(pNS378)(squares) and LL108(pNS3AL3)(triangles) grown in GM17. NaCl was added to 0.5 M end concentration to part of the culture at A600=0.5 (open symbols); see Examples 4 and 5.

FIG. 18.

Figure 16:
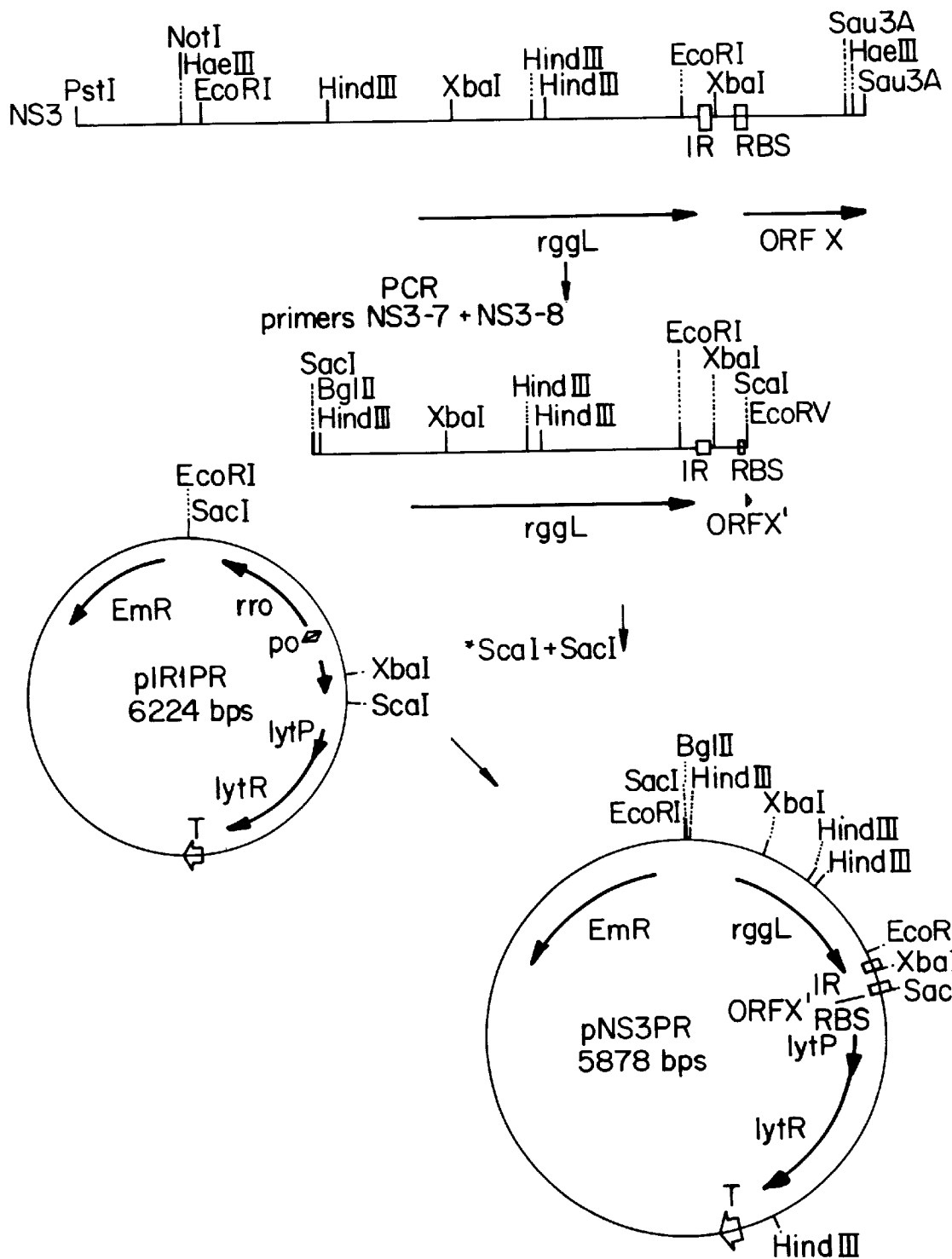

Scheme of the construction of plasmid pNS3AL3 starting from plasmids pAL10, pORI28 and the fragment also described in FIG. 16 (see Example 4.1).

FIGS. 19A-B.

(A) SDS-12.5% PAA gel stained with Coomassie Briliant Blue of supernatant samples of *L. lactis* cultures taken 6 hours after addition of NaCl.

(B) Renaturing SDS-12.5% PAGE showing cell wall hydrolase activity. Lanes: 1 and 2, LL108(pNS378); 3 and 4, LL108(pNS3PR); 5 and 6, LL108(pNS3AL3); 1, 3 and 5, no NaCl added; 2, 4 and 6, plus NaCl. Molecular masses (in kilodaltons) of marker proteins are shown on the left. The arrow on the right indicates the position of pre-AcmA (see Example 5).

FIG. 20.

PepXP activity in supernatants of cultures of MG1363acmAΔ1 (pVE6007;pNS3PR), circles, MG1363acmAΔ1 (pVE6007;pNS3AL3), triangles, and MG1363acmAΔ1(pVE6007;pNS378), squares.

At t=0 (optical density at 600 nm=0.5) NaCl was added to a final concentration of 0.5 M (closed symbols) or 0.1 M (open symbols) to induce the expression of lytPR, acmA, or lacZ, respectively (see Example 5.1).

FIG. 21.

PepXP activities in the supernatant fractions (black bars) and in the fractions obtained after hypo-osmotic wash of the cells (superimposed grey bars) of MG1363acmAΔ1 (pVE6007) carrying pNS378, pNS3PR, pNS3AL3 or pGKAL1. Cells were induced with 0.025, 0.05, 0.1, 0.25, or 0.5 M of extra NaCl at an optical density of the cultures of 0.5 at 600 nm. As a negative control M17 containing 0.004 M NaCl was used. PepXP levels were determined two days after induction (see Example 5.1).

FIG. 22.

Gene organization of the NS3 locus. Lollypop, inverted repeat; P, promoter. Relevant restriction enzyme sites are indicated (see Example 6). The black arrows indicate the positions of lacZ fusions in the chromosome of the indicated strains (lacZ not drawn to scale). The total sequences of the gadR, gadC and gadB genes are given in FIG. 29 and SEQ. ID. NO: 21.

FIGS. 23A-C.

Alignment of the deduced translation products of gadC from *L. lactis* (SEQ. ID. NO: 24) and gadC from *S. flexneri* (Waterman and Small, 1996; ref. 47). Asterisks, identical amino acids; periods, similar amino acids. Putative membrane spanning domains are double underlined. Residues of a putative glutamate binding box are shown in a frame (see Example 6).

FIGS. 24A-B.

Alignment of GadB from *L. lactis* MG1363, and glutamate decarboxylase from Synechocystis sp. strain PCC6803 (Kaneko et al., 1996; ref. 44). Asterisks, identical amino acids; periods, similar amino acids (see Example 6).

Figure 25A:
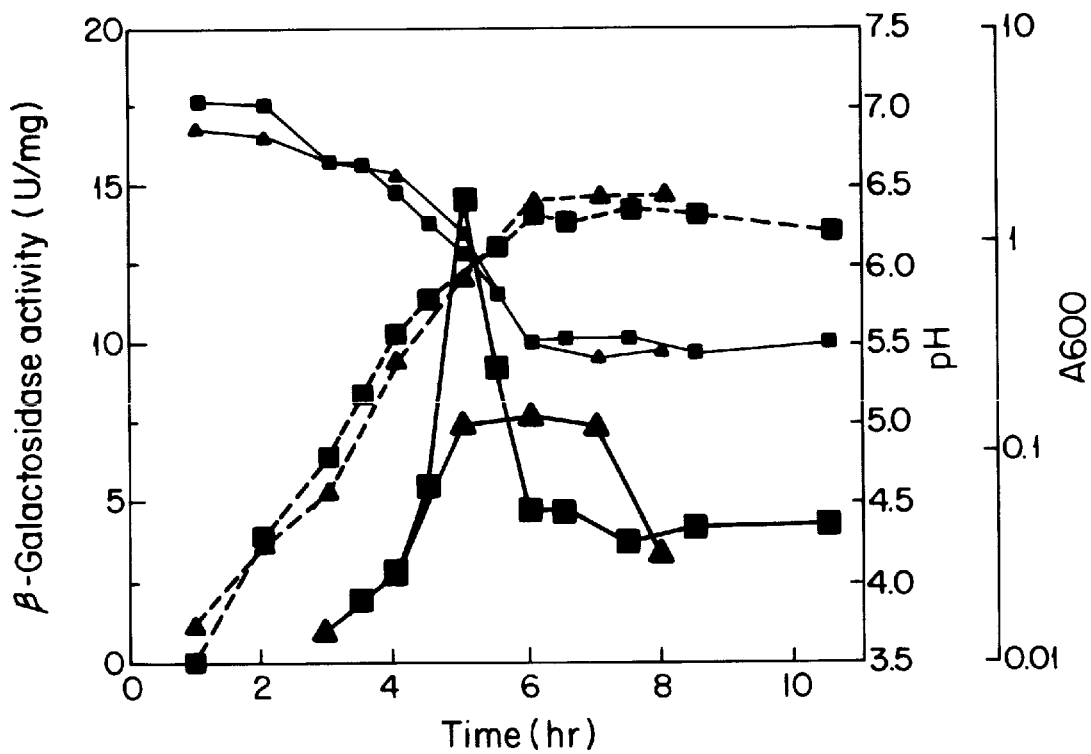
Figure 25B:
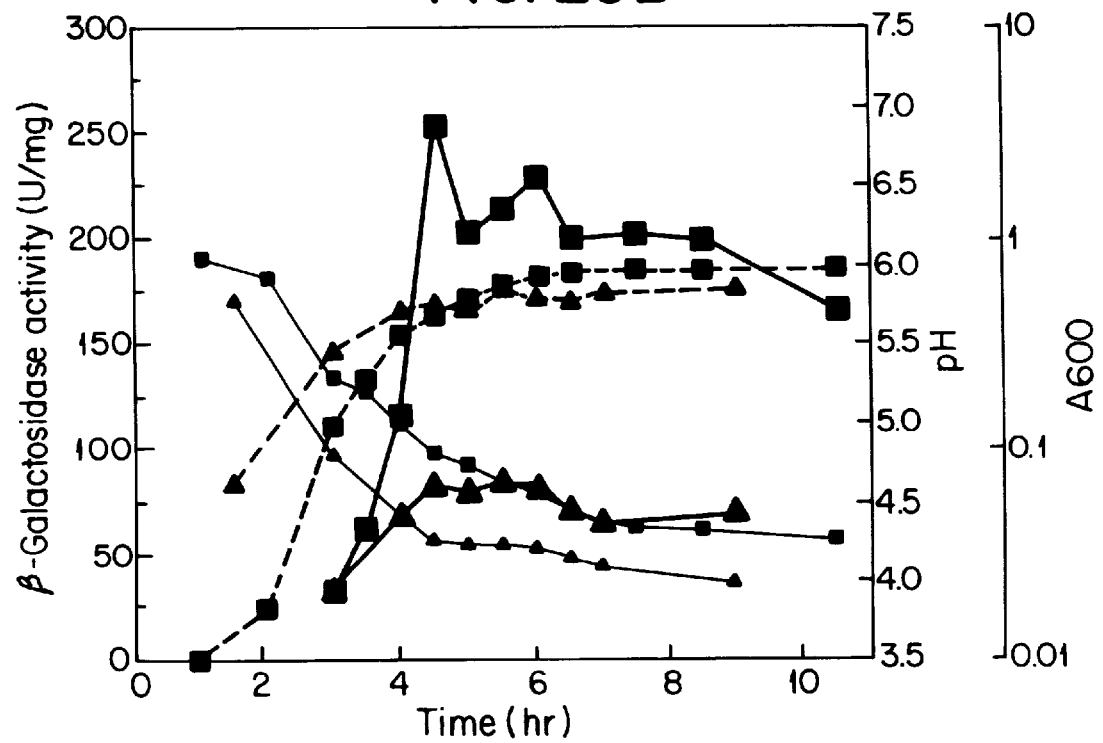

FIGS. 25A and 25B.

pH and glutamate-dependent expression of gadC::lacz. Strain NS3 was grown in mM17 medium with (A) or without (B) 2% β-glycerophosphate. β-galactosidase activity was followed during growth (fat solid lines) either in the presence of 0.3 M NaCl (▲) or in the presence of 0.3 M NaCl plus 50 mM glutamic acid (■). Note that the scale of the left Y-axis in A and B is different. The optical density and pH of the cultures are indicated with dotted lines and thin lines, respectively (see Example 6).

FIG. 26.

Schematic representation of the acid resistance mechanism in lactococci, involving the decarboxylation of glutamate to γ-aminobutyrate (see Example 6).

FIG. 27.

Schematic representation of plasmids pNS3i4 (see Example 1.4.1), pNS3i5, pNS3i6 and pNS3i7 (for the latter three plasmids see Example 6).

FIG. 28.

Schematic representation of plasmid pORI19S (see Example 1.6.1).

FIGS. 29A-Q.

Total nucleotide sequences of the gadR, gadC and gadB genes (see also SEQ. ID. NO: 21).

DETAILED DESCRIPTION OF THE INVENTION

The invention provides a salt-inducible promoter derivable from a lactic acid bacterium, in isolation from the coding sequence which is normally controlled by said promoter in a wild-type lactic acid bacterium. Such a salt-inducible promoter was found during the work resulting in the invention and described below in the Examples. This work yielded inter alia a DNA fragment originating from chromosomal DNA of L. lactis MG1363 in which a salt-inducible promoter appeared to be present. The nucleotide sequence of this DNA fragment is given in FIGS. 6A-H and SEQ. ID. NO: 10.

Deletion analysis described in Example 1.3–1.3.1 revealed that salt-induction of the lacZ gene is still possible, when about 1 kb of genomic DNA isolated from L. lactis M1363 is present in front of the lacZ gene (which DNA is present in a HindIII-Sau3A fragment; see polynucleotide 1476-2426 in FIGS. 6D-G). With shorter DNA fragments, i.e. containing only 540 bp (see the EcoRI-Sau3A fragment containing polynucleotide 1882-2422 in FIGS. 6E-G) or only 440 bp (see the XbaI-Sau3A fragment containing polynucleotide 1982-2422 in FIGS. 6E-G) upstream of the fusion point of the lacZ gene with the genomic DNA isolated from L. lactis M1363, salt-induction was only weak or not possible at all, respectively. Therefore, an essential part of this salt-inducible promoter seems to be the polynucleotide 1482-1925 of SEQ. ID. NO: 10, which is part of the HindIII fragment described in Example 1.3.1 below and comprises the 3' part of a gene indicated with rggL in FIGS. 6A-H up to and including the stop codon. It is believed that this part of the rggL gene can be combined with any promoter capable of driving expression of a structural gene in a lactic acid bacterium, but it is preferred that this part of the rggL gene is combined with the real promoter found in the genomic clone, which is the polynculeotide 1926-2000 including an inverted repeat (polynucleotide 1926-1967 of FIG. 6E) instead of a −35 region and including the −10 region (polynucleotide 1987-1992 of FIG. 6E), and with the further part of DNA upstream of the ORFX-encoding gene (see polynucleotide 2001-2068 of FIGS. 6E-F).

Thus a preferred essential part comprises the polynucleotide 1482-2068 of SEQ. ID. NO: 10.

Since the best results were obtained with the about 2.4 kb PstI-Sau3A DNA fragment described in Example 1.4, which contains the full rggL gene preceded by and under control of its own promoter, a salt-inducible promoter comprising the polynucleotide 1-2068 of SEQ. ID. NO: 10 is more preferred, and still more preferred is the use of the full 2.4 kb fragment, thus a salt-inducible promoter, which additionally comprises part of the ORF X gene together forming polynucleotide 1-2426 of SEQ. ID. NO: 10.

In addition to the various parts of the promoter just mentioned it is envisaged that also modifications thereof can be used according to the invention. Thus the invention also provides a modification of a salt-inducible promoter according to the invention or an essential part thereof, which comprises a DNA sequence essentially corresponding to a polynucleotide selected from the group consisting of

| | |
|---|---|
| (a) | polynucleotide 1482–1925 of SEQ. ID. NO: 10 followed by a promoter functional in a lactic acid bacterium, |
| (b) | polynucleotide 1482–2068 of SEQ. ID. NO: 10, |
| (c) | polynucleotide 1–2068 of SEQ. ID. NO: 10, and |
| (d) | polynucleotide 1–2426 of SEQ. ID. NO: 10. |

"Essentially corresponding to a polynucleotide" is understood as to include genetic variants, such as hybrid sequences containing a salt-inducible promoter or part thereof coupled to other homologous or heterologous DNA sequences including regulatory regions, and sequences containing modifications of the salt-inducible promoter or sequences having mutations, including mutations which still allow hybridization with the complementary strand of the salt-inducible promoter and genetic variants thereof, while still being capable of exerting the promoter function.

It is believed that the rggL gene, or in fact the rggL polypeptide, plays an important role in the effectiveness of the salt-inducible promoter present in the genome of L. lactis MG1363, isolated by the present inventors and used to transform other lactic acid bacteria in order to give them other desirable properties. But it is further believed, that not only the rggL gene indicated by polynucleotide 1095-1925 of SEQ. ID. NO: 10 will be functional in this respect, but also other DNA fragments encoding the same polypeptide, and even other DNA fragments encoding a modification of such rggL polypeptide still having the same or a similar functionality. Thus an aspect of the present invention is a DNA fragment capable of regulating a salt-inducible promoter active in a lactic acid bacterium, which comprises the polynucleotide 1095-1925 of SEQ. ID. NO: 10, or a modification thereof that (a) encodes the same polypeptide as said polynucleotide 1095-1925, or (b) encodes a modification of such polypeptide still having essentially the same regulating capacity.

A further aspect of the invention is a recombinant vector comprising a salt-inducible promoter or an essential part thereof as described above, or a DNA fragment capable of regulating a salt-inducible promoter active in a lactic acid bacterium as described above in combination with a DNA fragment selected from the group consisting of a DNA fragment containing the polynucleotide 1926-2000 of SEQ. ID. NO: 10 and modifications thereof still having essentially the same promoting capacity.

The invention also provides a transformed lactic acid bacterium comprising a salt-inducible promoter or an essential part thereof as described above, or a DNA fragment capable of regulating a salt-inducible promoter active in a lactic acid bacterium as described above in combination with a DNA fragment selected from the group consisting of a DNA fragment containing the polynucleotide 1926-2000 of SEQ. ID. NO: 10 and modifications thereof still having essentially the same promoting capacity. The promoter, essential parts thereof and other DNA fragments as described above are preferably present in the chromosome of the lactic acid bacterium, but they can also be present as part of a plasmid that can be maintained during growth of the lactic bacterium.

The lactic acid bacterium containing a salt-inducible promoter according to the invention either can be the natural host from which the salt-inducible promoter is derivable, or it can be a different lactic acid bacterium. If both the lactic acid bacterium and the salt-inducible promoter applied according to the invention are the same as in the natural situation, the lactic acid bacterium is transformed by incorporating one or more DNA fragments, or the salt-inducible promoter, originating from a lactic acid bacterium, is used in isolation from the coding sequence which is normally controlled by said promoter in a wild-type lactic acid bacterium.

Further the invention provides a process for the production of a desired protein by a transformed lactic acid bacterium, whereby the gene encoding said desired protein or a precursor thereof is expressed under control of an inducible promoter, characterised in that the promoter is a salt-inducible promoter or an essential part thereof according to the invention or a DNA fragment capable of regulating a salt-inducible promoter active in a lactic acid bacterium as described above in combination with a DNA fragment selected from the group consisting of a DNA fragment containing the polynucleotide 1926-2000 of SEQ. ID. NO: 10 and modifications thereof still having essentially the same promoting capacity. Preferably the transformed lactic acid bacterium is food-grade due to the use of food-grade DNA sequences and/or removal of non-food-grade DNA sequences.

For some embodiments it is desirable that the desired protein is secreted by the lactic acid bacterium due to the presence of a DNA fragment fused to the gene encoding the desired protein and effecting secretion of the desired protein or a precursor thereof.

A process according to the invention using a salt-inducible promoter for the expression of a desired gene can be used in a fermentation process, in which the desired protein is a lytic protein causing lysis of the bacterial cells so that the contents of the cells can be released, or in a fermentation process, in which the desired protein is an enzyme involved in the in situ production of secondary metabolites as flavour or taste ingredients. Examples of end products include dressings and water-containing spreads, as well as sausages and sour dough.

TABLE 1

Bacterial strains and plasmids

| Strain or plasmid | Relevant characteristics | Reference or source |
|---|---|---|
| Strains | | |
| *L. lactis* | | |
| MG1363 | Plasmid-free derivative of NCDO712 | ref. 5 |
| MG1363acmA Δ1 | AcmA⁻ derivative of MG1363 | ref. 31 |
| LL108 | repA$^\pm$ derivative of MG1363, Cm$^r$ | This work and ref. 40 |
| LL302 | repA$^\pm$ derivative of MG1363 | This work and ref. 40 |
| NS3 | NS3::lacZ, Em$^r$ | This work |
| MGNS3i3 | ΔrggL derivative of MG1363, Sp$^r$ | This work |
| *E. coli* | | |
| MC1000 | F⁻, ara D139 (ara ABC-leu)7679, galU, galK, LacX74, rspL, thi | ref. 7 |
| EC1000 | repA$^\pm$ derivative of MC1000, Km$^r$, carrying a single copy of the pWV01 repA gene in the glgB gene | This work and ref. 39 |
| EC101 | repA$^\pm$ derivative of JM101, Km$^r$ | ref. 37 |
| NM522 | supE, thi, Δ(lac-proAB), Δhsd5 (r⁻, m⁻), [F';proAB,lacI$^q$Z ΔM15] | ref. 6 |
| Plasmids | | |
| pMG60 | Em$^r$, fusion of promoter 32 with lacZ | ref. 24 |
| pORI28 | Em$^r$, Ori$^+$ of pWV01, Rep⁻ | This work and ref. 40 |
| pLS28 | Em$^r$, 'lacZ of pMG60 in pORI28 | This work |
| pKL10 | Em$^r$, carrying the pBR322 ori | ref. 17 |
| pLS10 | pKL10, carrying the 5'-end of lacZ from pMG60 | This work |
| pLS11 | pKL10, carrying the complete *E. coli* lacZ gene | This work |
| pUC7K | Ap$^r$, Km$^r$ | ref. 11 |
| pBSK + | Amp$^r$, α-lacZ | ex Stratagene |
| pLS12Km | Em$^r$, Km$^r$, pLS11 carrying the multiple cloning site of pBSK + | This work |
| pLS12 | Em$^r$, derivative of pLS12Km | This work |
| pLS13 | Em$^r$, promoterless lacZ | This work |
| pORI13 | Promoterless lacZ, Em$^r$, Ori$^+$ of pWV01, Rep⁻ | This work |
| pVE6007 | Cm$^r$, pWV01 derivative encoding a temperature sensitive Rep protein | ref. 28 |
| pNS3 | Em$^r$, NS3::lacZ, carries a 10 kb Sau3A chromosomal DNA fragment | This work |
| pNS3b | Em$^r$, NS3::lacZ, carries a 1.0 kb HindIII-Sau3A chromosomal DNA fragment | This work |
| pNS3d | Em$^r$, NS3::lacZ, carries a 2.5 kb PstI-Sau3A chromosomal DNA fragment | This work |
| pNS3e | Em$^r$, NS3::lacZ, carries a 540 bp EcoRI-Sau3A chromosomal DNA fragment | This work |
| pNS3f | Em$^r$, NS3::lacZ, carries a 440 bp XbaI-Sau3A chromosomal DNA fragment | This work |
| pNS378 | Em$^r$, NS3::lacZ, carries a 1280 bp PCR fragment amplified with NS3-7 and NS3-8 | This work |
| pUC19 | Ap$^r$, lacZ' | ref. 8 |
| pNS3I | Ap$^r$, pUC19 with a 401 bp EcoRI-HindIII fragment of pNS3b | This work |
| pNS3II | Ap$^r$, pUC18 with a 784 bp XbaI fragment of pNS3 | This work |
| pNS3III | Ap$^r$, pUC18 with a 470 bp XbaI fragment of pNS3 | This work |
| pNS3IV | Ap$^r$, pUC18 with a 604 bp HindIII fragment of pNS3 | This work |
| pNS3V | Ap$^r$, pUC18 with a 743 bp EcoRI-XbaI fragment of pNS3 | This work |
| pNS3VI | Ap$^r$, pUC19 with a 833 bp HindIII-PstI fragment of pNS3 | This work |
| pORI19 | Em$^r$, α-lacZ, Ori$^+$ of pWV01, Rep⁻ | ref. 37 |
| pNS3i4 | Em$^r$, pORI19 with a 561 bp Sau3A-XbaI chromosomal DNA fragment | This work |
| pORI19S | Sp$^r$, α-lacZ, derivative of pORI19 in which the StuI-XmnI fragment was replaced by an EcoRV-SmaI fragment carrying the Spectinomycin resistance gene | Lab. collection |
| pNS3i3 | Sp$^r$, internal XbaI-HindIII fragment of rggL in pORI19S | This work |
| pIR1PR | Em$^r$, phage r1-t lytPR fused to r1-t regulatory cassette | ref. 35 |
| pNS3PR | Em$^r$, NS3::lytPR | This work |
| pAL10 | Ap$^r$, acmA ΔSacI | ref. 34 |
| pAL101 | Ap$^r$, derivative of pAL10, BglII sites deleted | This work |
| pAL102 | Ap$^r$, Em$^r$, Ori$^+$, derivative of pAL101 | This work |
| pNS3AL3S | Em$^r$, NS3::acmA ΔSacI, derivative of pAL102 | This work |
| pNS3AL3 | Em$^r$, NS3::acmA | This work |

Still another process which can benefit from the presence of a salt-inducible promoter in a microorganism is a fermentation process, in which the desired protein is a protein having a function in a cheese production process, such as chymosin or a precursor thereof, or an enzyme involved in cheese flavour formation.

The invention is exemplified by the following Examples 1–6. preceded by a description of the materials and methods that were used.

MATERIALS AND METHODS

Bacterial Strains, Plasmids, and Growth Conditions

The bacterial strains and plasmids used in the work described are listed in Table 1 above.

*L. lactis* was grown at 30° C. in M17 medium, with 0.5% glucose; solidified M17 medium contained 1.5% agar. Erythromycin (Em) and chloramphenicol (Cm) were used at final concentrations of 5 µg/ml, spectinomycin (Sp) was used at 100 µg/ml. 5-Bromo-4-chloro-3-indolyl-β-D-galactopyranoside (X-Gal) was used at a final concentration of 0.008%.

*E. coli* was grown in TY broth at 37° C. with vigorous agitation or on TY medium supplemented with 1.5% agar. Ampicillin (Ap) and Em were used at 100 µg/ml, Sp at 50 µg/ml.

Molecular Cloning Techniques

DNA and RNA techniques were performed essentially as described by Sambrook c.s. (see ref. 16). DNA was introduced by electrotransformation in *E. coli* (see ref. 19; E. R. Zabarovsky & G. Winberg; 1990) and in *L. lactis* (see ref. 15; H. Holo & I. F. Nes; 1989). DNA sequencing was done on double-stranded plasmid DNA by the dideoxy chain-termination method (see ref. 4; F. Sanger c.s.; 1977) and the T7 sequencing kit (Pharmacia LKB Biotechnology AB, Uppsala, Sweden) according to the manufacturer's instructions.

Several oligonucleotides prepared and used in the work described are listed in Table 2.

TABLE 2

Oligonucleotides used in this work

| Name | Nucleotide sequence (5' to 3') | |
|---|---|---|
| NS3-1 | CATTGAGATA ATCAGATAC (19) | SEQ. ID. NO: 1 |
| NS3-2 | GCAGAGATTG GGGAAG (16) | SEQ. ID. NO: 2 |
| NS3-5 | GGGGCCCTCT CTTATGTGTT AAATTTTCAG GCGC (34) | SEQ. ID. NO: 3 |
| NS3-6 | ATATCGTTCA CGTTTTCC (18) | SEQ. ID. NO: 4 |
| N53-7 | GCGATATCCA GTACTTCATC ATACCTCCTT ATATTTATGA TTG (43) | SEQ. ID. NO: 5 |
| NS3-8 | GCGAGCTCAG ATCTGAGCGT TGTATAAGCT TTTATGTCTT TC (42) | SEQ. ID. NO: 6 |
| NS3-9 | GTTTGACTGA CCCAAC (16) | SEQ. ID. NO: 7 |
| NS3-10 | CCGCTTCAAT GGTTTTG (17) | SEQ. ID. NO: 8 |
| NS3-11 | CAGTCAAAAC CATTGAAGCG GTTAATGCGA AAAAACCG (38) | SEQ. ID. NO: 9 |

The oligonucleotides were synthesized with an Applied Biosystems 392A DNA synthesizer (Applied Biosystems Inc. Foster City, Calif.). DNA sequences were analyzed with the PC/Gene sequence analysis program (IntelliGenetics Inc., Geneva, Switzerland). Protein homology searches against the Genbank were carried out using the FASTA program (see ref. 12; W. R. Pearson & D. J. Lipman; 1988). Protein sequence alignments were carried out with the PALIGN program of PC/Gene using the structure genetic matrix or with the CLUSTAL program, both with standard settings.

In this specification the following endonuclease restriction sites are used:

| giving staggered ends | | giving blunt ends | |
|---|---|---|---|
| ApaI | GGGCC↓C | EcoRV | GAT↓ACT |
| BamHI | G↓GATCC | PvuII | CAG↓CTG |
| BglII | A↓GATCT | ScaI | AGT↓ACT |
| BssHII | G↓CGCGC | SmaI | CCC↓GGG |
| ClaI | AT↓CGAT | SspI | AAT↓ATT |
| EcoRI | G↓AATTC | StuI | AGG↓CCT |
| HindIII | A↓AGCTT | XmnI | GAANN↓NNTTC |
| MluI | A↓CGCGT | | |
| NotI | GC↓GGCCGC | | |
| PstI | CTGCA↓G | | |
| SacI | GAGCT↓C | | |
| SalI | G↓TCGAC | | |
| Sau3A | ↓GATC | | |
| SpeI | A↓CTAGT | | |
| SphI | GCATG↓C | | |
| TaqI | T↓CGA | | |
| XbaI | T↓CTAGA | | |
| XhoI | C↓TCGAG | | |

β-Galactosidase Assays

Cell extracts were prepared from exponentially growing cultures. β-Galactosidase activity was determined as described by Miller (see ref. 2; J. H. Miller; 1972). Protein concentrations in the cell extracts were determined by the method of Bradford (see ref. 3; M. M. Bradford; 1976) with bovine serum albumin as a standard.

EXAMPLE 1

Isolation of a Salt-inducible Promoter

Several plasmids and transformed strains had to be prepared before a salt-inducible promoter could be isolated. Thus first some helper strains were constructed containing the repA gene of pWV01, i.e. *L. lactis* LL108 and *L. lactis* LL302 (see 1.1.2 below) and *E. coli* EC1000 (see 1.1.1 below). This work is based on the technology described in EP-A1-0 487 159 (see ref. 26; Unilever N.V./PLC (C. J. Leenhouts c.s.); 1992). Subsequently several plasmids were constructed:

plasmid pORI28 with plasmids pTC2, pUK24 and pORI24 as intermediates (see 1.1.3 below), plasmid pLS13 with plasmids pLS10, pLS11, pLS12 and pORI28 as intermediates (see 1.1.4 below), the promoter screening vector plasmid pORI13 with plasmids pORI28, pLS28 and pLS13 as intermediates using lactococcal helper strains LL108 and LL302 (see 1.1.5 below).

These plasmids carry the ORI$^+$ of pWV01 but lack the repA gene for the replication initiation protein. However, they can be replicated in the helper strains containing the repA gene of pWV01.

1.1 A Lactococcal Genome Bank in pORI13

To be able to assess expression of chromosomal genes, the promoter screening vector pORI13 was constructed (FIG. 1). To allow only transcriptional fusions one stop codon in each reading frame was present immediately upstream of the *E. coli* lacZ gene. The lacZ gene is preceded by lactococcal translation signals derived from ORF32 (see ref. 24; M. van de Guchte c.s.; 1991 and ref. 10; J. M. B. M. van der Vossen c.s.; 1987). Since plasmid pORI13 carries the ORI$^+$ of pWV01 but lacks the repA gene for the replication initiation protein, it can be used for Campbell-type integrations.

Random Sau3A fragments obtained from total chromosomal DNA of L. lactis MG1363, ranging in size from 1 to 10 kb, were cloned in the BamHI site of pORI13. With the ligation mixture 48 EC1000 transformants were obtained and checked for their plasmid content. About 73% of these contained pORI13 with a chromosomal insert while the remainder contained pORI13. The average insert size was 3.3 kb. The restriction enzyme digestion pattern was different for all 48 clones. Plasmid DNA was isolated from 2,460,000 pooled EC1000 transformants (see 1.1.6 below) and used to transform L. lactis MG1363(pVE6007). After the temperature-up shift to force integration of the pOR13 derivatives, 9000 $Em^r$ clones were obtained by plating on selective sucrose GM17 plates containing X-gal and 0.3 M NaCl at 37° C. for 16 hours resulting in 195 colonies that stained blue after prolonged incubation at 30° C. (see 1.1.7 below).

1.1.1 Construction of E. coli EC1000, Being a $repA^+$ Derivative of MC1000, $Km^r$, and Carrying a Single Copy of the pWV01 repA Gene in the glgB Gene The repA gene from pWV01 was introduced onto the chromosome of E. coli MC1000 as described for JM101 by Law c.s. (see ref. 37; J. Law c.s.; 1995). pKVB2 (see ref. 37 and ref. 11; J. A. K. W. Kiel c.s.; 1987) is a $Tc^r Km^r$ plasmid of 11.7 kb containing the origin of replication of pBR322. It carries the E. coli chromosomal glgB gene in which an internal 1.2 kb BamHI fragment was replaced by the $Km^r$ gene from the Streptococcus faecalis plasmid pJH1. The repA gene from pWV01, driven by the lactococcal consensus promoter P23, was taken as a HindIII-PvuII fragment from pUC23rep3 (see ref. 37 and ref. 22; K. J. Leenhouts c.s.; September 1991) and used to replace a 700-bp SmaI fragment within glgB without interrupting the $Km^r$ gene. The resultant plasmids pEC1 and pEC2 differ solely in the orientation of repA (see ref. 37; J. Law c.s.; 1995).

Plasmids pEC1 and pEC2 were used to transform E. coli JM101. Before plating on selective media the transformation mixtures were transferred for 30 generations in the absence of antibiotic and then plated on Km-containing plates. Colonies were tested for glycogen production. Non-glycogen producing colonies were transferred onto plates containing Km and Tc and onto plates containing Km alone. $Km^r TC^s$ colonies were found and were plasmid-free and contained repA integrated at the specific site on the chromosome. Confirmation of the $RepA^+$ nature of one of the strains (E. coli EC1000) was obtained by the successful transformation of this strain with an $ORI^+$ $RepA^-$ plasmid. This work will also be described in a publication by Leenhouts c.s. accepted by Mol. Gen. Genet. for publication in 1996 (see ref. 39; K. Leenhouts c.s.; 1996).

1.1.2 Construction of $RepA^+$ L. lactis Strains LL108 and LL302

Two integration plasmids carrying pWV01 repA, pKL15A and pUK30, were constructed.

Plasmid pKL15A is a derivative of the pBR322-based Campbell-type integration plasmid pHV60 (see ref. 14; K. J. Leenhouts; 1989) in which the repA gene from plasmid pUC23rep3 (see ref. 22; K. J. Leenhouts; September 1991) was inserted. Integration of pKL15A into the chromosome of L. lactis MG1363 by selection for chloramphenicol resistance resulted in L. lactis strain LL108 carrying approximately 15 tandem copies of the integration plasmid, as has been described earlier for similar plasmids (see ref. 14; K. J. Leenhouts; 1989).

The replacement-type integration vector pUKwas obtained by cloning the repA fragment of pUC23rep3 in the multiple cloning site of pUK29. The latter plasmid is a derivative of pUK21 (see ref. 23; J. Vieira & J. Messing; 1991) and carries the Em resistance gene of pUC19E (see ref. 17; K. J. Leenhouts; 1990) in the XhoI site, the 3'-end of the L. lactis pepXP gene (see ref. 20; B. Mayo c.s.; 1991) as a 1.5 kb XbaI fragment in the XbaI site, and the 5'-end of pepXP as a 1.5 kb SpeI-MluI fragment in the BglII and SphI sites. Plasmid pUK30 was used in a two-step gene-replacement strategy (see ref. 21; K. J. Leenhouts c.s.; August 1991) for transforming L. lactis MG1363 yielding L. lactis strain LL302. This strain contained one copy of pWV01 repA inserted in the pepXP gene. Both strain LL302 and strain LL108 allow the replication of pWV01-based vectors which lack repA. This work will also be described in a publication by Leenhouts c.s. submitted for publication in 1996 (see ref. 40).

1.1.3 Construction of pORI28

The $Tc^r$ of PLS1 (see ref. 9; S. A. Lacks; 1986) was introduced in the SmaI site of pMTL25 (see ref. 13; S. P. Chambers c.s.; 1988) to produce pTC2. This Tc resistance gene was isolated from plasmid pTC2 as a 1.6 kb BamHI fragment and plasmid pUK21 (see above) was digested with XhoI. Prior to ligation of the two fragments, blunt ends were generated by Klenow enzyme treatment. The ligation resulted in pUK24, in which the $Tc^r$ gene is flanked by two XhoI restriction sites. The 1.7 kb SpeI fragment of pUK24 carrying the $Tc^r$ gene was treated with Klenow enzyme to create blunt ends. A 601 bp TaqI fragment of pWV01 which carries the plus origin of replication ($Ori^+$) but lacks the gene encoding the replication initiation protein (repA), was also treated with Klenow enzyme and both fragments were ligated, resulting in pORI24. The XhoI fragment of pORI24 carrying the $Tc^r$ gene was replaced by the $Em^r$ gene from plasmid pUC19E, located on a 1 kb SalI fragment, which resulted in plasmid pORI28. This work will also be described in a publication by Leenhouts c.s. accepted by Mol. Gen. Genet. for publication in 1996 (see ref. 39; K. Leenhouts c.s.; 1996).

1.1.4 Construction of pLS13

The lacZ gene of pMG60 (see ref. 24; M. van de Guchte c.s.; 1991) was cloned in pKL10 (see ref. 17; K. J. Leenhouts; 1990) in two steps. In the first step the 1250 bp SspI fragment ex pMG60, containing the 5'-end of lacZ gene and the lactococcal RBS of ORF32, was ligated with the Klenow treated XbaI site of pKL10. The resulting construct, PLS10, was restricted with HindIII, the HindIII sticky ends were made blunt and then the fragment was treated with ClaI. Subsequently, the resulting fragment was ligated with a ClaI-XmnI fragment of pMG60 containing the additional part of the lacZ gene, including a transcriptional terminator, resulting in pLS11.

Figure 2:
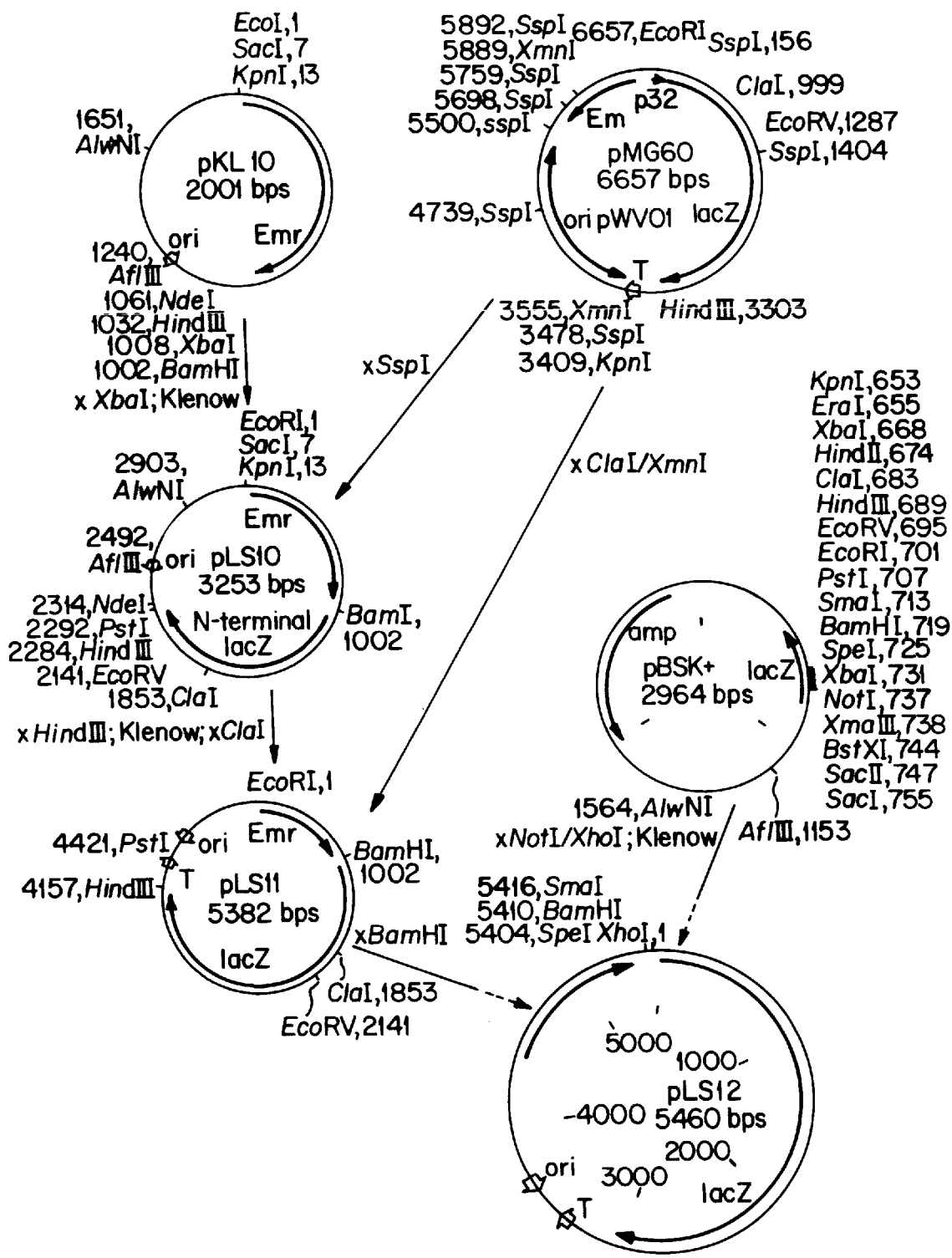

In the next step the multiple cloning site (mcs) of pBSK+ had to be inserted upstream of the RBS preceding the lacZ gene. To be able to select the mcs of pBSK+ it was marked by cloning a BamHI fragment from pUC7K, coding for a $Km^r$ gene, into the BamHI site of the mcs. Subsequently the mcs was excised from this plasmid using NotI and XhoI. The sticky ends were made blunt-ended and the fragment was ligated into the BamHI site (also made blunt-ended) of pLS11 in front of the lacZ gene. Finally the $Km^r$ gene was deleted using BamHI followed by self ligation. This resulted in the integration expression vector pLS12 (see FIG. 2).

Figure 3:
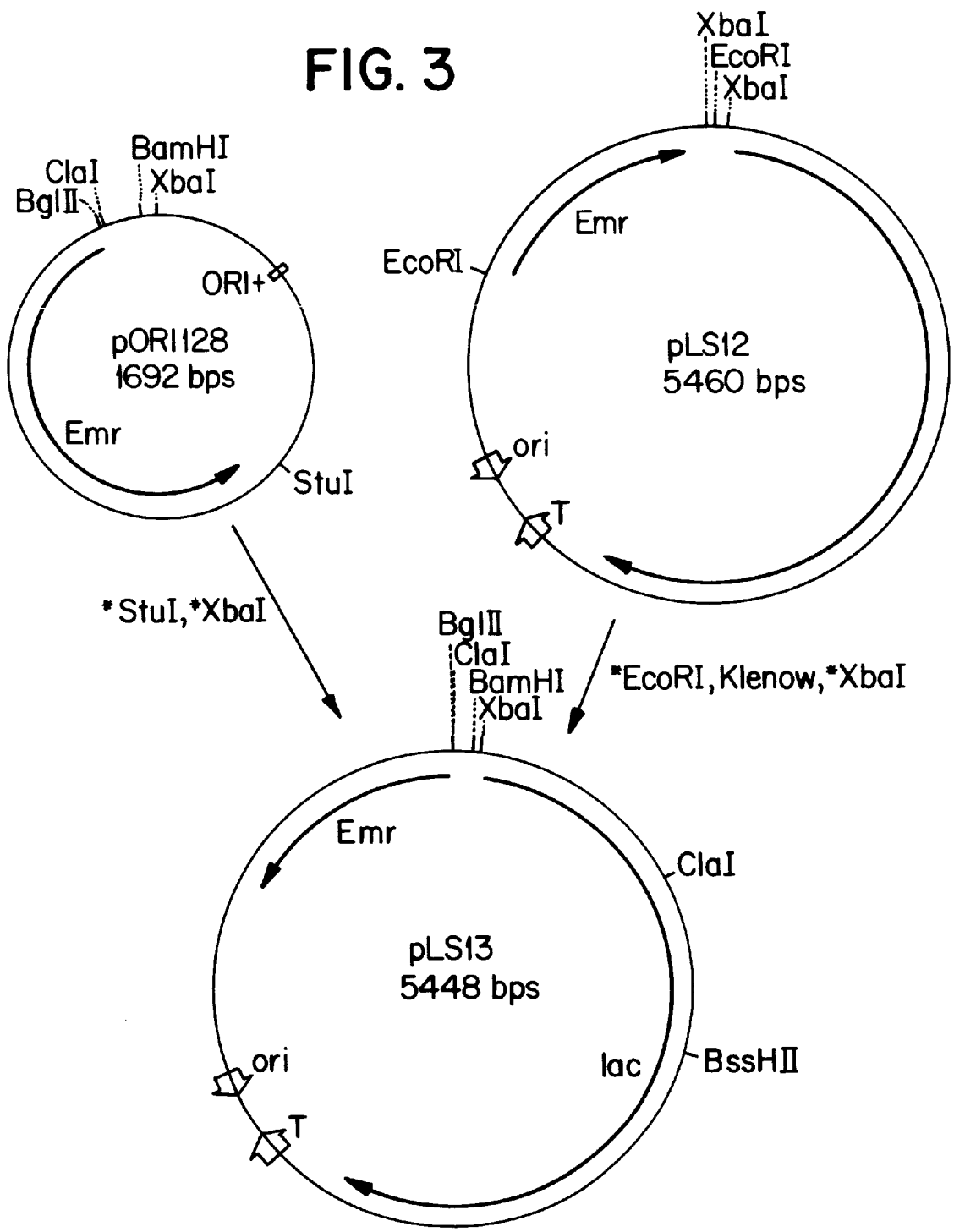

The erythromycin resistance gene of pLS12 was replaced by that from pORI28, including a multiple cloning site by isolating a StuI-XbaI fragment from pORI28. This fragment was ligated into pLS12 digested with EcoRI, made blunt-ended with Klenow enzyme and subsequently digested with XbaI. The resulting construct was designated pLS13 (see FIG. 3).

1.1.5 Construction of pORI13

For the construction of a promoter screening vector, the *E. coli* lacZ gene fused to lactococcal translation signals, as present on pMG60 (see ref. 24; M. van de Guchte c.s.; 1991), was used. The lacZ gene was placed in the integration vector pORI28 in two steps (see ref. 40; K. J. Leenhouts; submitted for publication 1996).

In the first step, a 2.5 kb ClaI-XmnI fragment of pMG60 was ligated in XbaI-ClaI linearized pORI28 of which the XbaI site was made blunt using Klenow. The ligation mixture was digested with EcoRI to prevent replication of pMG60 and used to transform the RepA+ lactococcal helper strain LL108. The resulting construct, pLS28, was cut with BglII and BssHII. The 5' end of the lacZ gene was liberated from pLS13 using the same restriction endonucleases. This 1.6 kb fragment was ligated to pLS28 and the ligation mixture was used to transform the RepA+ *L. lactis* helper strain LL302. The resulting plasmid was designated pORI13 (see FIG. 4).

1.1.6 Construction of a Genome Bank in pORI13

Total chromosomal DNA of *L. lactis* MG1363 was partially digested with Sau3A to obtain fragments ranging in size from 1 to 10 kb which were ligated to BamHI and alkaline phosphatase treated pORI13. The chromosomal fragments were ligated in the linearized pORI13. This ligation mixture was used to transform the RepA+ *E. coli* helper strain EC1000 (see 1.1.1 above). Transformants were collected from agar plates by pouring 2 ml of TY broth on each plate, and their plasmid DNA was isolated.

1.1.7 Integration of the Bank in the *L. lactis* Genome

The plasmid mixture obtained in the previous step was used to transform *L. lactis* MG1363(pVE6007). After electroporation, cells were suspended in recovery medium of 30° C. (see ref. 15; H. Holo & I. F. Nes; 1989). After 1.5 hour 5 µg/ml erythromycin was added and incubation at 30° C. was prolonged for 0.5 hour. Cells were shifted to 37° C. for 2 hours and then plated on sucrose (0.5 M) GM17 agar containing X-gal, erythromycin and 0.3 M NaCl. Incubation was at 37° C. for 24 hours and subsequently at 30° C. The recovery of pORI13 derivatives from the chromosome of selected integrants was done as described by Law c.s. (see ref. 37; J. Law c.s.; 1995).

1.2 Identification of a Clone Expressing lacZ in a Salt-dependent Way

Colonies expressing β-galactosidase in the presence of NaCl were transferred to GM17 agar plates with or without 0.5 M NaCl. Of the 195 selected blue colonies (see 1.1 above) 80 were white on the NaCl-free plates, indicating the absence of β-galactosidase expression. The intensity of the blue colour in the presence of NaCl was similar for all 80 clones. The integrated pORI13 derivatives in 5 of these clones, called NS1-NS5, were rescued and appeared to be identical at the restriction enzyme level. All five plasmids expressed the salt-dependent phenotype. One of these, pNS3 isolated from clone NS3, was selected for further characterization.

1.3 Deletion Analysis of the Genomic Region of NS3

Figure 5A:
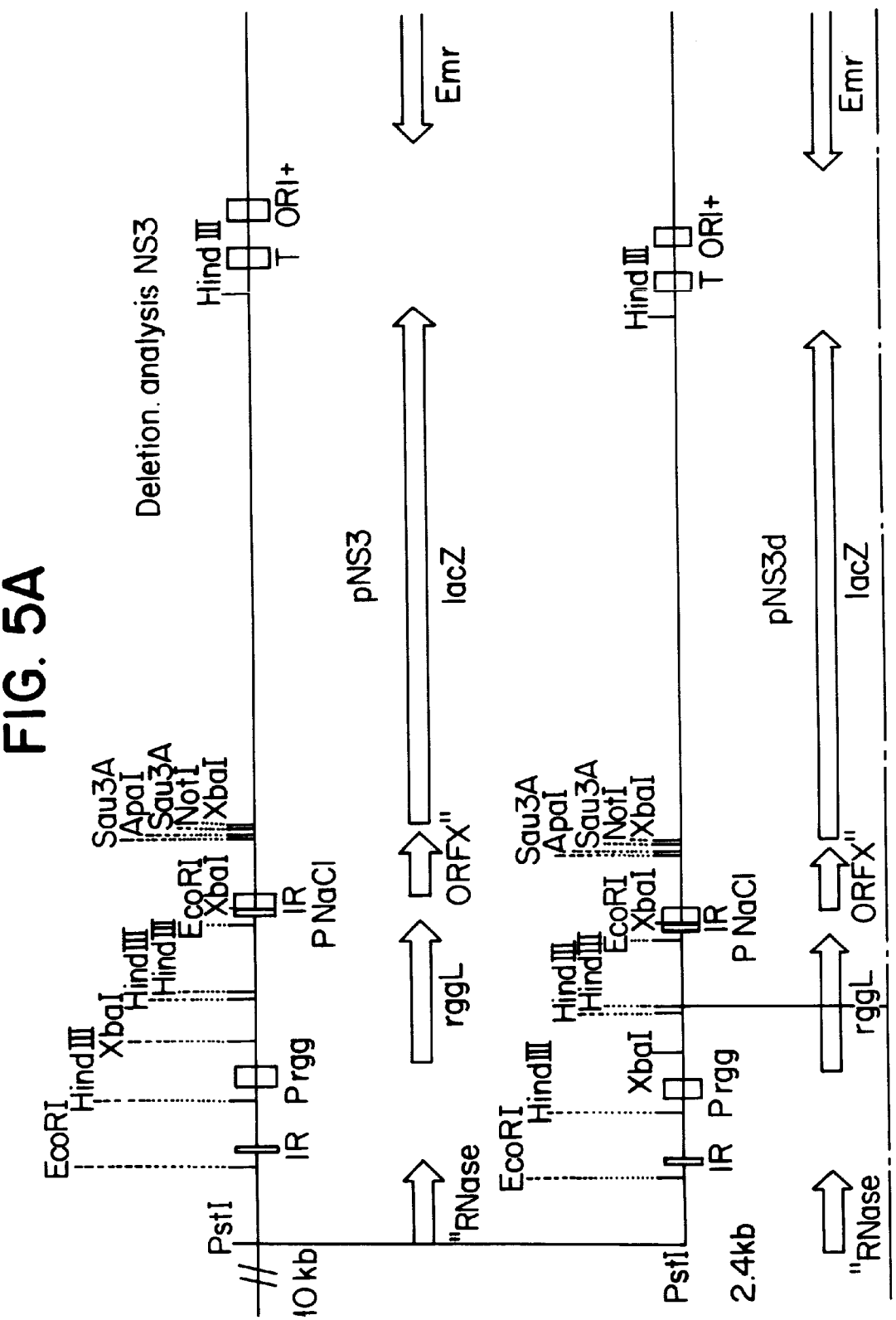
Figure 5B:
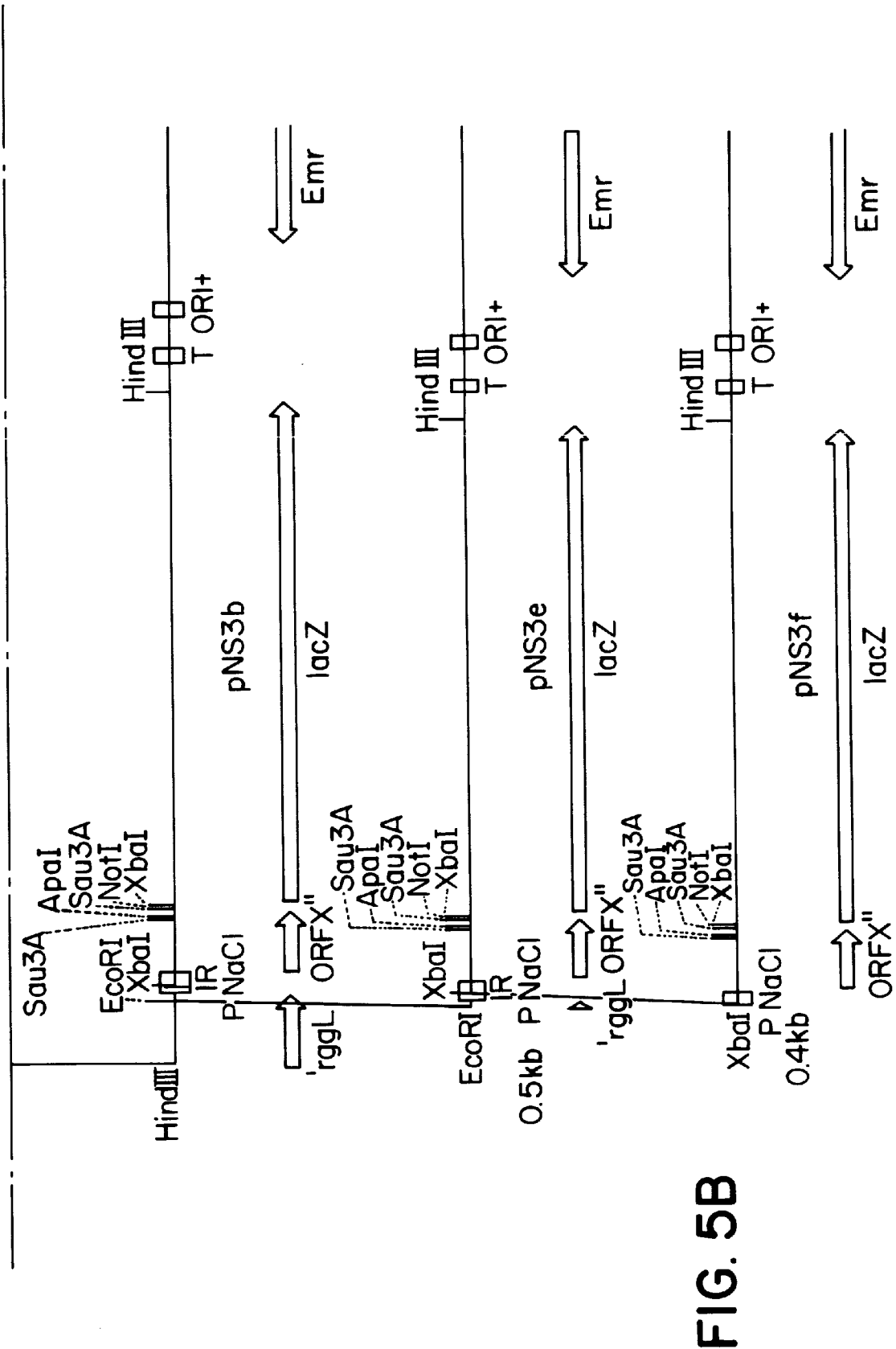

Restriction enzyme analysis of pNS3 revealed that about 10 kb of chromosomal DNA had been cloned. A number of restriction enzyme sites was used to map the salt-dependent promoter. A PstI deletion (pNS3d) showed that NaCl-dependent lacZ expression is linked to a 2.4 kb fragment directly upstream of the Sau3a site at the original fusion point (see FIG. 5 and position 2423 of FIG. 6G). A larger deletion, leaving 1.0 kb upstream of the fusion point (pNS3b), expressed β-galactosidase at a high level in the presence of NaCl but also at a low level in the absence of NaCl, whereas in the original clone β-galactosidase was not expressed in the absence of NaCl. Two other deletion constructs, carrying 540 bp (pNS3e) or 440 bp (pNS3f) fragments, showed a low level or no expression with NaCl, respectively. This indicates that the DNA region involved in NaCl-dependent gene expression is located between 1000 and 440 bp upstream of the fusion point (see FIGS. 5A-B).

1.3.1 Deletion Mapping of NS3

To localize sequences essential for salt-induced gene expression, a number of deletion derivatives of the pORI13 derivative recovered from the chromosome of NS3 (pNS3) were constructed. pNS3 was digested with HindIII yielding a fragment carrying lacZ and 1.0 kb of upstream lactococcal DNA. This fragment was ligated to a HindIII fragment of pORI13 carrying the Em resistance marker and the plus origin of replication of pWV01. The resulting construct, pNS3b, was isolated from *E. coli* EC1000. pNS3d was made by self-ligation of PstI digested pNS3 and carries 2.4 kb of chromosomal DNA fused to lacZ. The proper construct was obtained in *L. lactis* LL108. Plasmid pNS3e was obtained by using the self-ligation mixture of an EcoRI digest of pNS3 to transform *E. coli* EC1000 and carries an about 540-bp chromosomal DNA fragment upstream of lacZ. pNS3f was constructed by ligating the XbaI fragment from pNS3III (see 1.4.1 below) to the XbaI site of pORI13 and transformation of *E. coli* EC1000. pNS3f carries an about 440 bp chromosomal DNA fragment upstream of lacZ (see FIG. 5B).

1.4 Sequence Analysis of the NS3 Genomic Region

The 2.4 kb PstI-Sau3A fragment, as present in pNS3d, was sequenced (FIGS. 6A-H, which also gives the nucleotide sequence of the 561 bp Sau3A-XbaI fragment described in 1.4.1 below). This revealed a truncated open reading frame, orfX, that had been fused to lacZ. OrfX started about 360 bp upstream of the Sau3A site used for cloning and its putative truncated product shows homology with membrane proteins. The most extensive homology was found with two *E. coli* proteins with unknown function, YJEM and YGJI (Genbank entries U14003, and U18997, respectively). OrfX is preceded by a ribosome binding site (RBS). Upstream of orfX an ORF with a weak RBS could encode a protein of 276 amino acid residues (see SEQ. ID. NO: 10 and 11) with a calculated molecular weight of 32990. It shows homology to the *Streptococcus gordonii* rgg gene product (see SEQ. ID. NO: 12), which regulates expression of the glucosyl transferase gene (see ref. 27; M. C. Sulavik c.s.; 1992) and that of a partially sequenced ORF downstream of the *L. lactis* pip gene (see FIGS. 7A-B, SEQ. ID. NO: 13 and ref. 30; B. L. Geller c.s; 1993). In analogy to the *S. gordonii* gene the putative lactococcal regulator gene was named rggL. The overall identity between rggL and rgg is 24.3%, an additional 15.9% of the residues is similar. Directly downstream of rggL a 21 bp inverted repeat structure with a AG[25° C.] of −37.8 kcal/mol followed by a stretch of T residues might function as a rho-independent terminator. Upstream of rggL a third, incomplete, ORF is present that shows homology to several rnhB genes, encoding RNAse HIII (FIGS. 8A-B and SEQ. ID. NO: 14–17). The rnhB gene is followed by a rho-independent terminator-like structure with a AG[25° C.] of −10.6 kcal/mol suggesting that the rnhB gene is transcribed independently from rggL.

Figure 9:
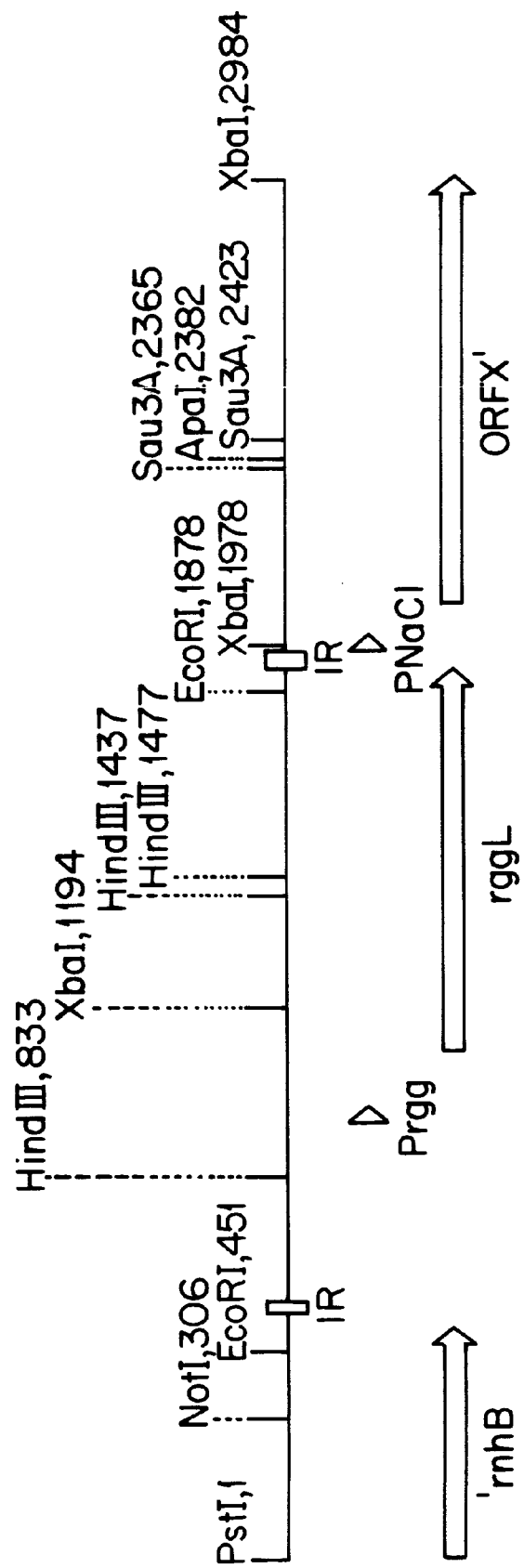

The genomic organization of the NS3 locus is given in FIG. 9, which shows that two rare restriction enzyme sites are present on the sequenced fragment, one for NotI (nucleotides 306–313, FIG. 6A) and one for ApaI (nucleotides 2382–2387, FIG. 6F), separated by only about 2070 bp. From a comparison with the genetic map of *L. lactis* MG1363 (see ref. 32; P. Le Bourgeois c.s.; 1995) it is clear that the NS3 locus is positioned between the ldh gene and the leu-ilv gene cluster.

1.4.1 Sequencing of the NS3 Locus

Figure 10:
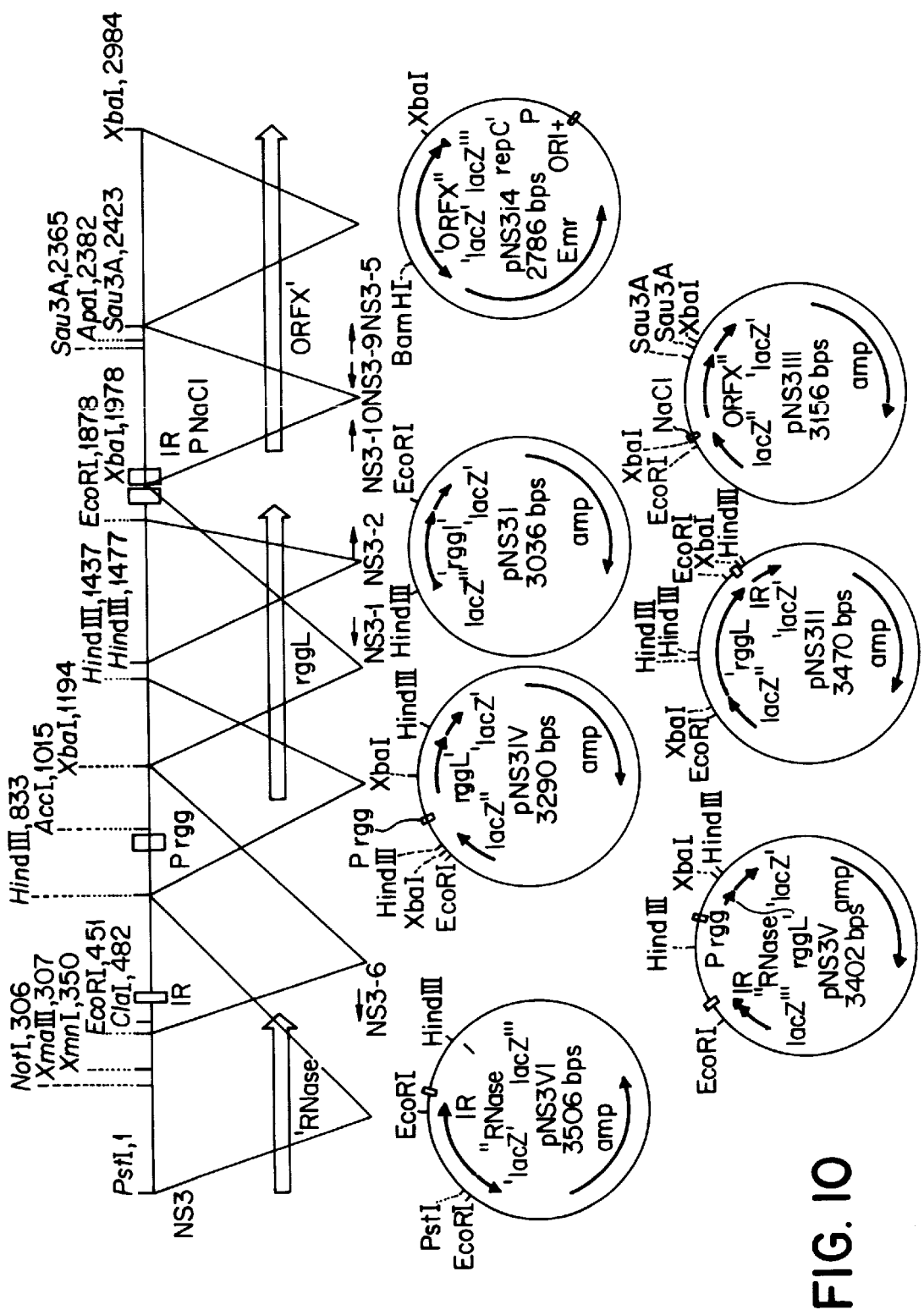

The 2.5 kb region upstream of the lacZ-fusion point in the chromosome of L. lactis NS3 was recovered into several subclones and sequenced. A 401 bp EcoRI-HindIII fragment from pNS3b was cloned in pUC19 and designated pNS3bI. 784 bp and 470 bp XbaI fragments from pNS3 were cloned in the XbaI site of pUC18, resulting in pNS3II and pNS3III, respectively. A 604 bp HindIII fragment from pNS3 was cloned in pUC18 and the plasmid was designated pNS3IV and a pUC18 derivative carrying the 743 bp EcoRI-XbaI fragment from pNS3 was called pNS3V. A fragment of 745 bp liberated from pNS3 with HindIII and PstI and cloned in pUC19 resulted in pNS3VI. E. coli NM522 was used as a cloning host for pUC18 or pUC19 constructs. A fragment located at the 3'-end of the chromosomal insert in pNS3 was amplified by inverse-PCR. Self-ligated circularized fragments of a chromosomal XbaI digest were used as a template and NS3-5 and NS3-11 were used as primers. A 561 bp Sau3A-XbaI fragment was isolated from the PCR fragment and ligated into XbaI-BamHI digested pORI19, resulting in pNS3i4 (see FIG. 27). DNA sequencing was done on double-stranded plasmid DNA by the dideoxy chain-termination method (see ref. 4; F. Sanger c.s.; 1977) and the T7 sequencing kit (Pharmacia LKB Biotechnology AB, Uppsala, Sweden) according to the manufacturer's instructions. The double stranded sequence was completed by using synthetic oligonucleotide primers NS3-1, NS3-2, NS3-6, NS3-9, and NS3-10 (see Table 2 above and FIG. 10).

1.5 Identification of a Salt-inducible Promoter Structure in NS3

On the basis of the deletion studies and the nucleotide sequence, an NaCl-dependent start point of transcription was expected in the 100 bp region between the inverted repeat and the start codon of orfX. A primer extension was carried out on RNA isolated from LL108(pNS3d) grown in the absence and presence of 0.5 M NaCl. Using primer NS3-11 transcription was found to start at an A residue 68 bp upstream of the AUG start codon of orfX (position 2001, FIG. 6E). No primer extension product was obtained with RNA of cells grown in the absence of NaCl. 9 bp upstream of the transcription start site a −10 hexanucleotide was identified that differs in only one nucleotide from the consensus sequence (see ref. 25; M. van de Guchte c.s.; 1992). Further upstream no −35 like hexanucleotide could be discerned. Instead, 17 bp upstream of the −10 hexanucleotide the inverted repeat is located, suggesting a role for this structure in gene expression.

1.5.1 RNA Analysis

RNA was isolated from exponentially growing L. lactis cultures (optical density at 600 nm of 0.5) with or without 0.5 M NaCl as previously described (see ref. 29; M. van Asseldonk; 1993). Northern hybridizations were done at 40° C. in a buffer containing 50% formamide, 7% SDS, 2% blocking reagent (Boehringer, Mannheim, Germany), 5×SSC, 50 mM sodium phosphate pH 7, and 0.1% N-lauryl sarcosine. A 470 bp XbaI fragment of pNS3III was used as a probe and labeled with [$\alpha^{32}$P-dCTP]. A synthetic oligonucleotide (NS3-11) complementary to the mRNA (position +96 to +133 downstream of the transcription start point) was used for primer extension. Twenty five nanogram of primer were added, to 5 μg of RNA in a reaction mixture containing dCTP, dGTP, dTTP and $\alpha$-$^{35}$S-dATP and cDNA was synthesized using AMV reverse transcriptase (Boehringer, Mannheim, Germany). After 10 minutes incubation at 42° C. an excess cold dATP was added and incubation was prolonged for another 10 minutes at 42° C. The product was analyzed on a sequencing gel next to a sequence reaction with the same primer, providing a size marker.

1.6 RggL Functions as an Activator

Figure 11:
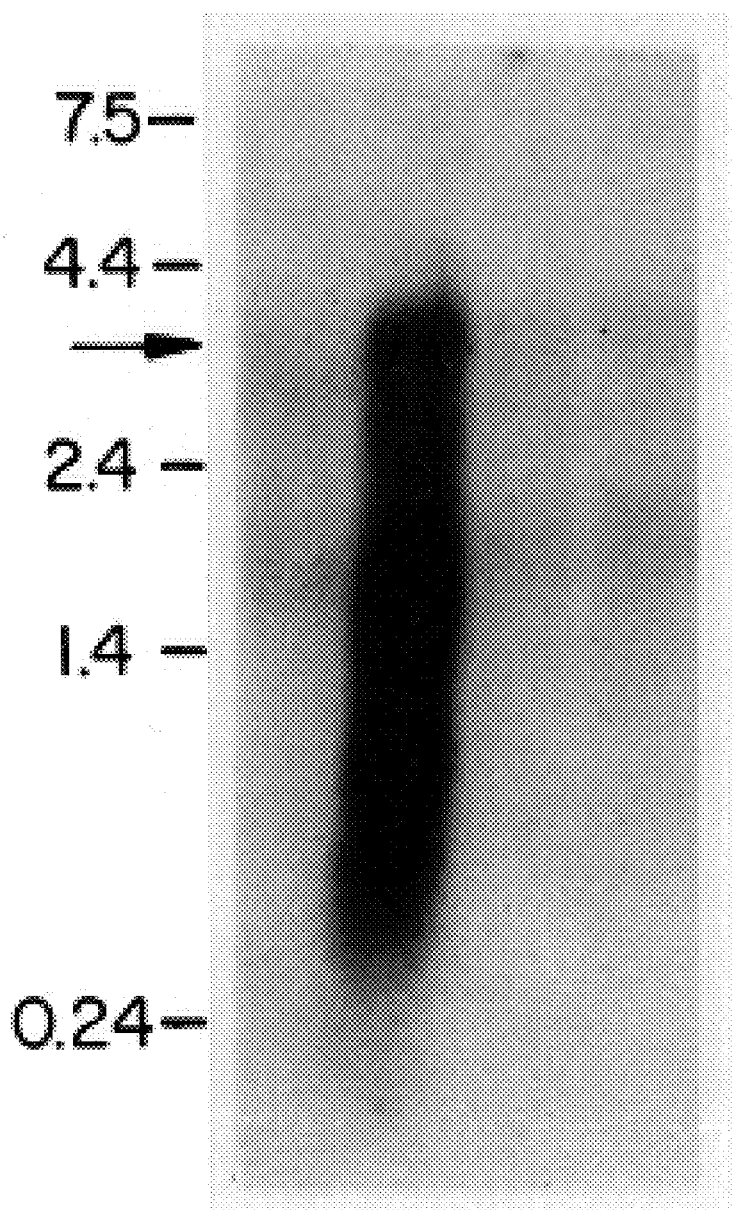

The involvement of rggL in NaCl-induced gene expression was examined using the rggL insertion mutant MGNS3i3 (see 1.6.1 below). RNA was isolated from MG1363 and MGNS3i3 cultured with and without NaCl and transferred to a filter. The 440 bp XbaI-Sau3A fragment carrying the 5'-end of orfX was used as a probe in Northern hybridization. A strong hybridization signal was seen with RNA from MG1363 grown with NaCl (see FIG. 11). Only a very weak signal was detected in the absence of NaCl, confirming the results obtained with the lacZ fusions. The same weak signal was seen with RNA from the rggL insertion mutant, both from cells grown with and without NaCl. This indicates that RggL acts as a positive regulator in NaCl-dependent expression of orfX. The size of the NaCl-dependent transcript in MG1363 was estimated to be approximately 3.0 kb.

1.6.1 Construction of an rggL Insertion Mutant

Figure 28:
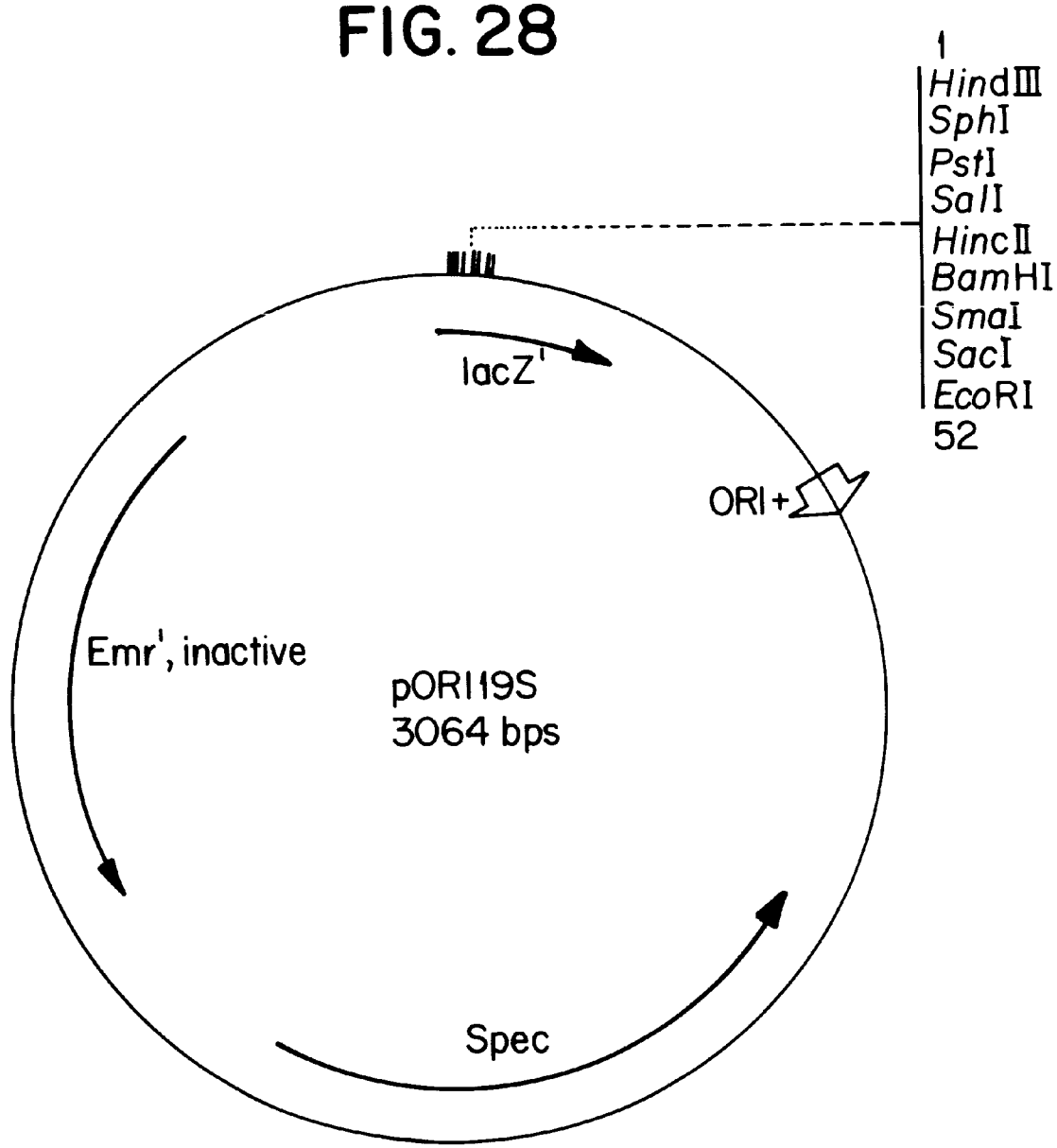

An internal XbaI-HindIII fragment of the rggL gene was cloned in the integration vector pORI19S (see FIG. 28), using the RepA+ E. coli helper strain EC101. This plasmid, pNS3i3, was used to disrupt the rggL gene in L. lactis MG1363, as described before (see ref. 37; J. Law c.s.; 1995). The proper chromosomal location of the integrated plasmid was confirmed by Southern hybridization (not shown) and the strain was named MGNS3i3.

EXAMPLE 2 lacZ expression from NS3 is halide-ion-dependent

Figure 12:
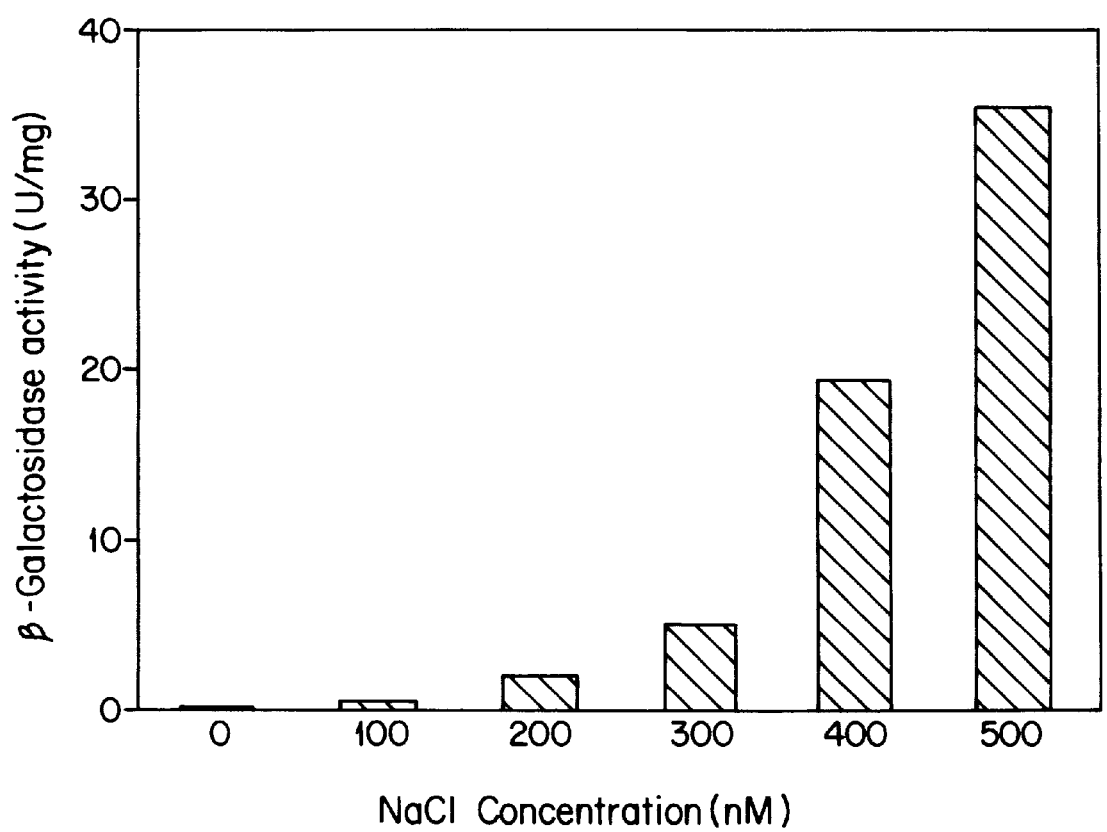

In agar plates a number of compounds were tested to reveal the nature of the inducing condition (see Table 3 below). lacZ expression appeared to be independent of the osmolarity of the medium but was strictly linked to the presence of Cl− or I− β-galactosidase activity increased with increasing NaCl concentrations in the medium (FIG. 12). No induction of β-galactosidase activity was observed by increasing the growth temperature.

EXAMPLE 3

Salt-induced Expression of Phage r1-t lytPR Genes Prevents Outgrowth of a Lactococcal Culture The transcription start point upstream of orfX and rggL were amplified as a cassette using primer NS3-7 and NS3-8 and cloned upstream of the holin and lysin genes (lytPR) of the lactococcal temperate bacteriophage r1-t (see ref. 38; D. van Sinderen c.s.; 1996 and ref. 35; Quest International B.V. (A. Nauta c.s.); WO 95/31562). The start codon of orfX was fused

TABLE 3 lacZ expression in strain NS3 in the presence of different compounds

| Compound[a] | concentration (Mol/l) | β-galactosidase activity[b] |
|---|---|---|
| none | — | − |
| Maltose | 0.5 | − |
| Mannitol | 0.5 | − |
| Sorbitol | 0.41 | − |
| Sucrose | 0.5 | − |
| K$_2$SO$_4$ | 0.25 | − |
| MgSO$_4$ | 0.25 | − |

TABLE 3-continued lacZ expression in strain NS3 in the presence of different compounds

| Compound[a] | concentration (Mol/l) | β-galactosidase activity[b] |
|---|---|---|
| NaAcetate | 0.25 | − |
| Na$_2$SO$_4$ | 0.15 | − |
| Na$_2$Succinate | 0.25 | − |
| NH$_4$Acetate | 0.25 | − |
| CaCl$_2$ | 0.05 | + |
| KCl | 0.3 | + |
| KI | 0.3 | + |
| MgCl$_2$ | 0.125 | + |
| NaI | 0.3 | + |
| NH$_4$Cl | 0.25 | + |

Figure 14:
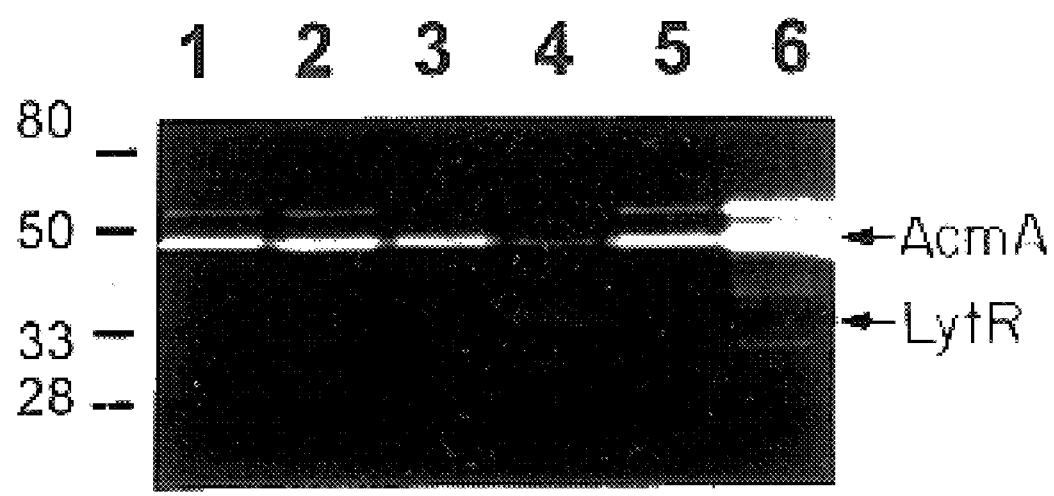
Figure 15:
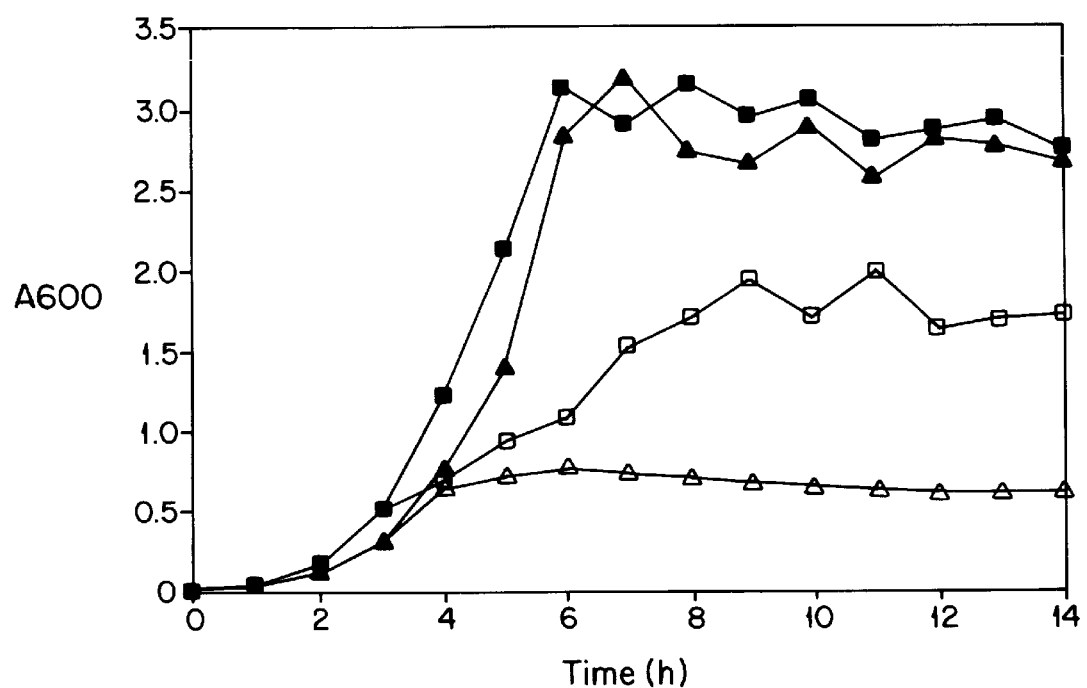

[a]Chemicals were added at the indicated final concentrations to GM17 agar containing Em and X-gal
[b]−: white colonies +: blue colonies in-frame to ORF5 of r1-t which stops 13 bp upstream of the start codon of lytp, resulting in efficient translation of lytP and lytr (FIG. 13A and SEQ. ID. NO: 18). Cultures of the resulting strain, LL108(pNS3PR), were grown in GM17 and induced at an optical density at 600 nm (OD600) of 0.5 by the addition of 0.5 M NaCl. FIG. 14, lane 4 shows that 6 hours after induction, in addition to wild-type autolysin activity, phage lysin activity was present in the induced cells, and absent in the cells grown without NaCl. The addition of NaCl led to a stop in the increase of the OD600 of LL108 (pNS3PR) followed by a decrease in optical density 4 hours after induction (FIG. 15). The control strain, LL108 (pNS378) expressing lacZ, continued to grow after NaCl addition, albeit at a lower rate.

3.1 Construction of a Transcriptional Fusion of the NS3 Promoter with the Phage r1-t Holin and Lysin Genes A 1280 bp fragment, encoding rggL and the salt-inducible promoter, was amplified by PCR using primers NS3-7 and NS3-8 (see Table 2 above) and pNS3 as template. This fragment was digested with SacI and EcoRV and ligated to pIR1PR (see ref. 35; Quest International B.V. (A. Nauta c.s.); WO 95/31562) linearized with SacI and ScaI. The ligation mixture was used to transform L. lactis LL108 and the resulting plasmid was called pNS3PR (see FIG. 16). As a negative control for lytic activity, the same PCR fragment was cloned upstream of lacZ in pORI13. The PCR fragment was cut with BglII and EcoRV and ligated to BglII-SmaI-digested pORI13. The ligation mixture was used to transform LL108 and the resulting plasmid was labeled pNS378.

EXAMPLE 4

Figure 17:
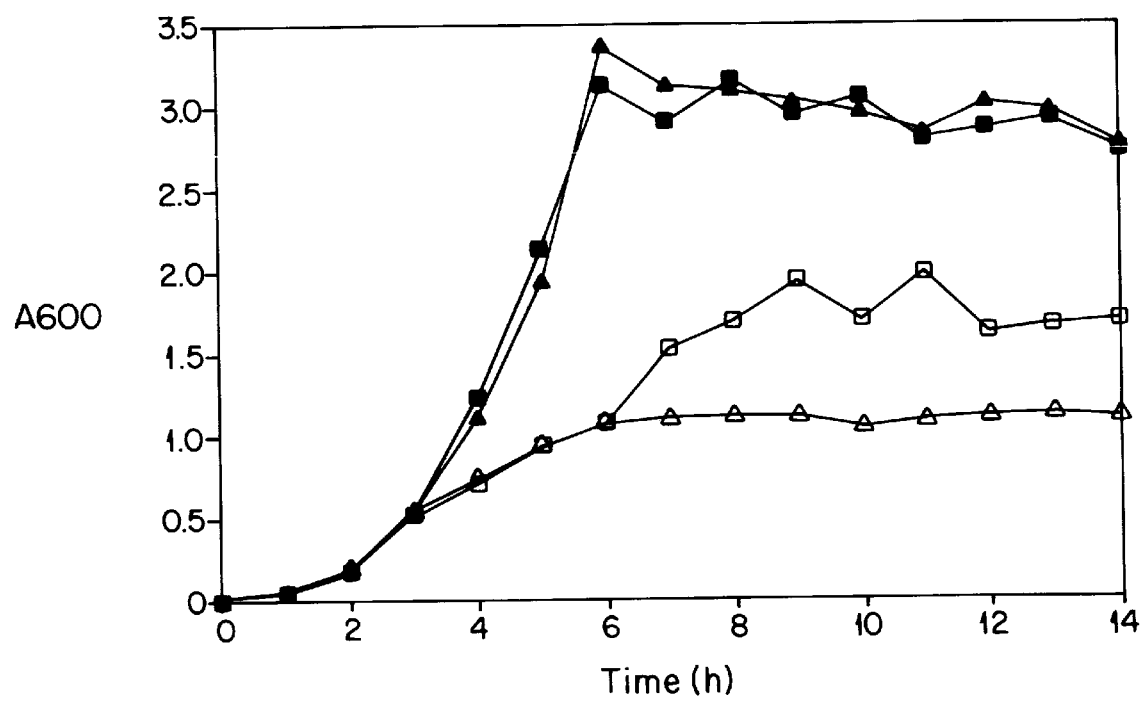

Salt-induced Expression of the Lactococcal acmA Gene Results in the Stabilization of the OD600 of a Culture The cassette containing rggL, the salt-inducible promoter, and the RBS and start codon of orfX was placed upstream of acmA, the gene of the major peptidoglycan hydrolase of Lactococcus lactis (see ref. 34; Quest International B.V. (G. Buist c.s.); WO 95/31561 and ref. 31; G. Buist c.s.; 1995). Two mutations occurred in the fusion region. An A to G transition in the untranslated leader of the transcript (see nucleotide 64 in FIGS. 13A+13B and SEQ. ID. NO: 18 and SEQ. ID. NO: 19) and a deletion of an A residue (see nucleotide 99 in FIG. 13B and SEQ. ID. NO: 19) resulting in the loss of the ScaI site at the fusion point. Translation of the fusion transcript results in the formation of a heptapeptide from the RBS of orfX and the translation of acmA from its own RBS (FIG. 13B and SEQ. ID. NO: 19). Translation of the small peptide stops 10 bp upstream of the RBS of acma. The growth of the strain carrying the resulting plasmid, pNS3AL3, did not differ from the control strain in GM17 broth (FIG. 17). However, upon addition of NaCl the cells grew slower and the OD600 stabilized after 4 hours. The OD600 of the control strain increased to a higher level in the presence of salt. More AcmA activity was detected in cells induced with NaCl compared to uninduced cells and to control cells expressing β-galactosidase under control of the same induction cassette (FIG. 14). Clearly, the expression of acmA from pNS3AL3 is induced by NaCl.

Figure 18:
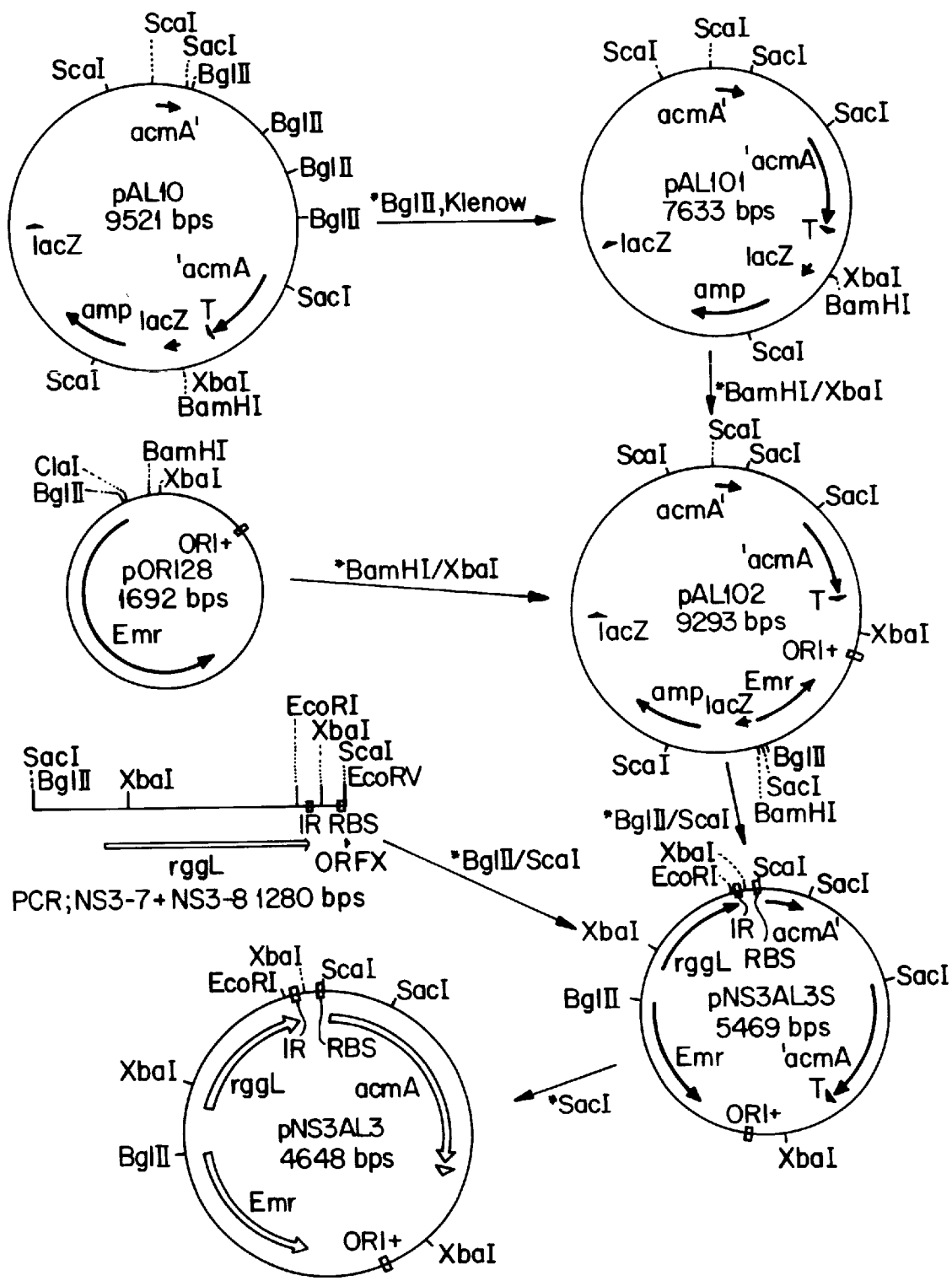

4.1 Construction of a Transcriptional Fusion of the NS3 Promoter with the Lactococcal Autolysin Gene acmA The acmA gene interrupted by a SacI fragment on pAL10 was used as a basis (see ref. 34; Quest International B.V. (G. Buist c.s.); WO 95/31561). The BGlII sites in pAL10 were deleted by cutting with BglII, filling the overhanging ends with Klenow polymerase, recircularization with T4 ligase and transformation of EC1000. This construct, pAL101, was linearized with BamHI and XbaI and ligated to pORI28, also linearized with BamHI and XbaI. The proper construct, pAL102, was isolated from E. coli EC1000. A PCR fragment, made by amplification using NS3-7 and NS3-8 on pNS3 as the template and described in Example 3.1 above, was cut with BglII and ScaI and ligated to pAL102, linearized with the same restriction enzymes. The ligation mixture was used to transform L. lactis LL302 and pNS3AL3S was recovered. This plasmid was digested with SacI to delete the insert in acmA. After self-ligation the mixture was used to transform LL302. The resulting construct, carrying an intact acmA copy fused to the NS3 salt-inducible promoter, was designated pNS3AL3 (see FIG. 18).

EXAMPLE 5

Intracellular Proteins are Released upon Induction of Lysin Genes

Figure 19A:
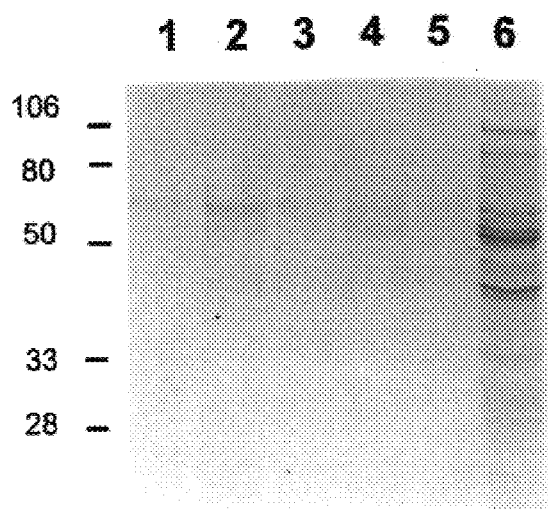
Figure 19B:
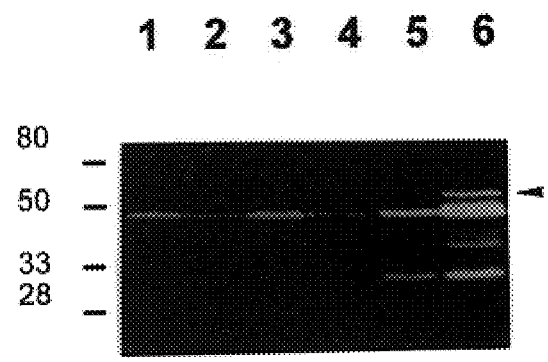

The supernatant of the holin-lysin expressing strain (see ref. 35; Quest International B.V. (A. Nauta c.s.); WO 95/31562) contains a significant amount of cytoplasmic proteins 6 hours after NaCl addition, whereas in the supernatant of the same strain grown without induction only secreted proteins are visible (FIG. 19.A, lane 3). The addition of NaCl to the control strain already causes the release of a small portion of cytoplasmic proteins (FIG. 19.A, lane 2). In the supernatant of cells overexpressing AcmA a much larger quantity of cytoplasmic proteins was observed (FIG. 19.A, lane 6) when compared to the amount of intracellular proteins released from LL108(pNS3PR). To detect lytic activity, sodium dodecyl sulphate (12.5%) polyacrylamide gel-electrophoresis was carried out as described (see ref. 1; U. K. Laemmli; 1970) whereby 0.2% autoclaved, lyophilized Micrococcus lysodeikticus cells were included in the gel (see ref. 31; G. Buist c.s.; 1995). In FIG. 19.B, lane 4 it was shown that LytR activity was detectable in the supernatant of induced LL108(pNS3PR). Using the same method it was also shown that a high level of AcmA activity was present in the supernatant of induced LL108 (pNS3AL3). A number of breakdown products of AcmA were visible, as well as the precursor form of AcmA, which is normally present in the cytoplasm (see ref. 34; Quest International B.V. (G. Buist c.s.); WO 95/31561 and ref. 31; G. Buist c.s.; 1995). This latter protein is not processed by the protein export machinery and, therefore, must have been released by cell lysis. AcmA activity in the NaCl-induced samples of LL108(pNS378) and LL108(pNS3PR) was lower than in non-induced samples. This is, most likely, due to the lower OD of the corresponding culture at the moment of sampling (see FIG. 15 and FIG. 17).

5.1 Determination of Peptidase Activity in the Supernatant of L. lactis Cultures In order to quantify the release of intracellular proteins PepXP was chosen as an intracellular marker enzyme. Cell lysis was quantified by measuring PepXP release from cells lacking the chromosomal autolysin gene. MG1363acmAΔ1-(pVE6007) was transformed with either pNS3PR or pNS3AL3. PepXP activity in supernatant samples was determined by following hydrolysis of the synthetic substrate Ala-Pro-p nitroanilide at 405 nm for minutes at 37° C. in a 96-well microtiterplate using a Thermomax microplate reader (Molecular Devices Co., Menlo Park, Calif.). The presence of protoplasts in induced cultures was tested by washing 1 ml of cells in medium containing a concentration of NaCl which was identical to that in the original culture. Subsequently, half of the cells were resuspended in 0.5 ml of (hypoosmotic) M17 and the other half in 0.5 ml M17 containing the original NaCl concentration. Samples were incubated for 30 minutes at 37° C. and PePXP activity in the supernatants was measured. PepXP activity in the hypoosmotic extractable cell fraction is given as the activity in the first 0.5 ml corrected for the activity in the latter 0.5 ml.

Figure 20:
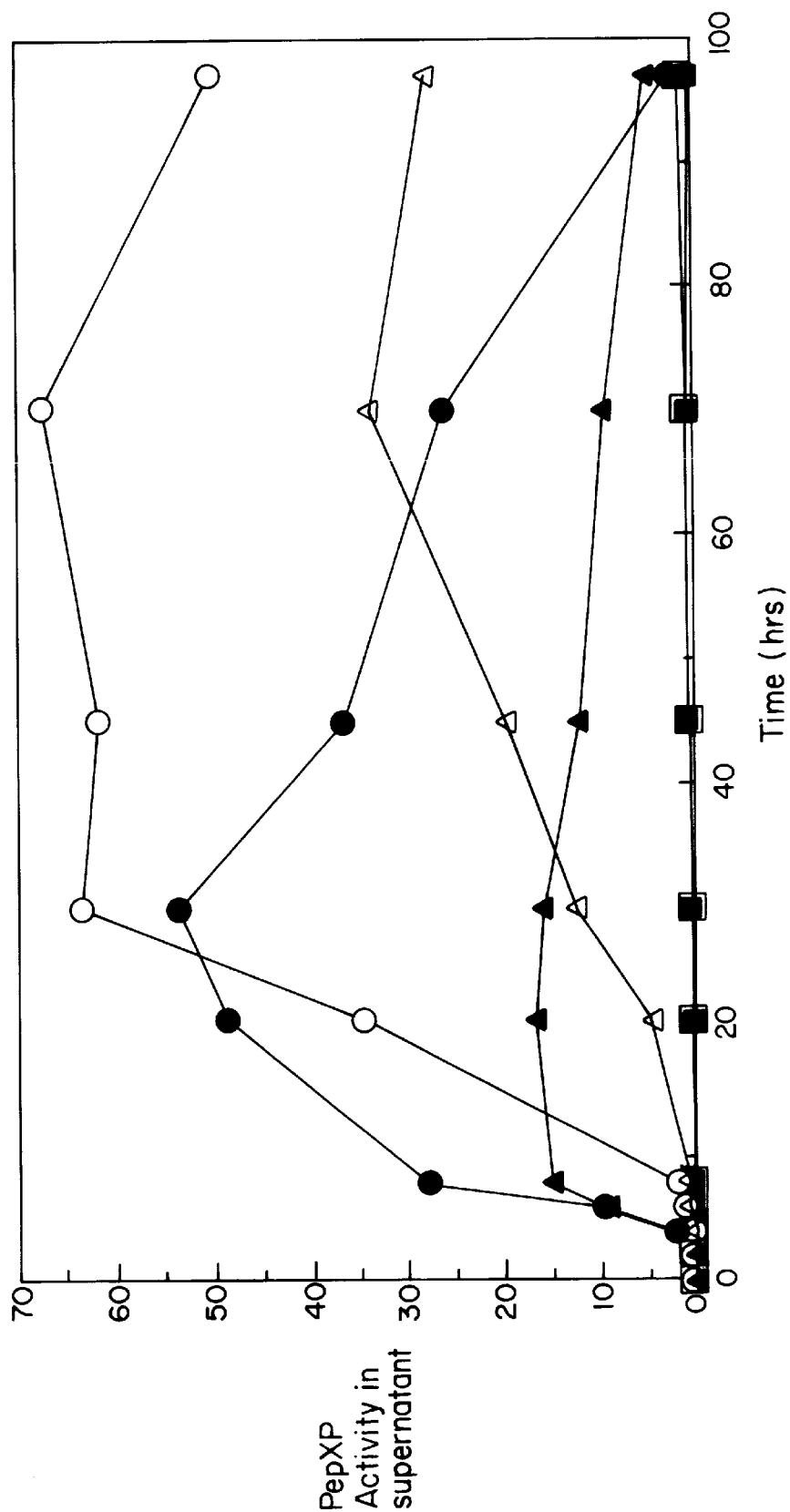
Figure 21:
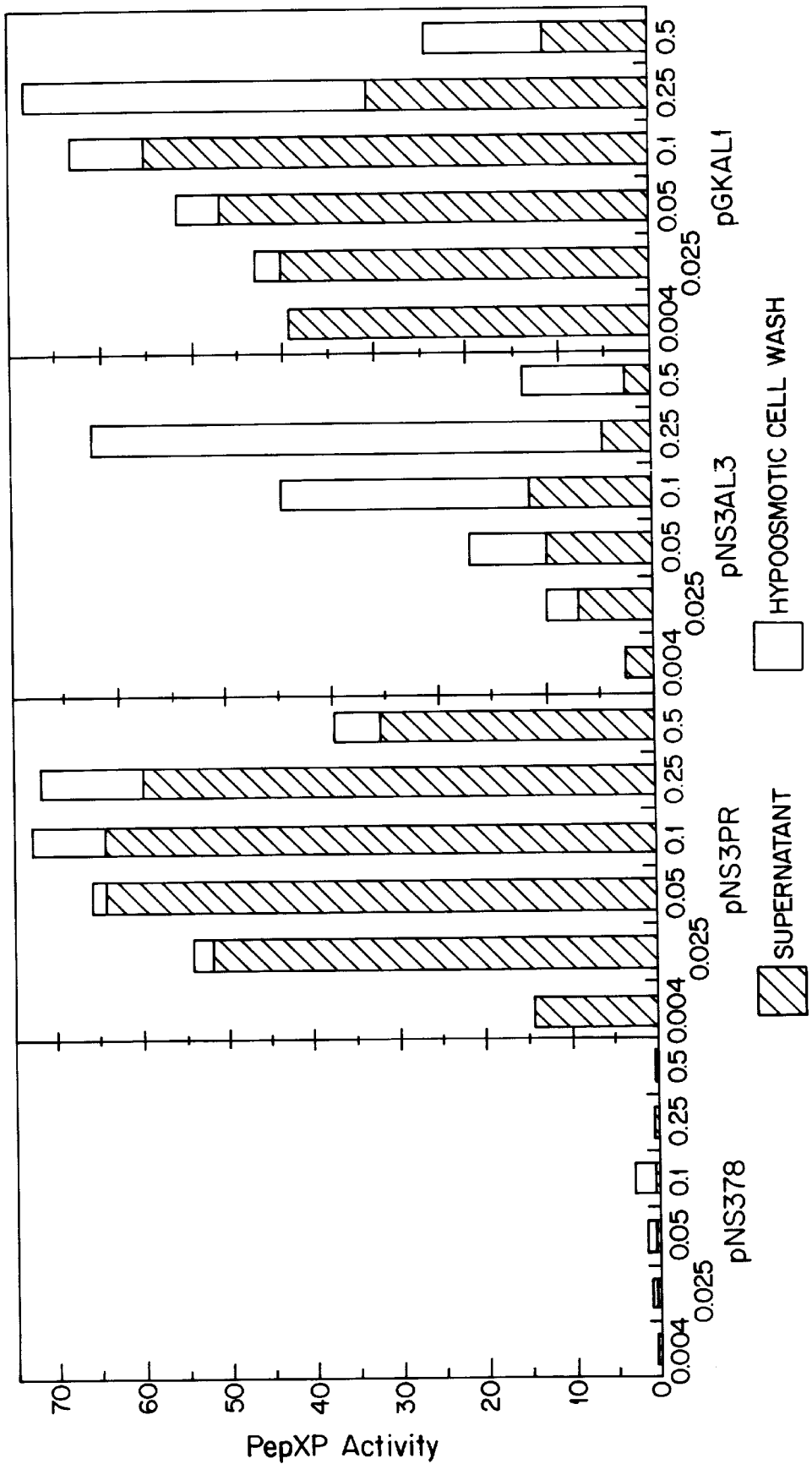

In order to exclusively study the effect of the salt-induced lysis genes PepXP activity in culture supernatants was followed after induction of either lysin gene with 0.5 M NaCl at a culture OD600 of 0.5. During the first hours after induction low levels of PepXP were detected in the culture supernatants (FIG. 20). Optimal PepXP levels were obtained 8 hours after induction of cultures of MG1363acmAΔ1 (pVE6007)-(pNS3AL3) and 30 hours after induction of MG1363acmAΔ1-(pVE6007)(pNS3PR). The highest level of PepXP activity was present after induction with 0.1 M NaCl (FIG. 21). Highest PepXP levels were reached at 30 hours after induction with 0.1 M NaCl of strains carrying the NS3::lytPR fusion and 70 hours after induction of the NS3::acmA strain (FIG. 20). The control strain, carrying NS3::lacZ, released low levels of PepXP activity after prolonged incubation. PepXP activity is stable for at least 40 hours in a cell extract in M17, either with or without NaCl (data not shown).

The addition of NaCl to a culture not only induces the activity of the NS3 promoter but also increases the osmolarity of the medium. This probably results in stabilization of osmotically fragile cells formed by lysin activity in the cultures. By incubation in hypoosmotic medium extra PepXP activity could be released from cells carrying the NS3::lytPR fusion induced with 0.1, 0.25, or 0.5 M NaCl, indicative of the formation of fragile cells by the action of LytPR (FIG. 21). Induction of acmA expression with NaCl resulted in much lower levels of PepXP in the culture medium compared to induction of lytPR. However, much more PepXP was extractable with hypoosmotic medium from NS3::acmA carrying cells. The sum of PepXP in the supernatant and PepXP extractable from cells is comparable for NS3::acmA and NS3::lytPR cells induced with 0.25 M NaCl. The amount of PepXP extracted from NS3::acmA cells increased with the amount of NaCl used for induction. Only after induction with 0.5 M NaCl a smaller amount of PepXP was extracted. Cells that constitutively overexpress AcmA {MG1363(pGKAL1)} released slightly more PepXP in the presence of 0.1 M NaCl as compared to M17 without added NaCl. At higher NaCl concentrations less PepXP was liberated from these cells. Also from this strain, incubated in 0.25 or 0.5 M NaCl, high levels of PepXP were extractable with hypoosmotic M17. Apparently, AcmA activity results in a weaker cell wall but not in cell lysis in medium containing NaCl.

KCl could replace NaCl as the inducing agent, resulting in only slightly lower levels of released PepXP (data not shown).

EXAMPLE 6

A chloride and low pH-inducible Acid Resistance Mechanism in Lactococcus lactis.

In this Example the term gad is used to indicate a group of genes involved in glutamate-dependent acid resistance. Therefore, the genes indicated above with rggL and orfX have now been renamed as gadR and gadC, respectively. The reason for the abbreviation "rggL" was discussed in Example 1.4 above. The reason for the abbreviations "gadB" "gadC" "gadR" is discussed below under the heading RESULTS.

Additional MATERIALS AND METHODS

Bacterial Strains, Plasmids, and Growth Conditions.

The (additional) bacterial strains and plasmids used in this Example are listed in Table 4. L. lactis was grown at 30° C. in half strength M17 (½M17) broth containing 0.5% glucose and 1.9% β-glycerophosphate; solidified ½M17 contained 1.5% agar. Modified M17 (mM17) contained no β-glycerophosphate and no soytone. β-glycerophosphate was added to a final concentration of 2%, where indicated.

General DNA Techniques.

Protein homology searches against the Genbank were carried out using the BLAST program (Altschul et al., 1990; ref. 41). Protein sequence alignments were carried out with the PALIGN program of PC/Gene using the structure genetic matrix. Transmembrane segments were predicted using the method of Klein et al. (1985; ref. 45)

Cloning of gadCB of L. lactis

Figure 22:
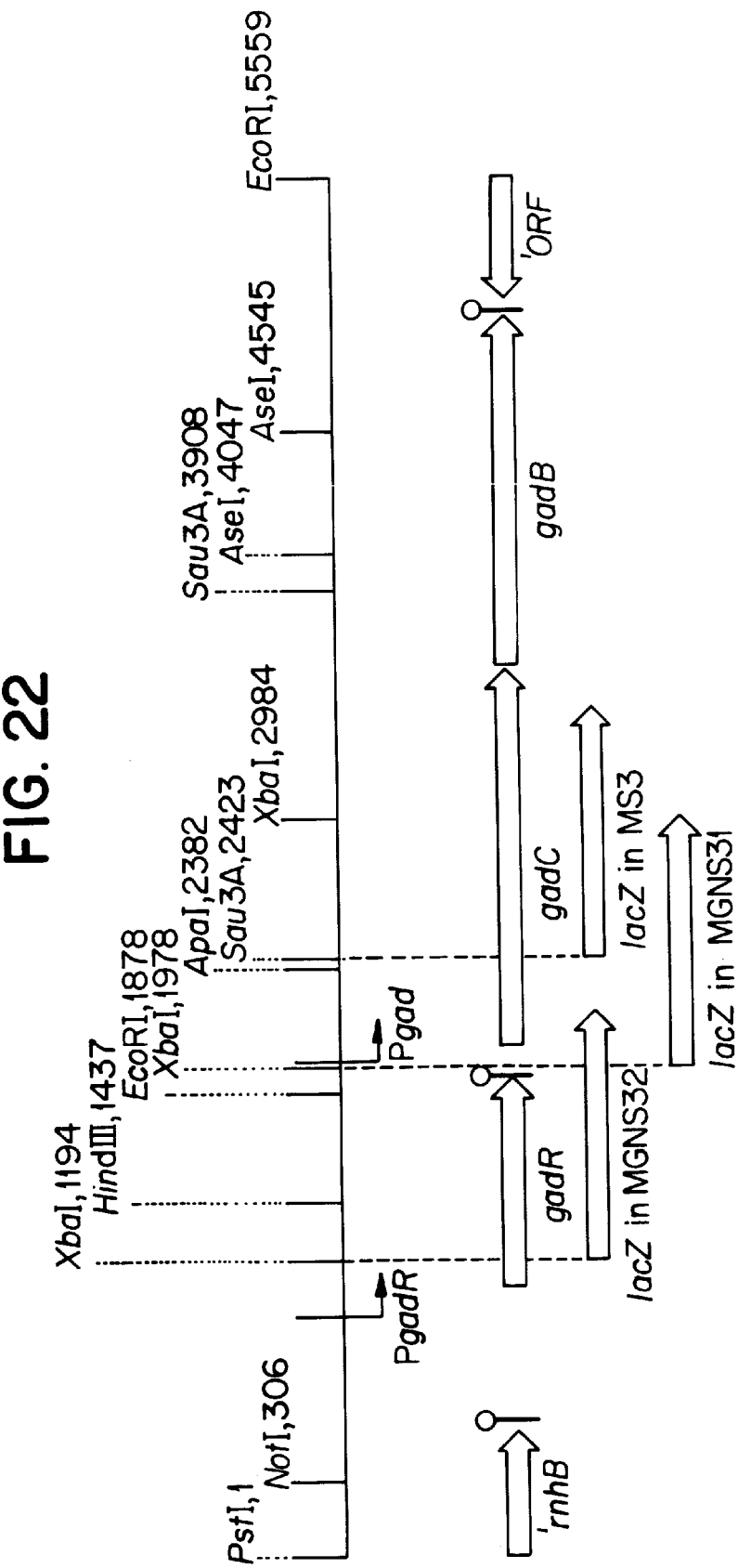

The region downstream of the lacZ fusion site in L. lactis NS3 was obtained by inverse PCR amplification of a 0.56-kb Sau3A-XbaI fragment from L. lactis MG1363 chromosomal DNA using primers NS3-5 and NS3-11 (see Table 2 above). The PCR product was cloned in pORI19 using Escherichia coli EC101 as a host, resulting in pNS3i4 (see Example 1.4.1 above and FIG. 27). In a subsequent inverse PCR the adjoining 0.9-kb XbaI-Sau3A chromosomal DNA fragment was amplified using primers NS3-14 (5'-GGCAGTCCGTTGCGTCCCACC) and NS3-15 (5'-GAGTTATCATTAAGTGCAGGGG) and cloned in pORI19 using L. lactis LL108 as the cloning host. This construct was named pNS3i5 (see FIG. 27) and used for single cross-over integration, resulting in strain MGNS3i5. Chromosomal DNA of MGNS3i5 was digested with EcoRI to clone sequences downstream of the insertion site of pNS3i5. The chromosomal EcoRI fragments were circularized by self-ligation and the ligation mixture was used to transform L. lactis LL108. Transformants contained a 4.8-kb plasmid (pNS3i6; see FIG. 27) which is pORI19 containing a 2.6-kb XbaI-EcoRI fragment from the chromosome (FIG. 22).

TABLE 4

Additional bacterial strains and plasmids for Example 6

| Strain or plasmid | Relevant characteristics | Reference or source |
|---|---|---|
| Strains | | |
| L. lactis | | |
| LL302 | MG1363 derivative, carrying a single repA copy in pepXP | Leenhouts, unpublished, See earlier Examples |
| MGNS3i3 | Sp$^r$, derivative of MG1363 with pNS3i3 inserted in gadR | See earlier Examples |
| MGNS3i4 | Em$^r$, derivative of MG1363 with pNS3i4 inserted in gadC | This work |

TABLE 4-continued

Additional bacterial strains and plasmids for Example 6

| Strain or plasmid | Relevant characteristics | Reference or source |
|---|---|---|
| MGNS3i5 | Em$^r$, MG1363 derivative carrying a single copy of pNS3i5 on the chromosome | This work |
| MGNS3i7 | Em$^r$, derivative of MG1363 with pNS3i7 inserted in gadB | This work |
| MGNS31 | Em$^r$, MG1363 with lacZ inserted between gadR and P$_{gad}$ | This work |
| MGNS32 | Em$^r$, MG1363 (gadR::lacZ) | This work |
| E. coli | | |
| EC101 | Km$^r$, JM101 derivative, carrying a single copy of the pWV01 repA gene in glgB | Law et al., 1995; ref. 37 |
| Plasmids | | |
| pORI13 | Promoterless lacZ, Em$^r$, Ori$^+$, RepA$^-$ derivative of pWV01 | See earlier Examples |
| pNS3i3 | Sp$^r$, pORI19S carrying a 240-bp XbaI-HindIII fragment internal to gadR | See earlier Examples |
| pNS3i5 | Em$^r$, pORI19 carrying a 0.9-kb XbaI-Sau3A chromosomal DNA fragment encoding the 3'-end of gadC and the 5'-end of gadB | This work |
| pNS3i6 | Em$^r$, pORI19 carrying a 2.4-kb XbaI-EcoRI chromosomal DNA fragment | This work |
| pNS3i7 | Em$^r$, pORI19 carrying a 500-bp internal AseI fragment of gadB | This work |

Construction of Insertion Mutants.

An internal XbaI-HindIII fragment of gadR was cloned as a blunt fragment in the SmaI site of pORI19S (Bee FIG. 28) using the RepA$^+$ E. coli helper strain EC101. The resulting plasmid, pNS3i3, was used to disrupt gadR in L. lactis MG1363, as described before (Law et al., 1995; ref. 37). The proper chromosomal location of the integrated plasmid was confirmed by Southern hybridization and the strain was named MGNS3i3. Plasmid pNS3i7 was constructed by cloning a 0.5-kb AsnI fragment (internal to gadb) as a blunt fragment in the SmaI site of pORI19 using E. coli EC101 as a host (see FIG. 27). Single cross-over integration of pNS3i4 and pNS3i7 in the L. lactis MG1363 chromosome resulted in strains MGNS3i4 (gadC) and MGNS3i7 (gadB), respectively.

β-Galactosidase Assays.

Cell-free extracts were prepared by vigorous shaking of cells in the presence of glass beads (van de Guchte et al.,1991; ref. 24). β-Galactosidase activity was determined as described by Miller (1972; ref. 2). Protein concentrations were determined by the method of Bradford (1976; ref. 3) with bovine serum albumin as the standard.

Acid Resistance Tests.

Cells of an exponentially growing culture of L. lactis in half strength GM17 (½GM17) with or without 0.3 M NaCl was harvested, washed with water and resuspended in an equal volume of MS15 (Cocaign-Bousquet et al., 1995; ref. 42) without glucose and glutamate and containing the same amount of NaCl as the culture. The pH of MS15 was adjusted to 3.5 with either lactic acid or hydrochloric acid prior to cell resuspending. After incubation for 2 hours at 30° C. the number of viable cells was determined by plating onto glucose ½M17 plates. The percentage of acid resistant cells was calculated from the number of colony-forming units (cfu) after acid treatment divided by the number of cfu found at the moment of harvest.

RESULTS

Nucleotide Sequence of the Genes Transcribed by the Chloride-dependent Promoter.

In the previous Examples the chloride-dependent promoter (P$_{gad}$) was identified using a random lacZ chromosomal integration strategy. Here the nucleotide sequence is presented of the chromosomal region downstream of the lacZ integration site in L. lactis NS3.

The original Sau3A fusion site in the lacZ integrant L. lactis NS3 is located in an ORF of 503 codons immediately downstream of P$_{gad}$. This ORF was named gadC, as its deduced amino acid sequence (FIGS. 23A-C) is homologous to GadC from Shigella flexneri (51% identity and 17% similarity, Waterman and Small, 1996; ref. 47) and its E. coli counterpart XasA (Hersh et al., 1996; ref. 43). GadC is homologous to a number of amino acid antiporters, including the lysine-cadaverine antiporter CadB from E. coli (Meng and Bennet, 1992; ref. 46). Lactococcal GadC has a deduced molecular weight of 55369 and a pI of 9.73 and is highly hydrophobic. The hydrophobic residues are clustered in 12 domains (FIGS. 23A-C), whose locations coincide with those of the hydrophobic domains in S. flexneri GadC (as predicted by a number of topology-predicting computer programs). This suggests that GadC is an integral membrane protein. A conserved domain found in glutamate transporting proteins is also present in L. lactis GadC (FIGS. 23A-C, Waterman and Small, 1996; ref. 47); gadC is separated by 19-bp from another ORF of which the deduced protein is homologous to glutamate decarboxylases. Highest homology is found with glutamate decarboxylase from Synechocystis sp. (48% identity and 15% similarity, FIGS. 24A-B, Kaneko et al., 1996; ref. 44). Both in E. coli and S. flexneri gadB is linked to the putative glutamate-γ-amino butyrate antiporter genes, xasA and gadC, respectively. The lactococcal gene was, in analogy to E. coli, and S. flexneri named gadB. The gene order of gadB and gadC is inverse in L. lactis compared to these organisms. No possible transcription signals could be identified in the 19-bp intergenic region between gadC and gadB which suggests that they form an operon. Downstream of gadB a 16-bp inverted repeat (IR) may function as a rho-independent transcription terminator.

gadR is Constitutively Expressed

Expression of gadR was studied in strain MGNS32 carrying a single copy gadR::lacZ transcriptional fusion (see FIG. 22). β-galactosidase activity in exponentially growing MGNS32 was 3.0 U/mg, independent of the presence of NaCl. In other words, NaCl-dependent expression from P$_{gad}$ is not regulated by variations in the level of transcription of gadR. Another lacZ fusion, located immediately downstream of the 21-bp IR was used to show that transcription of gadR is effectively terminated by this IR. No β-galactosidase activity could be detected in strain MGNS31 carrying this fusion (see FIG. 22). Transcription of gadR starts from a C-residue 116 bp upstream of the AUG start codon (FIG. 22). The gadR promoter consists of canonical −35 and −10 hexanucleotides separated by 18 bp (FIGS. 6C and 29C).

Expression of gadCB is Enhanced at Low pH and by Glutamate

In S. flexneri and E. coli gadC and xasA have been shown to play a role in survival at low pH in the presence of glutamate (Waterman and Small, 1996; ref. 47; Hersh et al., 1996; ref. 43). The expression of lactococcal gadC under such conditions was studied in L. lactis NS3. Strain NS3 was previously identified because of its chloride-dependent lacZ expression and contains a single copy gadC::lacZ fusion on its chromosome (see previous Examples). A modified M17 medium (mM17) was used, lacking the buffer β-glycerophosphate to modulate the culture pH; mM17 also lacks soytone. β-galactosidase activity in NS3 was still induced in this modified medium in the presence of 0.3 M NaCl and 2% β-glycerophosphate buffer but the induction level was fivefold lower as compared to that in standard ½M17 (data not shown). The lacZ expression in mM17 in the presence of NaCl was low in the early stages of exponential growth and increased to an optimum at the onset of the stationary phase (FIGS. 25A-B). In the absence of buffer, the culture pH decreased to 4.0 to 4.5 in the stationary growth-phase, while cultures containing buffer reached a lowest pH of 5.5. Expression of lacZ was increased 10-fold in mM17 containing no buffer. The presence of 50 mM glutamate resulted in an approximately twofold additional increase in the expression of lacZ both in buffered and in unbuffered mM17 broth (FIG. 25). No β-galactosidase activity was detectable in the absence of NaCl whether or not glutamate was present and independent of the culture pH (data not shown). Therefore, expression of gadCB is optimal at the onset of the stationary growth phase in the presence of NaCl and glutamate, and at low pH.

gadCB Confers Acid Resistance

The ability of *L. lactis* MG1363 to survive acid stress was tested under conditions where gadCB is expressed and under conditions where gadCB is not expressed. When MG1363 was grown in ½GM17 and acid-challenged at pH 3.5 in MS15 for two hours the viability of the cells decreased dramatically (Table 5).

TABLE 5

Acid resistance of *L. lactis* MG1363 under different conditions of challenge

| conditions: | % acid resistance at pH 3.5, lactic acid | % acid resistance at pH 3.5, HCl | % acid resistance at pH 6.5 |
|---|---|---|---|
| — | 0.0005 | 1.12 | 139 |
| +1 mM glutamate | 0.0004 | 0.96 | 135 |
| +0.3 M NaCl | 0.0002 | 1.00 | 58 |
| +0.3 M NaCl +1 mM glutamate | 0.49 | 16 | 57 |

Lactic acid was much more deleterious than hydrochloric acid whereas the viability was not affected at pH 6.5. The presence of 1 mM glutamate alone did not affect the viability at pH 3.5. In the presence of 0.3 M NaCl during growth, allowing gadCB expression, followed by acid challenge in the presence of 0.3 M NaCl and 1 mM glutamate the viability was reduced only 200-fold when lactic acid was used. Under the latter conditions, the viability in MS15 adjusted to pH 3.5 with hydrochloric acid was also enhanced significantly. Under conditions of gadCB expression (by the presence of 0.3 M NaCl) acid resistance was lower in the absence of glutamate than when glutamate was present (Table 5), indicating that glutamate is not only involved in induction of gadCB expression but is directly needed to confer acid resistance. To confirm the direct involvement of gadCB in acid resistance *L. lactis* MGNS3i3 (which does not express gadCB, see earlier Examples) was subjected to acid challenge.

TABLE 6

Acid resistance of *L. lactis* gadCB mutants.

| Strain | Genotype; | % acid resistance[a] in MS15 | % acid resistance[a] in MS15 + NaCl + glu |
|---|---|---|---|
| MG1363 | w.t. | 0.0005 | 0.49 |
| MGNS3i3 | gadR | 0.0003 | 0.0013 |
| MGNS3i4 | gadC (GadB−)[b] | 0.00007 | 0.00009 |
| MGNS3i5 | (GadB−)[b] | 0.00003 | 0.00026 |
| MGNS3i7 | gadB | 0.00001 | 0.00008 |

[a]at pH 3.5, lactic acid
[b]Insertions in gadC and in between gadC and gadB will, most likely, have a polar effect on gadB.

Figure 26:
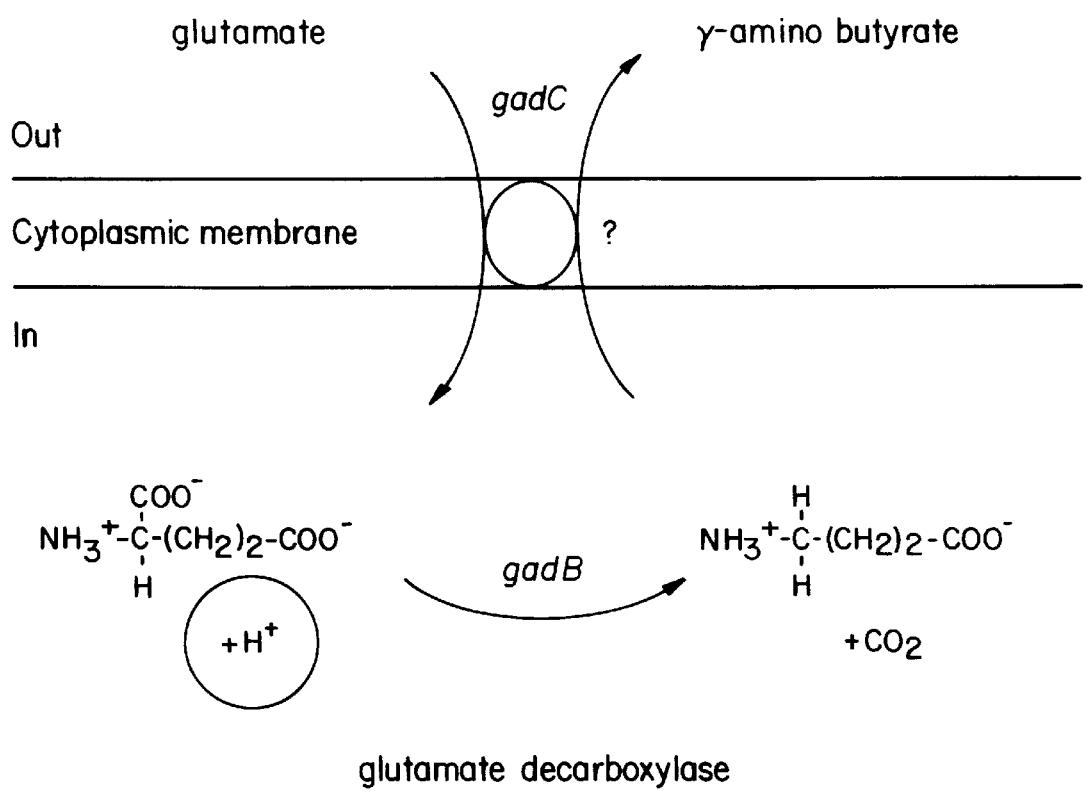

Survival in the presence of NaCl and glutamate was reduced to levels comparable to that of the wild-type strain in the absence of NaCl and glutamate (Table 6). An insertion mutant in gadC (strain MGNS3i4) showed a similar phenotype. This mutation, most likely, has a polar effect on qadb which would result in the absence of both GadC and GadB. An insertion mutant in gadB (strain MGNS3i7) is similarly acid sensitive, indicating a central role for GadB in the acid resistance process. Strain MGNS3i5, carrying intact copies of gadC and gadB separated by an integrated copy of pORI19 is acid sensitive, suggesting that gadB expression is abolished. These data show that gadCB, which is transcribed from the chloride-dependent gad promoter $P_{gad}$, is involved in glutamate-dependent acid resistance, as depicted in FIG. 26.

SUMMARY

*Lactococcus lactis* MG1363 has a glutamate-dependent acid resistance mechanism, that is active in the presence of chloride.

*L. lactis* has two genes, gadC and gads, that encode proteins homologous to a putative glutamate-γ-aminobutyrate antiporter and a glutamate decarboxylase, respectively, from *Escherichia coli* and *Shigella flexneri*. These genes are involved in glutamate-dependent acid resistance in *E. coli* and *S. flexneri*.

The expression of gadCB in *L. lactis* is induced by chloride and is optimal at low pH in the presence of glutamate.

*L. lactis* insertion mutants with a disrupted gadB or that are unable to express both gadB and gadC are more sensitive to low pH than the wild-type when NaCl and glutamate are present, indicating that the lactococcal gadCB operon is involved in glutamate dependent acid resistance, see FIG. 26.

Conclusions to be Drawn from Example 6

The results of further research given in Example 6 have shown that this salt-inducible promoter is more active at a lower pH. For example, FIG. 25A shows that upon induction with 0.3 M NaCl the yield of β-galactosidase is not more than about 8 Units/mg when the medium is buffered such that the pH will not come below 5.5.

In contrast therewith, FIG. 25B shows that in the absence of a buffer the pH can drop to about 4, while under these conditions the yield of β-galactosidase is about 80 Units/mg.

The salt-inducible promoter is more active at a lower pH and has thus also become pH-inducible in the presence of salt. The activity of the salt- and pH-inducible promoter can be further enhanced in the presence of glutamate/glutamic acid, as is shown in FIGS. 25A and 25B. They show that production of β-galactosidase is increased from 8 to 15 Units/mg in a buffered medium and from 80 to 225 Units/mg in a non-buffered medium when the pH during fermentation has dropped to about 4.3.

Although the scope of the invention is not limited by any theory, it is supposed that these enhancing effects are caused by control of the internal pH by the uptake of glutamate and decarboxylation whereby γ-aminobutyrate is formed and subsequently secreted under influence of the gadB and gadC genes described in this Example.

Thus Example 6 shows that a desired protein can be produced in a lactic acid bacterium at an improved yield by using a construct in which the gene encoding the desired protein is under control of a salt- and pH-inducible promoter and the medium in which the transformed lactic acid bacterium is cultured is not buffered and preferably contains glutamate/glutamic acid. For an easy recovery it is generally desirable that the desired protein contains a secretion signal sequence to enable secretion of the protein.

Alternatively, if the transformed lactic acid bacterium also contains at least one gene encoding a lytic protein under control of the salt- and pH-inducible promoter, proteins without a secretion signal sequence can be easily recovered, because the lytic protein will perforate the cell wall so that the contents including the desired protein can be released from the cell.

REFERENCES

1. U. K. Laemmli; Nature (London) 227 (1970) 680–685; Cleavage of Structural Proteins during the Assembly of the Head of Bacteriophage T4
2. J. H. Miller; (1972); Experiments in molecular genetics Cold Spring Harbor laboratory, Cold Spring Harbor N.Y. p. 352–359; Assay of β-Galactosidase Induction; Time Course of β-Galactosidase Induction
3. M. M. Bradford; Anal. Biochem. 72 (1976) 248–254; A Rapid and Sensitive Method for the Quantitation of Microgram Quantities of Protein Utilizing the Principle of Protein-Dye Binding
4. F. Sanger, S. Nicklen, and A. R. Coulson; Proc. Natl. Acad. Sci. USA 74 (1977) 5463–5467; DNA sequencing with chain-terminating inhibitors
5. M. J. Gasson; J. Bacteriol. 154 (1983) 1–9; Plasmid-Complements of *Streptococcus lactis* NCDO712 and Other Lactic Streptococci after Protoplast-Induced Curing
6. J. A. Gough, and N. E. Murray; J. Mol. Biol. 166 (1983) 1–19; Sequence Diversity among Related Genes for Recognition of Specific Targets in DNA Molecules
7. G. M. Weinstock, M. L. Berman, and T. J. Silhavy; In: T. S. Papas, M. Rosenberg, and J. G. Chirikjian (eds), Gene amplification and analysis III. Elsevier, North Holland, N.Y., (1983) pp. 27–64; Chimeric genes with β-galactosidase.
8. C. Yanisch-Perron, J. Vieira, and J. Messing; Gene 33 (1985) 103–119; Improved M13 phage cloning vectors and host strains: nucleotide sequences of the M13mp18 and pUC19 vectors
9. S. A. Lacks, P. Lopez, B. Greenberg, and M. Espinosa; J. Mol. Biol. 192 (1986) 753–765; Identification and Analysis of Genes for Tetracycline Resistance and Replication Functions in the Broad-host-range Plasmid PLS1
10. J. M. B. M. van der Vossen, D. van der Lelie, and G. Venema; Appl. Environ. Microbiol. 53 (1987) 2452–2457; Isolation and Characterization of Streptococcus cremoris Wg2-Specific Promoters
11. J. A. K. W. Kiel, J. P. M. J. Vossen, and G. Venema; Mol. Gen. Genet. 207 (1987) 294–301; A general method for the construction of *Escherichia coli* mutants by homologous recombination and plasmid segregation
12. W. R. Pearson and D. J. Lipman; Proc. Natl. Acad. Sci. USA 85 (1988) 2444–2448; Improved tools for biological sequence comparison
13. S. P. Chambers, S. E. Prior, D. A. Barstow, and N. P. Minton; Gene 68 (1988) 139–149; The pMTL nic-cloning vectors, I. Improved pUC polylinker regions to facilitate the use of sonicated DNA for nucleotide sequencing
14. K. J. Leenhouts, J. Kok, and G. Venema; Appl. Environ. Microbiol. 55 (1989) 394–400; Campbell-Like Integration of Heterologous Plasmid DNA into the Chromosome of *Lactococcus lactis* subsp. *lactis*.
15. H. Holo, and I. F. Nes; Appl. Environ. Microbiol. 55 (1989) 3119–3123; High-Frequency Transformation, by Electroporation, of *Lactococcus lactis* subsp. cremoris Grown with Glycine in Osmotically Stabilized Media
16. J. Sambrook, E. P. Fritsch, and T. Maniatis; Molecular cloning: a laboratory manual, 2nd ed. (1989); Cold Spring Harbor Laboratory Press, Cold Spring Harbor, N.Y.
17. K. J. Leenhouts, J. Kok, and G. Venema; Appl. Environ. Microbiol. 56 (1990) 2726–2735; Stability of Integrated Plasmids in the Chromosome of *Lactococcus lactis*
18. M. Itaya; Proc. Natl. Acad. Sci. USA 87 (1990) 8587–8591; Isolation and characterization of a second RNAse H (RNAse HII) of *Escherichia coli* K-12 encoded by the rnhB gene
19. E. R. Zabarovsky and G. Winberg; Nucleic Acids Res. 18 (1990) 5912; High efficiency electroporation of ligated DNA into bacteria
20. B. Mayo, J. Kok, K. Venema, W. Bockelmann, M. Teuber, H. Reinke, and G. Venema; Appl. Environ. Microbiol. 57 (1991) 38–44; Molecular Cloning and Sequence of an X-Prolyl Dipeptidyl Aminopeptidase Gene from *Lactococcus lactis* subsp. *cremoris*
21. K. J. Leenhouts, J. Kok, and G. Venema; J. Bacteriol. 173 (August 1991) 4794–4798; Replacement Recombination in *Lactococcus lactis*
22. K. J. Leenhouts, J. Kok, and G. Venema; Appl. Environ. Microbiol. 57 (September 1991) 2562–2567; Lactococcal Plasmid pWV01 as an Integration Vector for Lactococci
23. J. Vieira and J. Messing; Gene 100 (1991) 189–194; New pUC-derived cloning vectors with different selectable markers and DNA replication origins
24. M. van de Guchte, J. Kok, and G. Venema; Mol. Gen. Genet. 227 (1991) 65–71; Distance-dependent translational coupling and interference in *Lactococcus lactis*
25. M. van de Guchte, J. Kok, and G. Venema; FEMS Microbiol. Rev. 88 (1992) 73–92; Gene expression in *Lactococcus lactis*
26. C. J. Leenhouts, J. D. Marugg and C. T. Verrips (Unilever N.V./PLC); Patent Application EP-A1–0 487 159 published 27 May 1992; A food-grade vector suitable for transforming a food-grade host cell, use of said vector for transforming food-grade host cells, and use of said transformed cells in biotransformation processes
27. M. C. Sulavik, G. Tardif, and D. B. Clewell; J. Bacteriol. 174 (1992) 3577–3586; Identification of a Gene, rgg, Which Regulates Expression of Glucosyltransferase and Influences the Spp Phenotype of *Streptococcus gordonii* Challis
28. E. Maguin, P. Duwat, T. Hege, D. Ehrlich, and A. Gruss; J. Bacteriol. 174 (1992) 5633–5638; New Thermosensitive Plasmid for Gram-Positive Bacteria
29. M. van Asseldonk, A. Simons, H. Visser, W. M. de Vos, and G. Simons; J. Bacteriol. 175 (1993) 1637–1644; Cloning, Nucleotide Sequence, and Regulatory Analysis of the *Lactococcus lactis* dnaJ Gene 30. B. L. Geller, R. G. Ivey, J. E. Trempy, and B. Hettinger-Smith; J. Bacteriol. 175 (1993) 5510–5519; Cloning of a Chromosomal Gene Required for Phage Infection of *Lactococcus lactis* subsp. *lactis* C2
31. G. Buist, J. Kok, K. J. Leenhouts, M. Dabrowska, G. Venema, and A. Haandrikman; J. Bacteriol. 177 (1995) 1554–1563; Molecular Cloning and Nucleotide Sequence of the Gene Encoding the Major Peptidoglycan Hydrolase of *Lactococcus lactis*, a Muramidase Needed for Cell Separation
32. P. Le Bourgeois, M. Lautier, L. van den Berghe, M. J. Gasson, and P. Ritzenthaler; J. Bacteriol. 177 (1995) 2840–2850; Physical and Genetic Map of the *Lactococcus lactis* subsp. *cremoris* MG1363 Chromosome: Comparison with That of *Lactococcus lactis* subsp. *lactis* IL1403 Reveals a Large Genome Inversion
33. R. D. Fleischmann c.s.; Science 269 (1995) 496–512; Whole-Genome Random Sequencing and Assembly of *Haemophilus influenzae* Rd
34. G. Buist, G. Venema, J. Kok, and A. M. Ledeboer (Quest International B.V.); International Patent Application WO-A1-95/31561 published Nov. 23, 1995 (PCT); PROCESS FOR THE LYSIS OF A CULTURE OF LACTIC ACID BACTERIA BY MEANS OF A LYSIN, AND USES OF THE RESULTING LYSED CULTURE
35. A. Nauta, G. Venema, J. Kok, and A. M. Ledeboer (Quest International B.V.); International Patent Application WO-A1-95/31562 published Nov. 23, 1995 (PCT); PROCESS FOR INHIBITING THE GROWTH OF A CULTURE OF LACTIC ACID BACTERIA, AND OPTIONALLY LYSING THE BACTERIAL CELLS, AND USES OF THE RESULTING LYSED CULTURE
36. A. Nauta, G. Venema, J. Kok, and A. M. Ledeboer (Quest International B.V.); International Patent Application WO-A1-95/31563 published Nov. 23, 1995 (PCT); COMPLEX INDUCIBLE PROMOTER SYSTEM DERIVABLE FROM A PHAGE OF A LACTIC ACID BACTERIUM (LAB), AND ITS USE IN A LAB FOR PRODUCTION OF A DESIRED PROTEIN
37. J. Law, G. Buist, A. Haandrikman, J. Kok, G. Venema, and K. Leenhouts; J. Bacteriol. 177 (1995) 7011–7018; A System to Generate Chromosomal Mutations in *Lactococcus lactis* Which Allows Fast Analysis of Targeted Genes.
38. D.van Sinderen, H. Karsens, J. Kok, P. Terpstra, M. H. J. Ruiters, G. Venema, and A. Nauta; Mol. Microbiol. 19 (No.6) (1996) 1343–1355; Sequence analysis and molecular characterization of the temperate lactococcal bacteriophage r1t
39. K. Leenhouts, G. Buist, A. Bolhuis, A. ten Berge, J. Kiel, I. Mierau, M. Dabrowska, G. Venema, and J. Kok; Mol. Gen. Genet. (1996, Accepted for publication); A general system for generating unlabelled gene replacements in bacterial chromosomes
=K. J. Leenhouts, G. Buist, A. Bolhuis, A. ten Berge, J. Kiel, I. Mirau, M. Dabrowska, G. Venema, and J. Kok; Mol. Gen. Genet. 253 (1996) 217–224; A general system for generating unlabeled gene replacements in bacterial chromosomes (Published after Sep. 5, 1996)
40. K. J. Leenhouts, A. Bolhuis, G. Venema, and J. Kok; (Submitted for publication 1996); Construction of a food-grade multiple copy integration system for *Lactococcus lactis*.
41. S. F. Altschul, W. Gish, W. Miller, E. W. Myers, and D. J. Lipman; J. Mol. Biol. 215 (1990) 403–410; Basic local alignment search tool
42. M. Cocaign-Bousquet, C. Garrigues, L. Novak, N. D. Lindley, and P. Loubiere; J. Appl. Bacteriol. 79 (1995) 108–116; Rational development of a simple synthetic medium for the sustained growth of *Lactococcus lactis*
43. B. M. Hersh, F. T. Farooq, D. N. Barstad, D. L. Blankenhorn, and J. L. Slonczewski; J. Bacteriol. 178; (1996) 3978–3981; A glutamate-dependent acid resistance gene in *Escherichia coli*
44. T. Kaneko, S, Sato, H. Kotani, A. Tanaka, E. Asamizu, Y. Nakamura, N. Miyajima, M. Hirosawa, M. Sugiura, S. Sasamoto, T. Kimura, T. Hosouchi, A. Matsuno, A. Muraki, N. Nakazaki, K. Naruo, S. Okumura, S. Shimpo, C. Takeuchi, T. Wada, A. Watanabe, M. Yamada, M. Yasuda, and S. Tabata; J. DNA Res. 3 (1996) 109–136; Sequence analysis of the genome of the unicellular cyanobacterium Synechocystis sp. strain PCC6803. II. Sequence determination of the entire genome and assignment of potential protein-coding regions
45. P. Klein, M. Kanehisa, and C. DeLisi; Biochim. Biophys. Acta 815 (1985) 468–476; The detection and classification of membrane spanning proteins
46. S. Meng, and G.N. Bennett; J. Bacteriol. 174 (1992) 2659–2669; Nucleotide sequence of the *Escherichia coli* cad operon: a system for neutralization of low extracellular pH
47. S. R. Waterman, and P. L. C. Small; Mol. Microbiol. 21 (1996) 925–940; Identification of $\sigma^S$-dependent genes associated with the stationary-phase acid-resistance phenotype of *Shigella flexneri*

What is claimed is:

1. A salt-inducible promoter obtained from a lactic acid bacterium, in isolation from the coding sequence which is normally controlled by said promoter in a wild-type lactic acid bacterium.

2. A salt-inducible promoter according to claim 1, which comprises the polynucleotide 1482-1925 of SEQ. ID. NO: 10.

3. A salt-inducible promoter according to claim 1, which comprises the polynucleotide 1482-2068 of SEQ. ID. NO: 10.

4. A salt-inducible promoter according to claim 1, which comprises the polynucleotide 1-2068 of SEQ. ID. NO: 10.

5. A salt-inducible promoter according to claim 4, which additionally comprises part of the ORF X gene together forming polynucleotide 1-2426 of SEQ. ID. NO: 10.

6. A salt-inducible promoter, which exerts promoter activity for salt-induction of gene expression and comprises a DNA sequence that hybridizes with a polynucleotide selected from the group consisting of
   (a) polynucleotide 1482-1925 of SEQ. ID. NO: 10 followed by a promoter functional in a lactic acid bacterium,
   (b) polynucleotide 1482-2068 of SEQ. ID. NO: 10,
   (c) polynucleotide 1-2068 of SEQ. ID. NO: 10, and
   (d) polynucleotide 1-2426 of SEQ. ID. NO: 10.

7. A DNA fragment encoding a polypeptide that regulates a salt-inducible promoter active in a lactic acid bacterium, which comprises the polynucleotide 1095-1925 of SEQ. ID. NO: 10, or a polynucleotide that
   (a) encodes the same polypeptide as said polynucleotide 1095-1925 of SEQ. ID. NO: 10, or
   (b) encodes a polypeptide with gadR regulatory activity and hybridizes with said polynucleotide 1095-1925 of SEQ. ID. NO: 10.

8. A recombinant vector comprising a salt-inducible promoter selected from the group consisting of:
   (1) a salt-inducible promoter obtained from a lactic acid bacterium, in isolation from the coding sequence which is normally controlled by said promoter in a wild-type lactic acid bacterium;
   (2) a salt-inducible promoter according to item (1), which comprises the polynucleotide 1482-1925 of SEQ. ID. NO: 10;
   (3) a salt-inducible promoter according to item (1), which comprises the polynucleotide 1482-2068 of SEQ. ID. NO: 10;
   (4) a salt-inducible promoter according to item (1), which comprises the polynucleotide 1-2068 of SEQ. ID. NO: 10;
   (5) a salt-inducible promoter according to item (1), which comprises the polynucleotide 1-2426 of SEQ. ID. NO: 10;
   (6) a salt-inducible promoter, which exerts promoter activity for salt-induction of gene expression and comprises a DNA sequence which hybridizes with a polynucleotide selected from the group consisting of
      (a) polynucleotide 1482-1925 of SEQ. ID. NO: 10 followed by a promoter functional in a lactic acid bacterium,
      (b) polynucleotide 1482-2068 of SEQ. ID. NO: 10,
      (c) polynucleotide 1-2068 of SEQ. ID. NO: 10, and
      (d) polynucleotide 1-2426 of SEQ. ID. NO: 10; and
   (7) a salt-inducible promoter comprising a first DNA fragment that regulates a salt-inducible promoter active in a lactic acid bacterium, which first DNA fragment comprises the polynucleotide 1095-1925 of SEQ. ID. NO: 10 in combination with a second DNA fragment, which comprises the polynucleotide 1926-2000 of SEQ. ID. NO: 10.

9. A transformed lactic acid bacterium comprising a salt-inducible promoter from a lactic acid bacterium, in isolation from the coding sequences which is normally controlled by said promoter in a wild-type lactic acid bacterium;
   or a salt-inducible promoter, which comprises the polynucleotide 1482-1925 of SEQ. ID. NO: 10;
   or a salt-inducible promoter which exerts promoter activity for salt-induction of gene expression and hybridizes with a polynucleotide selected from the group consisting of
      (a) polynucleotide 1482-1925 of SEQ. ID. NO: 10 followed by a promoter functional in a lactic acid bacterium,
      (b) polynucleotide 1482-2068 of SEQ. ID. NO: 10,
      (c) polynucleotide 1-2068 of SEQ. ID. NO: 10, and
      (d) polynucleotide 1-2426 of SEQ. ID. NO: 10;
   or a salt-inducible promoter comprising a first DNA fragment that regulates a salt-inducible promoter active in a lactic acid bacterium, which first DNA fragment comprises the polynucleotide 1095-1925 of SEQ. ID. NO: 10 in combination with a second DNA fragment, which comprises the polynucleotide 1926-2000 of SEQ. ID. NO: 10.

10. A process for the production of a desired protein by a transformed lactic acid bacterium according to claim 9, comprising producing said desired protein or a precursor thereof under control of said salt-inducible promoter in a culture of said transformed lactic acid bacterium.

11. A process according to claim 10, in which the desired protein is secreted by the lactic acid bacterium due to the presence of a DNA fragment fused to the gene encoding the desired protein and effecting secretion of the desired protein or a precursor thereof.

12. A process according to claim 10, in which the action of the salt-inducible promoter is enhanced by allowing the pH of the medium in which the lactic acid bacterium is cultured to decrease to a value of about 4 to about 4.5.

13. A process according to claim 10, in which the action of the salt-inducible promoter is enhanced by incorporating a sufficient amount of glutamate or glutamic acid in medium in which the lactic acid bacterium is cultured.

14. A process according to claim 13, in which the amount of glutamate or glutamic acid in the medium is about 50 mM.

15. A process according to claim 10 wherein the desired protein is a lytic protein causing lysis of the bacterium so that the contents of the bacterium is released.

16. A process according to claim 10 wherein the desired protein is an enzyme involved in flavour formation.

17. A process according to claim 10 wherein the desired protein is a protein having a function in a cheese production process or an enzyme involved in cheese flavour formation.

18. A process according to claim 17, in which the protein is chymosin or a precursor thereof.

* * * * *

SEQUENCE LISTING

<160> NUMBER OF SEQ ID NOS: 25

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: primer
      NS3-1
<220> FEATURE:
<221> NAME/KEY: primer_bind
<222> LOCATION: (1)..(19)

<400> SEQUENCE: 1
cattgagata atcagatac                                                19

```
<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: primer
      NS3-2
<220> FEATURE:
<221> NAME/KEY: primer_bind
<222> LOCATION: (1)..(16)

<400> SEQUENCE: 2
gcagagattg gggaag                                                    16

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: primer
      NS3-5
<220> FEATURE:
<221> NAME/KEY: primer_bind
<222> LOCATION: (1)..(34)

<400> SEQUENCE: 3
ggggccctct cttatgtgtt aaattttcag gcgc                                34

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: primer
      NS3-6
<220> FEATURE:
<221> NAME/KEY: primer_bind
<222> LOCATION: (1)..(18)

<400> SEQUENCE: 4
atatcgttca cgttttcc                                                  18

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: primer
      NS3-7
<220> FEATURE:
<221> NAME/KEY: primer_bind
<222> LOCATION: (1)..(43)

<400> SEQUENCE: 5
gcgatatcca gtacttcatc atacctcctt atatttatga ttg                      43

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: primer
      NS3-8

<400> SEQUENCE: 6
gcgagctcag atctgagcgt tgtataagct tttatgtctt tc                       42

<210> SEQ ID NO 7
<211> LENGTH: 16
```

```
<212> TYPE: DNA
<213> ORGANISM: Artificial Sequence
<220> FEATURE:
<223> OTHER INFORMATION: Description of Artificial Sequence: primer
      NS3-9
<220> FEATURE:
<221> NAME/KEY: primer_bind
<222> LOCATION: (1)..(16)

<400> SEQUENCE: 7
gtttgactga cccaac                                              16

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: primer
      NS3-10
<220> FEATURE:
<221> NAME/KEY: primer_bind
<222> LOCATION: (1)..(17)

<400> SEQUENCE: 8
ccgcttcaat ggttttg                                             17

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: primer
      NS3-11
<220> FEATURE:
<221> NAME/KEY: primer_bind
<222> LOCATION: (1)..(38)

<400> SEQUENCE: 9
cagtcaaaac cattgaagcg gttaatgcga aaaaaccg                      38

<210> SEQ ID NO 10
<211> LENGTH: 2989
<212> TYPE: DNA
<213> ORGANISM: Artificial Sequence
<220> FEATURE:
<223> OTHER INFORMATION: Description of Artificial Sequence: genomic
      DNA of NS3 locus
<220> FEATURE:
<221> NAME/KEY: mat_peptide
<222> LOCATION: (3)..(500)
<223> OTHER INFORMATION: C-terminus of rnhB3
<220> FEATURE:
<221> NAME/KEY: mat_peptide
<222> LOCATION: (1095)..(1922)
<223> OTHER INFORMATION: rggL
<220> FEATURE:
<221> NAME/KEY: mat_peptide
<222> LOCATION: (2069)..(2989)
<223> OTHER INFORMATION: N-terminus of lacZ

<400> SEQUENCE: 10
ctgcagtaat tttgccaaag aattgtaaaa ttcgtggttt gaatgatagt aaaaaagtgc    60
caaaatcaaa gcatcatgct attctatctg aaattcaaga aaaagcgcta gcgattggag   120
ttggaattgt tgatgccgaa aaaattgatg aagtaaatat ttatgaggcg acaaaaattg   180
caatgattca ggcagtatca aaattatctc ttaaacctga acatctctta atagatgcga   240
tggttttaga tttgccccatt gctcagacga aaatcattca tggagatgct cgttcagctt   300
caattgcggc cgcatcaatt gtagctaaag tgactcgtga tgaaatgatg aaggatttcg   360
```

-continued

```
ctttagaatt tccagaatat gattttgaac ataatgcagg ctatggaaca gcaaaacatc   420
ttgcagctct gacaaaatat ggtatcacaa gaattcatcg gaaatcctat gaaccaatta   480
aatcgatggt caatttcaaa tagtagatta tgtaagtaaa aaaaggaaaa cgtgaacgat   540
atttggtcac gttttttttgc tgacaagtct gtcagtaatt attttcaaag gtttcaaaaa   600
tatagtctag taatttgcta gactaatctt ctgtttttta ataataaact aattttttgt   660
taatctaaat gacaaaatta ataagcagag ttttttataa aattagctac ttataaaaaa   720
tttgaaattg gtatagttaa atctgttata atttccaata tttttttaata ataattattt   780
taacaaaata cttatatcaa aactctttca aagtatataa tgagcgttgt ataagctttt   840
atgtctttct atatcaactt ttaatagaaa tataaagtaa tataaatgtt tttataataa   900
attatgtgag atatatttt ttgtccgtac tggtatagat ttgacgatta agtcttaaat   960
aagttataat ctcaattgcg taatttctta aatacagaaa taacaactac attggtagac  1020
tgattaaaaa gtgtacttga tgaactgtta taaaccttaa aaaaataaaa ataatagttt  1080
ggggggatgtt aaagatgtat aaaaaatatg gagattgttt taaaaagttg cgaaaccaaa  1140
agaatttagg gttatcatac tttagtaaac ttggaataga ccgttcaaat atatctagat  1200
ttgaacatgg aaaatgtatg atgagttttg agcgtataga tttgatgtta gaagaaatgc  1260
aagttccgtt atctgagtac gaattgattg taaataattt tatgccgaat ttccaagaat  1320
tttttatatt agaattggaa aaagctgaat ttagccaaaa tcgagataaa ataaaagagt  1380
tgtattctga ggtcaaagaa acgggaatc atttactgac ggttaccgtg aaaacgaagc  1440
ttgggaatat aagtcagaca gaagttaaag aaattgaagc ttatctttgc aatattgaag  1500
agtggggata ttttgaactt actttatttt attttgtatc tgattatctc aatgtcaatc  1560
aattagaatt gctgcttttt aattttgata aagatgtga aaattactgt agagtcttaa  1620
aatatagaag gagactattg caaatagcct ataaaagtgt tgcgatatac gcggctaaag  1680
gagaaagaaa aaaagccgaa atatttttag aaatgactaa aaaatatcga actgtgggag  1740
tcgatttata ttcagaagta ttaagacatc ttgctagagc tatcattatt tttaattttg  1800
aaaatgcaga gattggggaa gaaaaaataa attatgctct tgagattttg gaagaatttg  1860
gaggaaagaa gataaaagaa ttctatcaga ataaaatgga aaagtatttg aaaaggtcaa  1920
tttagtctct tttgagctgt tgctttaaag caacagctca aaagagattt tctttattct  1980
agagcatata ctagagggtg aagataggtt gtctgaagca ttataacttg tcttttaaaa  2040
aattcaatca taaatataag gaggtatgat gaatcaaaaa aaattatcat tattcggttt  2100
tttcgcatta accgcttcaa tggttttgac tgtctatgag tatccgactt ttgccacgtc  2160
aaaattacat ttggtgttct ttttacttct cggaggacta ctatggtttt tgcctgtagc  2220
gctctgcgca gcagaaatgg cgacggttga aggctgaaaa atggtggaa tctttagttg  2280
ggtcagtcaa actttaggtg agcgctttgg ttttgcagcc atatttttc agtggttcca  2340
aattacagta ggttttgtca ctatgatcta tttcattta ggggccctct cttatgtgtt  2400
aaatttcag gcgctcaata cagatccatt gataaaattt attggtttac taatcatttt  2460
ttggggattg acttttctc aattaggtgg gacgcaacgg actgccaaat tagtaaaagc  2520
tggctttgta gttggaatag tgattccatc ggttatcttg ttttggattag cagcggcata  2580
ctttatcgga ggcaatccta tagaaatacc aattaacagc catgcttttg taccagattt  2640
ttcacaggta tcaactttag tagttttttgt ttctttat ctggcttata tgggggtaga  2700
agcctcagct tcacatatta atgaacttga aaatccaaaa cgaaattatc ccttagcaat  2760
```

```
gatttttatta gtaattttgg ctatttctttt agatgccata ggtggatttt ctgtagcagc    2820
agttattcct caaaagagt tatcattaag tgcaggggta atccaaactt ttcaaacgtt    2880
aatcttacat tttaatcatc atttgggatg gttagttaaa gtgattgcac taatgattgc    2940
ctttggggtt atgggagaag tgagttcatg ggttgttggt ccttctaga    2989
```

<210> SEQ ID NO 11
<211> LENGTH: 276
<212> TYPE: PRT
<213> ORGANISM: L. lactis MG1363

<400> SEQUENCE: 11

```
Met Tyr Lys Lys Tyr Gly Asp Cys Phe Lys Lys Leu Arg Asn Gln Lys
  1               5                  10                  15

Asn Leu Gly Leu Ser Tyr Phe Ser Lys Leu Gly Ile Asp Arg Ser Asn
             20                  25                  30

Ile Ser Arg Phe Glu His Gly Lys Cys Met Met Ser Phe Glu Arg Ile
         35                  40                  45

Asp Leu Met Leu Glu Glu Met Gln Val Pro Leu Ser Glu Tyr Glu Leu
     50                  55                  60

Ile Val Asn Asn Phe Met Pro Asn Phe Gln Glu Phe Phe Ile Leu Glu
 65                  70                  75                  80

Leu Glu Lys Ala Glu Phe Ser Gln Asn Arg Asp Lys Ile Lys Glu Leu
                 85                  90                  95

Tyr Ser Glu Val Lys Glu Thr Gly Asn His Leu Leu Thr Val Thr Val
            100                 105                 110

Lys Thr Lys Leu Gly Asn Ile Ser Gln Thr Glu Val Lys Glu Ile Glu
        115                 120                 125

Ala Tyr Leu Cys Asn Ile Glu Glu Trp Gly Tyr Phe Glu Leu Thr Leu
    130                 135                 140

Phe Tyr Phe Val Ser Asp Tyr Leu Asn Val Asn Gln Leu Glu Leu Leu
145                 150                 155                 160

Leu Phe Asn Phe Asp Lys Arg Cys Glu Asn Tyr Cys Arg Val Leu Lys
                165                 170                 175

Tyr Arg Arg Arg Leu Leu Gln Ile Ala Tyr Lys Ser Val Ala Ile Tyr
            180                 185                 190

Ala Ala Lys Gly Glu Arg Lys Lys Ala Glu Asn Ile Leu Glu Met Thr
        195                 200                 205

Lys Lys Tyr Arg Thr Val Gly Val Asp Leu Tyr Ser Glu Val Leu Arg
    210                 215                 220

His Leu Ala Arg Ala Ile Ile Ile Phe Asn Phe Glu Asn Ala Glu Ile
225                 230                 235                 240

Gly Glu Glu Lys Ile Asn Tyr Ala Leu Glu Ile Leu Glu Glu Phe Gly
                245                 250                 255

Gly Lys Lys Ile Lys Glu Phe Tyr Gln Asn Lys Met Glu Lys Tyr Leu
            260                 265                 270

Lys Arg Ser Ile
        275
```

<210> SEQ ID NO 12
<211> LENGTH: 297
<212> TYPE: PRT
<213> ORGANISM: S. gorodnii

```
<400> SEQUENCE: 12

Met Leu Ile Val Lys Ser Ser Gly Lys Ile Leu Lys Ile Ile Arg Glu
  1               5                  10                  15

Ser Lys Asn Met Ser Leu Lys Glu Val Ala Ala Gly Asp Ile Ser Val
             20                  25                  30

Ala Gln Leu Ser Arg Tyr Glu Arg Gly Ile Ser Ser Leu Thr Val Asp
         35                  40                  45

Ser Phe Tyr Ser Cys Leu Arg Asn Met Ser Val Ser Leu Ala Glu Phe
     50                  55                  60

Gln Tyr Val Tyr His Asn Tyr Arg Glu Ala Asp Asp Val Val Leu Ser
 65                  70                  75                  80

Gln Lys Leu Ser Glu Ala Gln Arg Glu Asn Asn Ile Val Lys Leu Glu
                 85                  90                  95

Ser Ile Leu Ala Gly Ser Glu Ala Met Ala Gln Glu Phe Pro Glu Lys
            100                 105                 110

Lys Asn Tyr Lys Leu Asn Thr Ile Val Ile Arg Ala Thr Leu Thr Ser
        115                 120                 125

Cys Asn Pro Asp Tyr Gln Val Ser Lys Gly Asp Ile Glu Phe Leu Thr
    130                 135                 140

Asp Tyr Leu Phe Ser Val Glu Glu Trp Gly Arg Tyr Glu Leu Trp Leu
145                 150                 155                 160

Phe Thr Asn Ser Val Asn Leu Leu Thr Leu Glu Thr Leu Glu Thr Phe
                165                 170                 175

Ala Ser Glu Met Ile Asn Arg Thr Gln Phe Tyr Asn Asn Leu Pro Glu
            180                 185                 190

Asn Arg Arg Ile Ile Lys Met Leu Leu Asn Val Val Ser Ala Cys
        195                 200                 205

Ile Glu Asn Asn His Leu Gln Val Ala Met Lys Phe Leu Asn Tyr Ile
    210                 215                 220

Asp Asn Thr Lys Ile Pro Glu Thr Asp Leu Tyr Asp Arg Val Leu Ile
225                 230                 235                 240

Lys Tyr His Lys Ala Leu Tyr Ser Tyr Lys Val Gly Asn Pro His Ala
                245                 250                 255

Arg His Asp Ile Glu Gln Cys Leu Ser Thr Phe Glu Tyr Leu Asp Ser
            260                 265                 270

Phe Gly Val Ala Arg Lys Leu Lys Glu Gln Phe Glu Arg Ile Gln Leu
        275                 280                 285

Thr Val Val Ala Asp Leu Gln Ile Glu
    290                 295

<210> SEQ ID NO 13
<211> LENGTH: 97
<212> TYPE: PRT
<213> ORGANISM: L. lactis C2

<400> SEQUENCE: 13

Met Pro Tyr Lys Arg Tyr Gly Glu Ile Phe Lys Lys Leu Arg Glu Gln
  1               5                  10                  15

Lys Asn Phe Ser Leu Ser His Phe Ser Glu Ile Gly Ile Ser Lys Ala
             20                  25                  30

Ser Leu Ser Arg Phe Glu Leu Gly Gln Thr Met Ile Ser Phe Glu Arg
         35                  40                  45

Leu Asp Ser Ala Leu Gln Glu Met Asn Val Thr Leu Ala Glu Tyr Glu
     50                  55                  60
```

```
His Phe Ile Asn Asn Phe Ser Met Asp Tyr Lys Glu Glu Phe Leu Glu
 65                  70                  75                  80

Asp Ile Ile Leu Ala Asp Ile Ala Asp Asp Val Asp Lys Leu His Lys
                 85                  90                  95

Leu
```

<210> SEQ ID NO 14
<211> LENGTH: 166
<212> TYPE: PRT
<213> ORGANISM: L. lactis

<400> SEQUENCE: 14

```
Ala Val Ile Leu Pro Lys Asn Cys Lys Ile Arg Gly Leu Asn Asp Ser
  1               5                  10                  15

Lys Lys Val Pro Lys Ser Lys His His Ala Ile Leu Ser Glu Ile Gln
                 20                  25                  30

Glu Lys Ala Leu Ala Ile Gly Val Gly Ile Val Asp Ala Glu Lys Ile
             35                  40                  45

Asp Glu Val Asn Ile Tyr Glu Ala Thr Lys Ile Ala Met Ile Gln Ala
         50                  55                  60

Val Ser Lys Leu Ser Leu Lys Pro Glu His Leu Leu Ile Asp Ala Met
 65                  70                  75                  80

Val Leu Asp Leu Pro Ile Ala Gln Thr Lys Ile Ile His Gly Asp Ala
                 85                  90                  95

Arg Ser Ala Ser Ile Ala Ala Ser Ile Val Ala Lys Val Thr Arg
            100                 105                 110

Asp Glu Met Met Lys Asp Phe Ala Leu Glu Phe Pro Glu Tyr Asp Phe
            115                 120                 125

Glu His Asn Ala Gly Tyr Gly Thr Ala Lys His Leu Ala Ala Leu Thr
        130                 135                 140

Lys Tyr Gly Ile Thr Arg Ile His Arg Lys Ser Tyr Glu Pro Ile Lys
145                 150                 155                 160

Ser Met Val Asn Phe Lys
                165
```

<210> SEQ ID NO 15
<211> LENGTH: 161
<212> TYPE: PRT
<213> ORGANISM: Vibrio cholera (U30472)

<400> SEQUENCE: 15

```
Pro Asn Arg Pro Ile Met Gly Leu Asn Asp Ser Lys Lys Leu Ser Glu
  1               5                  10                  15

Lys Lys Arg Leu Ala Leu Phe Pro Glu Ile Gln Val Lys Ala Leu Ala
                 20                  25                  30

Trp Ala Val Gly Arg Cys Ser Pro Gln Glu Ile Asp Glu Leu Asn Ile
             35                  40                  45

Phe Gln Ala Thr Met Val Ala Met Gln Arg Ala Val Ala Gly Leu Arg
         50                  55                  60

Ile Gln Pro Asp Leu Val Leu Ile Asp Gly Asn Lys Ile Pro Lys Leu
 65                  70                  75                  80

Pro Met Glu Ala Gln Ala Val Val Lys Gly Asp Leu Arg Val Ala Gln
                 85                  90                  95

Ile Ser Ala Ala Ser Ile Ile Ala Lys Val Ile Arg Asp Gln Glu Met
            100                 105                 110
```

```
Glu Ala Leu Asp Lys Gln Tyr Pro Gln Phe Gly Phe Ala Asn His Lys
            115                 120                 125

Gly Tyr Pro Thr Ala Ala His Phe Ala Ala Ile Glu Gln His Gly Val
        130                 135                 140

Ile Glu Gln His Arg Lys Ser Phe Gly Pro Val Lys Arg Ala Leu Gly
145                 150                 155                 160

Glu

<210> SEQ ID NO 16
<211> LENGTH: 213
<212> TYPE: PRT
<213> ORGANISM: E. coli

<400> SEQUENCE: 16

Met Ile Glu Phe Val Tyr Pro His Thr Gln Leu Val Ala Gly Val Asp
  1               5                  10                  15

Glu Val Gly Arg Gly Pro Leu Val Gly Ala Val Thr Ala Ala Val
             20                  25                  30

Ile Leu Asp Pro Ala Arg Pro Ile Ala Gly Leu Asn Asp Ser Lys Lys
         35                  40                  45

Leu Ser Glu Lys Arg Arg Leu Ala Leu Tyr Glu Glu Ile Lys Glu Lys
 50                  55                  60

Ala Leu Ser Trp Ser Leu Gly Arg Ala Glu Pro His Glu Ile Asp Glu
 65                  70                  75                  80

Leu Asn Ile Leu His Ala Thr Met Leu Ala Met Gln Arg Ala Val Ala
                 85                  90                  95

Gly Leu His Ile Ala Pro Glu Tyr Val Leu Ile Asp Gly Asn Arg Cys
            100                 105                 110

Pro Lys Leu Pro Met Pro Ala Met Ala Val Val Lys Gly Asp Ser Arg
        115                 120                 125

Val Pro Glu Ile Ser Ala Ala Ser Ile Leu Ala Lys Val Thr Arg Asp
    130                 135                 140

Ala Glu Met Ala Ala Leu Asp Ile Val Phe Pro Gln Tyr Gly Phe Ala
145                 150                 155                 160

Gln His Lys Gly Tyr Pro Thr Ala Phe His Leu Glu Lys Leu Ala Glu
                165                 170                 175

His Gly Ala Thr Glu His His Arg Arg Ser Phe Gly Pro Val Lys Arg
            180                 185                 190

Ala Leu Gly Thr Cys Val Leu Ile Leu Val Ser Arg Leu Ser Lys Pro
        195                 200                 205

Glu Ser Glu Asp Val
    210

<210> SEQ ID NO 17
<211> LENGTH: 197
<212> TYPE: PRT
<213> ORGANISM: Haemophilus influenza

<400> SEQUENCE: 17

Met Phe Glu Tyr Pro Gln Gly Tyr Lys Leu Ile Ala Gly Val Asp Glu
  1               5                  10                  15

Val Gly Arg Gly Pro Leu Val Gly Ala Val Thr Ala Ala Val Ile
             20                  25                  30

Leu Asp Pro His Asn Pro Ile Glu Gly Leu Ala Asp Ser Lys Lys Leu
         35                  40                  45
```

```
Ser Glu Lys Lys Arg Leu Ala Leu Ala Glu Glu Ile Lys Glu Lys Ala
    50                  55                  60

Arg Ala Trp Ala Leu Gly Arg Ala Glu Ala Asp Glu Ile Asp Glu Ile
65                  70                  75                  80

Asn Ile Leu Gln Ala Ser Leu Leu Ala Met Thr Arg Ala Val Lys Ser
                85                  90                  95

Leu Lys Ile Gln Pro His Phe Val Leu Ile Asp Gly Asn Lys Ile Pro
            100                 105                 110

Lys Asp Leu Ala Ile Pro Ala Gln Ala Val Val Lys Gly Asp Ser Leu
        115                 120                 125

Val Ala Glu Ile Ser Ala Ala Ser Ile Leu Ala Lys Val Ala Arg Asp
130                 135                 140

Gln Glu Met Glu Glu Leu Asp Lys Gln Tyr Pro Glu Tyr Ala Phe Ala
145                 150                 155                 160

Gln His Lys Gly Tyr Pro Thr Lys Leu His Leu Glu Lys Leu Ala Glu
                165                 170                 175

Leu Gly Ala Leu Pro Gln His Arg Arg Ser Phe Ala Pro Val Lys Lys
            180                 185                 190

Ala Leu Glu Gln Phe
        195
```

<210> SEQ ID NO 18
<211> LENGTH: 360
<212> TYPE: DNA
<213> ORGANISM: Artificial Sequence
<220> FEATURE:
<223> OTHER INFORMATION: Description of Artificial Sequence: clone
      pNS3PR
<220> FEATURE:
<221> NAME/KEY: mat_peptide
<222> LOCATION: (92)..(283)
<223> OTHER INFORMATION: C-terminus of ORFX
<220> FEATURE:
<221> NAME/KEY: mat_peptide
<222> LOCATION: (297)..(359)
<223> OTHER INFORMATION: lytP

<400> SEQUENCE: 18

```
tctagagcat atactagagg gtgaagatag gttgtctgaa gcattataac ttgtcttta      60 aaaaattcaa tcataaatat aaggaggtat gatgaagtac tggatactta tcaatgatga   120
accttggttt gtcggaaaag atgtagcaat tgctattggt tacaagaatt tcagggatgc   180
tttgaaatct catgtaaaag acaaatataa gagggagtcg gacagcagtg attggttcaa   240
cgacaatata ttattggaaa cgaactgcat aaaaaataaa aataggaga agaacatga     300 aaacattttt taaagatatg gcagaacgtg ccattaaaac atttgcacaa gcaatgattg   360
```

<210> SEQ ID NO 19
<211> LENGTH: 180
<212> TYPE: DNA
<213> ORGANISM: Artificial Sequence
<220> FEATURE:
<223> OTHER INFORMATION: Description of Artificial Sequence: clone
      pNS3AL3
<220> FEATURE:
<221> NAME/KEY: mat_peptide
<222> LOCATION: (92)..(154)
<223> OTHER INFORMATION: truncated ORFX

```
<400> SEQUENCE: 19
tctagagcat atactagagg gtgaagatag gttgtctgaa gcattataac ttgtctttta       60
aaagattcaa tcataaatat aaggaggtat gatgaagtac ttattatatt ttgtaatctt      120
tagaaaggta attatttatg ccagtatcac gtgttaaagt taaaaataga catttaaaaa      180

<210> SEQ ID NO 20
<211> LENGTH: 179
<212> TYPE: DNA
<213> ORGANISM: Artificial Sequence
<220> FEATURE:
<223> OTHER INFORMATION: Description of Artificial Sequence: clone
      pNS3AL3
<220> FEATURE:
<221> NAME/KEY: mat_peptide
<222> LOCATION: (92)..(112)
<223> OTHER INFORMATION: truncated ORFX
<220> FEATURE:
<221> NAME/KEY: mat_peptide
<222> LOCATION: (137)..(178)
<223> OTHER INFORMATION: N-terminus of acmA

<400> SEQUENCE: 20
tctagagcat atactagagg gtgaagatag gttgtctgaa gcattataac ttgtctttta       60
aaagattcaa tcataaatat aaggaggtat gatgaagtct tattatattt tgtaatcttt      120
agaaaggtaa ttatttatgc cagtatcacg tgttaaagtt aaaaatagac atttaaaaa       179

<210> SEQ ID NO 21
<211> LENGTH: 5565
<212> TYPE: DNA
<213> ORGANISM: Artificial Sequence
<220> FEATURE:
<223> OTHER INFORMATION: Description of Artificial Sequence: genomic
      DNA of NS3 locus containing gadRCB
<220> FEATURE:
<221> NAME/KEY: mat_peptide
<222> LOCATION: (3)..(500)
<223> OTHER INFORMATION: C-terminus of rnhB
<220> FEATURE:
<221> NAME/KEY: mat_peptide
<222> LOCATION: (1095)..(1922)
<223> OTHER INFORMATION: rggL = gadR
<220> FEATURE:
<221> NAME/KEY: mat_peptide
<222> LOCATION: (2069)..(3577)
<223> OTHER INFORMATION: orfX = gadC
<220> FEATURE:
<221> NAME/KEY: mat_peptide
<222> LOCATION: (3600)..(4997)
<223> OTHER INFORMATION: gadB
<220> FEATURE:
<221> NAME/KEY: mat_peptide
<222> LOCATION: Complement((5078)..(5563))
<223> OTHER INFORMATION: C-terminus of ORF in opposite direction

<400> SEQUENCE: 21
ctgcagtaat tttgccaaag aattgtaaaa ttcgtggttt gaatgatagt aaaaaagtgc       60
caaaatcaaa gcatcatgct attctatctg aaattcaaga aaaagcgcta gcgattggag      120
ttggaattgt tgatgccgaa aaaattgatg aagtaaatat ttatgaggcg acaaaaattg      180
caatgattca ggcagtatca aaattatctc ttaaacctga acatctctta atagatgcga      240
tggttttaga tttgcccatt gctcagacga aaatcattca tggagatgct cgttcagctt      300
caattgcggc cgcatcaatt gtagctaaag tgactcgtga tgaaatgatg aaggatttcg      360
ctttagaatt tccagaatat gattttgaac ataatgcagg ctatggaaca gcaaaacatc      420
ttgcagctct gacaaaatat ggtatcacaa gaattcatcg gaaatcctat gaaccaatta      480
```

-continued

```
aatcgatggt caatttcaaa tagtagatta tgtaagtaaa aaaaggaaaa cgtgaacgat      540
atttggtcac gttttttttgc tgacaagtct gtcagtaatt attttcaaag gtttcaaaaa     600
tatagtctag taatttgcta gactaatctt ctgttttttta ataataaact aattttttgt     660
taatctaaat gacaaaatta ataagcagag ttttttataa aattagctac ttataaaaaa     720
tttgaaattg gtatagttaa atctgttata atttccaata ttttttaata ataattattt     780
taacaaaata cttatatcaa aactctttca agtatataa tgagcgttgt ataagctttt      840
atgtctttct atatcaactt ttaatagaaa tataaagtaa tataaatgtt tttataataa     900
attatgtgag atatatttt ttgtccgtac tggtatagat ttgacgatta agtcttaaat      960
aagttataat ctcaattgcg taatttctta aatacagaaa taacaactac attggtagac    1020
tgattaaaaa gtgtacttga tgaactgtta taaaccttaa aaaataaaa ataatagttt     1080 gggggatgtt aaagatgtat aaaaaatatg gagattgttt taaaaagttg cgaaaccaaa    1140
agaatttagg gttatcatac tttagtaaac ttggaataga ccgttcaaat atatctagat    1200
ttgaacatgg aaaatgtatg atgagttttg agcgtataga tttgatgtta gaagaaatgc    1260
aagttccgtt atctgagtac gaattgattg taaataattt tatgccgaat ttccaagaat    1320
tttttatatt agaattggaa aaagctgaat ttagccaaaa tcgagataaa ataaaagagt    1380
tgtattctga ggtcaaagaa acggggaatc atttactgac ggttaccgtg aaaacgaagc    1440
ttgggaatat aagtcagaca gaagttaaag aaattgaagc ttatctttgc aatattgaag    1500
agtggggata ttttgaactt actttatttt attttgtatc tgattatctc aatgtcaatc    1560
aattagaatt gctgcttttt aattttgata aagatgtga aaattactgt agagtcttaa     1620
aatatagaag gagactattg caaatagcct ataaaagtgt tgcgatatac gcggctaaag    1680
gagaaagaaa aaaagccgaa aatatttag aaatgactaa aaaatatcga actgtgggag    1740
tcgatttata ttcagaagta ttaagacatc ttgctagagc tatcattatt tttaattttg    1800
aaaatgcaga gattggggaa gaaaaaataa attatgctct tgagattttg gaagaatttg    1860
gaggaaagaa gataaaagaa ttctatcaga ataaaatgga aaagtatttg aaaaggtcaa    1920
tttagtctct tttgagctgt tgctttaaag caacagctca aaagagattt tctttattct    1980
agagcatata ctagagggtg aagataggtt gtctgaagca ttataacttg tcttttaaaa    2040
aattcaatca taaatataag gaggtatgat gaatcaaaaa aaattatcat tattcggttt    2100
tttcgcatta accgcttcaa tggttttgac tgtctatgag tatccgactt ttgccacgtc    2160
aaaattacat ttggtgttct ttttacttct cggaggacta ctatggtttt tgcctgtagc    2220
gctctgcgca gcagaaatgg cgacggttga aggctgaaaa aatggtggaa tctttagttg    2280
ggtcagtcaa actttaggtg agcgctttgg ttttgcagcc atattttttc agtggttcca    2340
aattacagta ggttttgtca ctatgatcta tttcatttta ggggccctct cttatgtgtt    2400
aaattttcag gcgctcaata cagatccatt gataaaattt attggtttac taatcatttt    2460
ttggggattg acttttttctc aattaggtgg gacgcaacgg actgccaaat tagtaaaagc    2520
tggctttgta gttggaatag tgattccatc ggttatcttg tttggattag cagcggcata    2580
ctttatcgga ggcaatccta tagaaatacc aattaacagc catgcttttg taccagattt    2640
ttcacaggta tcaactttag tagtttttgt ttcttttatt ctggcttata tgggggtaga    2700
agcctcagct tcacatatta atgaacttga aaatccaaaa cgaaattatc ccttagcaat    2760
gattttatta gtaattttgg ctatttcttt agatgccata ggtggatttt ctgtagcagc    2820
agttattcct caaaaagagt tatcattaag tgcaggggta atccaaactt ttcaaacgtt    2880
```

```
aatcttacat tttaatcatc atttgggatg gttagttaaa gtgattgcac taatgattgc    2940
ctttggggtt atgggagaag tgagttcatg ggttgttggt ccttctagag ggatgtttgc    3000
agcagcacaa agaggtttat taccaaaatt tttacgtaaa acgaatacac atgaagtccc    3060
tgttccttta gttatgattc aaggaatcat tgttacactt tggggcgctg tattaacttt    3120
tggaggagga ggaaataatt tatctttctt agttgccatt tcactgactg tagtgattta    3180
tttggtgggt tacctcttgt tctttattgt ttactttgtt ttaatctata aaaacaaaa    3240 tttaaagcgt acttataatg ttccaggtaa aataatagga aaaacaatca ttgcaggaat    3300
tggattctta ttatcaattt ttgctctatt tatttccttt gttcctccag catcaattgc    3360
gaaaaatgaa actcacacct atcaaatgat acttcttata agttttgttg tgaccgctat    3420
cttgccattt attatttatg aattgcatga taaaaaggga catgatacta ttgaagaacc    3480
aacacacttt aaagcaggag atgtgaaccc tgcgatttat ccagcagctc gtggagagca    3540
tcatattatt aaaaaagaag aacatatctt aaaacattga aaaattggag gatgtacata    3600
tgttatacgg aaaagaaaat cgagatgaag cggagttctt ggaaccaatt tttggttcag    3660
aaagtgaaca agtggattta cctaaatata aattagctca acaatcaatt gagcctcgag    3720
tggcctatca gttagttcaa gatgaaatgc tagatgaagg gaacgctcgt ttaaatttgg    3780
ccacattctg tcaaacttat atggaacctg aagcagtcaa gctgatgagt cagaccttgg    3840
aaaaaaatgc gattgacaaa tcagaatatc caagaacaac tgaaattgaa aaccgttgcg    3900
tcaacatgat cgctgacctt tggaatgcga gtgaaaaagg aaaaatttat gggacttcga    3960
caattggttc ttcagaagct tgtatgcttg ggggaatggc tatgaagttt tcttggcgta    4020
agcgagcaga aaaattaggc ctagatatta atgcgaaaaa gccaaactta gtcatttcct    4080
ctggttatca agtttgctgg gaaaaattct gtgtttattg ggatattgaa atgagagaag    4140
tgccaatgga tagagaacat atgtcaatca atttggaaaa agtgatggat tatgttgatg    4200
aatatacgat tggagtagtt ggaattatgg ggattactta tactggtcgt tatgatgata    4260
tcaaagcttt ggataatttg attgaagaat ataataaaca gacagactac aaagtttata    4320
ttcacgtaga tgctgcttca ggaggacttt atgctccttt tgttgagcca gaacttgagt    4380
gggatttccg tttgaaaaat gtcatttcaa tcaatacttc aggacataaa tatggtttag    4440
tatatcctgg tgtaggttgg gtcttgtggc gtgacaaaaa atatttacct gaagagttaa    4500 ttttttaaagt aagttatctt ggaggagaat taccaacaat ggcgattaat ttttctcaca    4560
gtgcttctca attaatcggt caatactata attttgtacg ttatggattt gatggatata    4620
aagctattca tgagagaacg cataaagtag ccatgtatatt agcagaagaa attgaaaaaa    4680
caggaatgtt tgagattatg aacgatgggg cacaattacc aattgtctgc tacaaattaa    4740
aagaaaattc aaaccgtggt tggaatcttt atgatttggc agatcgttta ttaatgaagg    4800
gatggcaagt gcctgcttat ccacttccta aaaatttgga aaatgaaatc attcaacgtt    4860
tagtaattcg agcagatttc gggatgaata tggcatttaa ctatgttcaa gatatgcaag    4920
aagcaattga tgcactaaat aaggctcata ttctatttca tcaggaacct gaaaataaaa    4980
catatggctt tactcactaa agataaaagc gatatatcta agatatatcg cttttatttt    5040
gttttaggct atttactaat tagcttgtcg cttattattt ttcatagtat ttatccaaaa    5100
tttccatttt taaggagta attttagata gggggcagt tagacttgtt cttaggaaga    5160
gcttatcttc aatgttgatg atacccagat atttaacttg agggtagtta gcattgactt    5220
ctataatttg ggcttttttc tcactaatat tttcgtctgt cacgggcaca tctaggttga    5280
```

-continued

```
ccgttctttc tttataagag taattttga gagcagcaat atttcggttt ggaataaaag    5340
tagtcgcacc gtcggctccg ataacagtaa tggaacgaat tcctacggtt ttcaccactc    5400
cctcaatatc aagaccggca aaggcaaccg tatccgcaac attgatttga tgttcaacga    5460
taataaagaa accattaatg atatcagcga ctaaatctcg tccagcgaaa ccaagagcga    5520
ctccaaggat acccgcgcca gctaggacat ttgcaacagg aattc                    5565
```

<210> SEQ ID NO 22
<211> LENGTH: 166
<212> TYPE: PRT
<213> ORGANISM: L. lactis MG1363

<400> SEQUENCE: 22

```
Ala Val Ile Leu Pro Lys Asn Cys Lys Ile Arg Gly Leu Asn Asp Ser
 1               5                  10                  15

Lys Lys Val Pro Lys Ser Lys His His Ala Ile Leu Ser Glu Ile Gln
            20                  25                  30

Glu Lys Ala Leu Ala Ile Gly Val Gly Ile Val Asp Ala Glu Lys Ile
        35                  40                  45

Asp Glu Val Asn Ile Tyr Glu Ala Thr Lys Ile Ala Met Ile Gln Ala
    50                  55                  60

Val Ser Lys Leu Ser Leu Lys Pro Glu His Leu Leu Ile Asp Ala Met
65                  70                  75                  80

Val Leu Asp Leu Pro Ile Ala Gln Thr Lys Ile Ile His Gly Asp Ala
                85                  90                  95

Arg Ser Ala Ser Ile Ala Ala Ala Ser Ile Val Ala Lys Val Thr Arg
            100                 105                 110

Asp Glu Met Met Lys Asp Phe Ala Leu Glu Phe Pro Glu Tyr Asp Phe
        115                 120                 125

Glu His Asn Ala Gly Tyr Gly Thr Ala Lys His Leu Ala Ala Leu Thr
    130                 135                 140

Lys Tyr Gly Ile Thr Arg Ile His Arg Lys Ser Tyr Glu Pro Ile Lys
145                 150                 155                 160

Ser Met Val Asn Phe Lys
                165
```

<210> SEQ ID NO 23
<211> LENGTH: 276
<212> TYPE: PRT
<213> ORGANISM: L. lactis MG1363

<400> SEQUENCE: 23

```
Met Tyr Lys Lys Tyr Gly Asp Cys Phe Lys Lys Leu Arg Asn Gln Lys
 1               5                  10                  15

Asn Leu Gly Leu Ser Tyr Phe Ser Lys Leu Gly Ile Asp Arg Ser Asn
            20                  25                  30

Ile Ser Arg Phe Glu His Gly Lys Cys Met Met Ser Phe Glu Arg Ile
        35                  40                  45

Asp Leu Met Leu Glu Glu Met Gln Val Pro Leu Ser Glu Tyr Glu Leu
    50                  55                  60

Ile Val Asn Asn Phe Met Pro Asn Phe Gln Glu Phe Phe Ile Leu Glu
65                  70                  75                  80

Leu Glu Lys Ala Glu Phe Ser Gln Asn Arg Asp Lys Ile Lys Glu Leu
                85                  90                  95

Tyr Ser Glu Val Lys Glu Thr Gly Asn His Leu Leu Thr Val Thr Val
            100                 105                 110
```

```
Lys Thr Lys Leu Gly Asn Ile Ser Gln Thr Glu Val Lys Glu Ile Glu
            115                 120                 125

Ala Tyr Leu Cys Asn Ile Glu Glu Trp Gly Tyr Phe Glu Leu Thr Leu
        130                 135                 140

Phe Tyr Phe Val Ser Asp Tyr Leu Asn Val Asn Gln Leu Glu Leu Leu
145                 150                 155                 160

Leu Phe Asn Phe Asp Lys Arg Cys Glu Asn Tyr Cys Arg Val Leu Lys
                165                 170                 175

Tyr Arg Arg Arg Leu Leu Gln Ile Ala Tyr Lys Ser Val Ala Ile Tyr
            180                 185                 190

Ala Ala Lys Gly Glu Arg Lys Lys Ala Glu Asn Ile Leu Glu Met Thr
        195                 200                 205

Lys Lys Tyr Arg Thr Val Gly Val Asp Leu Tyr Ser Glu Val Leu Arg
210                 215                 220

His Leu Ala Arg Ala Ile Ile Ile Phe Asn Phe Glu Asn Ala Glu Ile
225                 230                 235                 240

Gly Glu Glu Lys Ile Asn Tyr Ala Leu Glu Ile Leu Glu Glu Phe Gly
                245                 250                 255

Gly Lys Lys Ile Lys Glu Phe Tyr Gln Asn Lys Met Glu Lys Tyr Leu
            260                 265                 270

Lys Arg Ser Ile
        275

<210> SEQ ID NO 24
<211> LENGTH: 503
<212> TYPE: PRT
<213> ORGANISM: L. lactis MG1363

<400> SEQUENCE: 24

Met Asn Gln Lys Lys Leu Ser Leu Phe Gly Phe Phe Ala Leu Thr Ala
1               5                   10                  15

Ser Met Val Leu Thr Val Tyr Glu Tyr Pro Thr Phe Ala Thr Ser Lys
            20                  25                  30

Leu His Leu Val Phe Phe Leu Leu Leu Gly Gly Leu Leu Trp Phe Leu
        35                  40                  45

Pro Val Ala Leu Cys Ala Ala Glu Met Ala Thr Val Glu Gly Trp Lys
    50                  55                  60

Asn Gly Gly Ile Phe Ser Trp Val Ser Gln Thr Leu Gly Glu Arg Phe
65                  70                  75                  80

Gly Phe Ala Ala Ile Phe Phe Gln Trp Phe Gln Ile Thr Val Gly Phe
                85                  90                  95

Val Thr Met Ile Tyr Phe Ile Leu Gly Ala Leu Ser Tyr Val Leu Asn
            100                 105                 110

Phe Gln Ala Leu Asn Thr Asp Pro Leu Ile Lys Phe Ile Gly Leu Leu
        115                 120                 125

Ile Ile Phe Trp Gly Leu Thr Phe Ser Gln Leu Gly Gly Thr Gln Arg
130                 135                 140

Thr Ala Lys Leu Val Lys Ala Gly Phe Val Gly Ile Val Ile Pro
145                 150                 155                 160

Ser Val Ile Leu Phe Gly Leu Ala Ala Ala Tyr Phe Ile Gly Gly Asn
                165                 170                 175

Pro Ile Glu Ile Pro Ile Asn Ser His Ala Phe Val Pro Asp Phe Ser
            180                 185                 190

Gln Val Ser Thr Leu Val Val Phe Val Ser Phe Ile Leu Ala Tyr Met
        195                 200                 205
```

-continued

```
Gly Val Glu Ala Ser Ala Ser His Ile Asn Glu Leu Glu Asn Pro Lys
    210                 215                 220

Arg Asn Tyr Pro Leu Ala Met Ile Leu Leu Val Ile Leu Ala Ile Ser
225                 230                 235                 240

Leu Asp Ala Ile Gly Gly Phe Ser Val Ala Ala Val Ile Pro Gln Lys
                245                 250                 255

Glu Leu Ser Leu Ser Ala Gly Val Ile Gln Thr Phe Gln Thr Leu Ile
            260                 265                 270

Leu His Phe Asn His His Leu Gly Trp Leu Val Lys Val Ile Ala Leu
        275                 280                 285

Met Ile Ala Phe Gly Val Met Gly Glu Val Ser Ser Trp Val Val Gly
    290                 295                 300

Pro Ser Arg Gly Met Phe Ala Ala Ala Gln Arg Gly Leu Leu Pro Lys
305                 310                 315                 320

Phe Leu Arg Lys Thr Asn Thr His Glu Val Pro Val Pro Leu Val Met
                325                 330                 335

Ile Gln Gly Ile Ile Val Thr Leu Trp Gly Ala Val Leu Thr Phe Gly
            340                 345                 350

Gly Gly Gly Asn Asn Leu Ser Phe Leu Val Ala Ile Ser Leu Thr Val
        355                 360                 365

Val Ile Tyr Leu Val Gly Tyr Leu Leu Phe Phe Ile Val Tyr Phe Val
    370                 375                 380

Leu Ile Tyr Lys Lys Gln Asn Leu Lys Arg Thr Tyr Asn Val Pro Gly
385                 390                 395                 400

Lys Ile Ile Gly Lys Thr Ile Ile Ala Gly Ile Gly Phe Leu Leu Ser
                405                 410                 415

Ile Phe Ala Leu Phe Ile Ser Phe Val Pro Pro Ala Ser Ile Ala Lys
            420                 425                 430

Asn Glu Thr His Thr Tyr Gln Met Ile Leu Leu Ile Ser Phe Val Val
        435                 440                 445

Thr Ala Ile Leu Pro Phe Ile Ile Tyr Glu Leu His Asp Lys Lys Gly
    450                 455                 460

His Asp Thr Ile Glu Glu Pro Thr His Phe Lys Ala Gly Asp Val Asn
465                 470                 475                 480

Pro Ala Ile Tyr Pro Ala Ala Arg Gly Glu His His Ile Ile Lys Lys
                485                 490                 495

Glu Glu His Ile Leu Lys His
            500
```

<210> SEQ ID NO 25
<211> LENGTH: 466
<212> TYPE: PRT
<213> ORGANISM: L. lactis MG1363

<400> SEQUENCE: 25

```
Met Leu Tyr Gly Lys Glu Asn Arg Asp Glu Ala Glu Phe Leu Glu Pro
1               5                   10                  15

Ile Phe Gly Ser Glu Ser Glu Gln Val Asp Leu Pro Lys Tyr Lys Leu
            20                  25                  30

Ala Gln Gln Ser Ile Glu Pro Arg Val Ala Tyr Gln Leu Val Gln Asp
        35                  40                  45

Glu Met Leu Asp Glu Gly Asn Ala Arg Leu Asn Leu Ala Thr Phe Cys
    50                  55                  60

Gln Thr Tyr Met Glu Pro Glu Ala Val Lys Leu Met Ser Gln Thr Leu
65                  70                  75                  80
```

-continued

```
Glu Lys Asn Ala Ile Asp Lys Ser Glu Tyr Pro Arg Thr Thr Glu Ile
                85                  90                  95

Glu Asn Arg Cys Val Asn Met Ile Ala Asp Leu Trp Asn Ala Ser Glu
            100                 105                 110

Lys Gly Lys Ile Tyr Gly Thr Ser Thr Ile Gly Ser Ser Glu Ala Cys
            115                 120                 125

Met Leu Gly Gly Met Ala Met Lys Phe Ser Trp Arg Lys Arg Ala Glu
130                 135                 140

Lys Leu Gly Leu Asp Ile Asn Ala Lys Lys Pro Asn Leu Val Ile Ser
145                 150                 155                 160

Ser Gly Tyr Gln Val Cys Trp Glu Lys Phe Cys Val Tyr Trp Asp Ile
                165                 170                 175

Glu Met Arg Glu Val Pro Met Asp Arg Glu His Met Ser Ile Asn Leu
            180                 185                 190

Glu Lys Val Met Asp Tyr Val Asp Glu Tyr Thr Ile Gly Val Val Gly
            195                 200                 205

Ile Met Gly Ile Thr Tyr Thr Gly Arg Tyr Asp Asp Ile Lys Ala Leu
210                 215                 220

Asp Asn Leu Ile Glu Glu Tyr Asn Lys Gln Thr Asp Tyr Lys Val Tyr
225                 230                 235                 240

Ile His Val Asp Ala Ala Ser Gly Gly Leu Tyr Ala Pro Phe Val Glu
                245                 250                 255

Pro Glu Leu Glu Trp Asp Phe Arg Leu Lys Asn Val Ile Ser Ile Asn
            260                 265                 270

Thr Ser Gly His Lys Tyr Gly Leu Val Tyr Pro Gly Val Gly Trp Val
            275                 280                 285

Leu Trp Arg Asp Lys Lys Tyr Leu Pro Glu Glu Leu Ile Phe Lys Val
290                 295                 300

Ser Tyr Leu Gly Gly Glu Leu Pro Thr Met Ala Ile Asn Phe Ser His
305                 310                 315                 320

Ser Ala Ser Gln Leu Ile Gly Gln Tyr Tyr Asn Phe Val Arg Tyr Gly
                325                 330                 335

Phe Asp Gly Tyr Lys Ala Ile His Glu Arg Thr His Lys Val Ala Met
            340                 345                 350

Tyr Leu Ala Glu Glu Ile Glu Lys Thr Gly Met Phe Glu Ile Met Asn
            355                 360                 365

Asp Gly Ala Gln Leu Pro Ile Val Cys Tyr Lys Leu Lys Glu Asn Ser
370                 375                 380

Asn Arg Gly Trp Asn Leu Tyr Asp Leu Ala Asp Arg Leu Leu Met Lys
385                 390                 395                 400

Gly Trp Gln Val Pro Ala Tyr Pro Leu Pro Lys Asn Leu Glu Asn Glu
                405                 410                 415

Ile Ile Gln Arg Leu Val Ile Arg Ala Asp Phe Gly Met Asn Met Ala
            420                 425                 430

Phe Asn Tyr Val Gln Asp Met Gln Glu Ala Ile Asp Ala Leu Asn Lys
            435                 440                 445

Ala His Ile Leu Phe His Gln Glu Pro Glu Asn Lys Thr Tyr Gly Phe
450                 455                 460

Thr His
465
```